United States Patent
Urbig et al.

(10) Patent No.: US 10,758,621 B2
(45) Date of Patent: *Sep. 1, 2020

(54) LIQUID FORMULATION COMPRISING GM-CSF NEUTRALIZING COMPOUND

(71) Applicants: Amgen Research (Munich) GmbH, Munich (DE); Takeda GmbH, Constance (DE)

(72) Inventors: Thomas Urbig, Munich (DE); Thomas Boehm, Munich (DE); Wolfram Steinhilber, Stockach (DE); Michael Molhoj, Munich (DE)

(73) Assignees: Amgen Research (Munich) GmbH, Munich (DE); Takeda GmbH, Constance (DE)

( * ) Notice: Subject to any disclaimer, the term of this patent is extended or adjusted under 35 U.S.C. 154(b) by 27 days.

This patent is subject to a terminal disclaimer.

(21) Appl. No.: 15/922,777

(22) Filed: Mar. 15, 2018

(65) Prior Publication Data

US 2018/0207278 A1 Jul. 26, 2018

Related U.S. Application Data

(62) Division of application No. 14/429,204, filed as application No. PCT/EP2013/072761 on Oct. 31, 2013, now Pat. No. 9,919,051.

(60) Provisional application No. 61/720,892, filed on Oct. 31, 2012.

(30) Foreign Application Priority Data

Dec. 21, 2012 (EP) ..................... 12199191

(51) Int. Cl.
| | | |
|---|---|---|
| A61K 47/26 | (2006.01) | |
| A61K 47/18 | (2017.01) | |
| A61K 39/395 | (2006.01) | |
| C07K 16/24 | (2006.01) | |
| A61K 39/00 | (2006.01) | |

(52) U.S. Cl.
CPC ............ *A61K 47/26* (2013.01); *A61K 39/395* (2013.01); *A61K 39/3955* (2013.01); *A61K 39/39591* (2013.01); *A61K 47/183* (2013.01); *C07K 16/24* (2013.01); *C07K 16/243* (2013.01); *A61K 2039/505* (2013.01)

(58) Field of Classification Search
None
See application file for complete search history.

(56) References Cited

U.S. PATENT DOCUMENTS

| | | |
|---|---|---|
| 6,171,586 B1 | 1/2001 | Lam et al. |
| 6,309,636 B1 | 10/2001 | do Couto et al. |
| 6,685,940 B2 | 2/2004 | Andya et al. |
| 6,846,634 B1 | 1/2005 | Tomlinson et al. |
| 7,691,379 B2 | 4/2010 | Allan |
| 7,741,450 B2 | 6/2010 | Sass et al. |
| 7,807,155 B2 | 10/2010 | Di Padova et al. |
| 8,017,748 B2 | 9/2011 | Raum et al. |
| 8,318,168 B2 | 11/2012 | Sass et al. |
| 8,623,364 B2 | 1/2014 | Sass et al. |
| 2001/0014326 A1 | 8/2001 | Andya et al. |
| 2006/0088523 A1 | 4/2006 | Andya et al. |
| 2006/0193850 A1 | 8/2006 | Warne |
| 2011/0182905 A1 | 7/2011 | Takada |
| 2011/0189082 A1 | 8/2011 | Kirchner |
| 2012/0230982 A1 | 9/2012 | Zhao et al. |
| 2014/0086928 A1 | 3/2014 | Sass et al. |

FOREIGN PATENT DOCUMENTS

| | | |
|---|---|---|
| CN | 101001645 A | 7/2007 |
| EP | 0265384 A2 | 4/1988 |
| EP | 0344957 A1 | 12/1989 |
| EP | 0499161 A2 | 8/1992 |
| EP | 1256348 A1 | 11/2002 |
| EP | 1593690 A | 11/2005 |
| EP | 2399604 A1 | 12/2011 |
| JP | 2009-525986 A | 7/2009 |
| JP | 2010-531306 A | 9/2010 |
| WO | WO 2003/009817 A2 | 2/2003 |
| WO | WO 2003/068924 | 8/2003 |
| WO | WO 2006/013107 A1 | 2/2006 |
| WO | WO 2006/066088 A2 | 6/2006 |
| WO | WO 2006/111353 A2 | 10/2006 |
| WO | WO 2006/122797 A1 | 11/2006 |
| WO | WO 2009/038760 A2 | 3/2009 |
| WO | WO 2009/064399 A1 | 5/2009 |
| WO | WO 2009/133103 A1 | 11/2009 |
| WO | WO 2010/071923 A1 | 7/2010 |
| WO | WO 2010/128035 A1 | 11/2010 |
| WO | WO 2011/017070 A1 | 2/2011 |
| WO | WO 2011/080209 A2 | 7/2011 |
| WO | WO 2011/104381 A2 | 9/2011 |
| WO | WO 2014/044768 A1 | 3/2014 |

OTHER PUBLICATIONS

Andoh et al.: "*Interleukin-17 augments tumor necrosis factor-alpha-induced granulocyte and granulocyte/macrophage colony-stimulating factor release from human colonic myofibroblasts*"; J Gastroenterol., Aug. 2005; 40(8):802-10.

(Continued)

Primary Examiner — Shulamith H Shafer
(74) Attorney, Agent, or Firm — DLA Piper LLP (US)

(57) ABSTRACT

The present invention relates to aqueous formulations comprising a compound neutralizing GM-CSF in concentrations of at least about 20 mg/ml, a tonicity modifier and a buffer, wherein the composition is stable. The ingredients of the formulation preferably provide stability to the compound neutralizing GM-CSF in view of long-term storage. In a preferred aspect, the formulation is for use in therapy, preferably for use in the treatment of inflammatory and autoimmune disorders, preferably including allergic and psoriatic disorders, as well as arthritic and asthmatic disorders. Furthermore, a kit comprising the formulation of the invention is provided.

18 Claims, 2 Drawing Sheets
Specification includes a Sequence Listing.

(56) References Cited

OTHER PUBLICATIONS

Beiboer et al.: "Guided Selection of a Pan Carcinoma Specific Antibody Reveals Similar Binding Characteristics Yet Structural Divergence Between the Original Murine Antibody and its Human Equivalent"; J. MoL Biol. 296:833-849 (2000). (Abstract).
Carpenter et al.: "Rational Design of Stable Lyophilized Protein Formulations: Some Practical Advice"; Pharm. Res. (1997), 14(8):969-975.
Chabaud et al.: "Rheumatoid Arthritis Synoviocytes and Its and Leukemia Inhibitory Factor Production by Enhancing Effect of IL-17 on 1L-1-Induced IL-6 Regulation by Th2 Cytokines"; J Immunol 1998; 161:409-414. (Abstract).
Coleman, P.M.: "Effects of amino acid sequence changes on antibody-antigen interactions"; Research in immunology, 145:33-36, 1994.
Crane et al.: "Cytokine regulation of granulocyte-macrophage colony-stimulating factor (GM-CSF) production by human retinal pigment epithelial cells"; Clin Exp Immunol 1999; 115:288-293.
Danis et al.: "Effects of granulocyte-macrophage colony-stimulating factor (GM-CSF), IL-2, interferon-gamma (IFN-gamma), tumour necrosis factor-alpha (TNF-alpha) and 1L-6 on the production of immunoreactive IL-1 and TNF-alpha by human monocytes"; Clin Exp Immunol. 1991 Jul;85(1)143-50.
Eberhardt et al.: "/identification of Two Potential Receptor Binding Sites for hGM-CSF"; Braz. J. Chem. Eng. 20: 1-9 (2003).
European Examination Report dated Feb. 13, 2017, regarding EP 13 798 590.9.
European Examination Report dated Apr. 15, 2016, regarding EP 13 798 260.9.
Fernandez et al.: "Transcriptional and post-transcriptional regulation of GM-CSF-induced IL-1 beta gene expression in PMN"; J. Leukoc. Biol., 1996, 59: 598-603. (Abstract).
Gokarn et al.: "Self-Buffering Antibody Formulations," J. Pharm. Sci. (2008), 97(8):3051-3066, XP-002638374, Wiley-Liss, Inc. and the American Pharmacists Association.
Japanese Office Action dated Jul. 26, 2017, regarding JP 2015-538509.
Kanakura et al.: "Identification of Functionally Distinct Domains of Human Granulocyte-Macrophage Colony-Stimulating Factor Using Monoclonal Antibodies"; Blood 77:1033-1043 (1991).
Koenders et al.: "IL-17 Synergy with TNF Causes Striking Cartilage Erosion In Vivo"; American College of Rheumatology, 2007 Annual Scientific Meeting.
Lakhtina et al.: "Immunoenzyrne Determination of Human Granulocyte-Macrophage Colony-Stimulating Factor Using Monoclonal Antibodies"; Bioorg Khim 25:673-678 (1999) (Abstract).
Li et al.: "Human Antibodies for Immunotherapy Development Generated via a Human Be Cell Hybridoma Technology"; PNAS 103:3557-3562 (2006).
MacCallum et al.: "Antibody-antigen Interactions: Contact Analysis and Binding Site Topography"; J. Mol. Biol., 1996, 262:732-745. (Abstract).
McAllister et al.: "In vitro effector activity of Pneumocystis murina-specific T-cytotoxic-1 CD8' T cells: Role of granulocyte-macrophage colony-stimulating factor"; Infect Immun. 73:7450-7, 2005.
Numasaki et al.: "Interluekin-17 Promotes Angiogenesis and Tumor Growth" Blood 101:2620-2627 (2003).
Padlan et al.: "Structure of an antibody-antigen complex: Crystal structure of the HyHEL-10 Fab-lysozyme complex"; Proc. Natl. Acad. Sci. USA, 1989, 86 : 5938-5942.
Paul: "Fv Structure and Diversity in Three Dimensions"; Fundamental Immunology, 3rd Edition, 1993, pp. 292-295.
Rudikoff et al.: "Single amino acid substitution altering antigen-binding specificity"; Proc Natl Acad Sci USA, Mar. 1982, vol. 79, pp. 1979-1983.
Sane et al.: "Raman Spectroscopic Characterization of Drying-Induced Structural Changes in a Therapeutic Antibody: Correlating Structural Changes with Long-Term Stability,"J. Pharm. Sci. (2004), 93(4)1005-1018, XP-002578903, Wiley-Liss, Inc. and the American Pharmacists Association.
Shen et al.: "Structure-function relationships in the 1L-17 receptor: implications for signal transduction and therapy"; Cytokine. Feb. 2008;41(2):92-104.
Smith et al.: "Synergism between GM-CSF and IFNy: Enhanced immunotherapy in mice with glioma"; Int. J. Cancer 120: 75-80, 2006.
Van Dijk et al.: "Human Antibodies as Next Generation Therapeutics"; Current Opinion in Chemical Biology 5:368-374 (2001).
Van Nieuwenhuijze et al.: "Synergism Between GM-CSF and IL-17 Causes Enhanced Joint Pathology Via the Production of IL-6-and IL-23"; Ann. Rheum. Dis., 2014, A24, 73(Suppl 1), BMJ Publishing Group Ltd, London, UK. (Abstract).
Wang et al.: "Antibody Structure, Instability, and Formation,"J. Pharm. Sci. (2007), 96(1):1-26, XP09084505, Wiley-Liss, Inc. and the American Pharmacists Association.
Yoon et al.: "Synergistic anti-tumor effects with co-expression of GM-CSF and IFNy in murine tumors"; Int. J. Cancer 77: 907-12, 1998.

LIQUID FORMULATION COMPRISING GM-CSF NEUTRALIZING COMPOUND

CROSS-REFERENCE TO RELATED APPLICATIONS

This application is a divisional application of U.S. application Ser. No. 14/429,204, now issued as U.S. Pat. No. 9,919,051; which is a 35 USC § 371 National Stage application of International Application No. PCT/EP2013/072761 filed Oct. 31, 2013, now expired; which claims the benefit under 35 USC § 119(e) to U.S. Application Ser. No. 61/720,892 filed Oct. 31, 2012, and the benefit under 35 USC § 119(a) to EP Application Serial No. 12199191.3 filed Dec. 21, 2012. The disclosure of each of the prior applications is considered part of and is incorporated by reference in the disclosure of this application.

BACKGROUND OF THE INVENTION

Field of the Invention

The present invention relates to stable liquid formulations comprising a compound neutralizing Granulocyte-macrophage colony stimulating factor (GM-CSF). The ingredients of the formulations preferably provide stability over long term storage and freeze-thaw cycles. In a preferred aspect, the formulations are for use in therapy, preferably for use in the treatment of inflammatory and autoimmune disorders, preferably including allergic and psoriatic disorders, as well as arthritic and asthmatic disorders. Furthermore, a kit comprising the formulations of the invention is provided.

Background Information

Proteins are used in a wide range of applications in the fields of pharmaceuticals, veterinary products, cosmetics and other consumer products, foods, feeds, diagnostics, industrial chemistry and decontamination. At times, such uses have been limited by constraints inherent in proteins themselves or imposed by the environment or media in which they are used. Such constraints may result in poor stability of the proteins, variability of performance or high cost. Due to the advent of biotechnology it is possible to produce a wide variety of proteins for therapeutic applications. After their production, protein pharmaceuticals are usually stored prior to their use. Due to the fact that proteins are generally larger and more complex than "traditional" pharmaceuticals, formulation and processing of protein pharmaceuticals that are suitable for storage can be particularly challenging. For reviews of protein pharmaceutical formulation and process design, see Carpenter et al. (1997), Pharm. Res. 14:969-975; Wang (2000), Int. J. Pharmaceutics 203:1-60; and Tang and Pikal (2004), Pharm. Res. 21:191-200.

Several factors can be considered in designing formulations and processes for protein pharmaceutical production. Of primary concern is the stability of the protein through any or all steps of manufacture, shipping, and handling steps, which may include preparation of the composition, freezing, lyophilizing, drying, storage, shipping, reconstitution, freeze/thaw cycles, and post-reconstitution storage by the end user. Other potential considerations include ease and economy of manufacture, handling, and distribution; composition of the final product for patient administration; and ease of use by the end user, including solubility of the lyophilized formulation upon reconstitution.

Liquid formulations may satisfy certain objectives. Possible advantages of liquid formulations include ease and economy of manufacture and convenience for the end user. Frequently, when stored for extended periods polypeptides are unstable in solution (Manning et al (1989), Pham. Res. 6:903-918). Accordingly, additional processing steps have been developed to allow for a longer shelf life including drying, e.g., lyophilization. Lyophilized formulations may also provide certain advantages. Potential benefits of lyophilization include improved protein stability as well as ease and economy of shipping and storage. However, lyophilized pharmaceutical compositions may be less convenient for the end user.

In addition to the choice of the basic form of the composition (e.g., lyophilized, liquid, frozen, etc.), optimization of a protein formulation typically involves varying the components of the formulation and their respective concentrations to maximize protein stability. A variety of factors may affect protein stability, including ionic strength, pH, temperature, freeze/thaw cycles, shear forces, freezing, lyophilizing, drying, agitation, and reconstitution. Protein instability may be caused by physical degradation (e.g., denaturation, aggregation, or precipitation) or chemical degradation (e.g., deamidation, oxidation, or hydrolysis). Optimization of formulation components and concentrations is solely based on empirical studies and/or rational approaches to overcoming sources of instability.

Sometimes, in long-term storage of pharmaceutical compositions containing polypeptides, including aqueous and lyophilized formulations, active polypeptides can be lost due to aggregation and/or degradation.

Accordingly, typical practices to improve polypeptide stability can be addressed by varying the concentration of elements within the formulation, or by adding excipients to modify the formulation (U.S. Pat. Nos. 5,580,856 and 6,171,586 and U.S. Patent application Nos. US 2003/0202972, US 2003/0180287). U.S. Pat. No. 5,580,856 is a prototype patent disclosing agents such as natural polymers, surfactants, sulfated polysaccharides, proteins and buffers which can be added to stabilize a dried protein during or after rehydration. However, apart from many options, U.S. Pat. No. 5,580,856 does not teach which stabilizer should be added for which protein. Accordingly, while the skilled reader is made aware of that many options, he or she would have to find out for his/her protein the best conditions among the many options described by U.S. Pat. No. 5,580,856. US patent application 2003/0202972 describes a stable lyophilized formulation of an anti-Her2 antibody, wherein the stabilizer is sugar, trehalose, or a buffer. Yet, while these stabilizers may be useful for an antibody, they cannot be extrapolated to other proteins. US patent application 2003/0180287 is similar to US 2003/0202972 in that it also describes a stable solution of an immunoglobulin-like protein, i.e., a protein containing an Fc domain. The stabilizer may be sodium phosphate, potassium phosphate, sodium or potassium citrate, maleic acid, ammonium acetate, Tris-buffer, acetate, diethanolamine, histidine, lysine or cysteine. Among these chemically distinct stabilizers which could be chosen by the skilled reader, lysine turned out to be suitable. However, like with US 2003/0202972, the specific stabilizer is merely suitable for a specific protein, here an Fc domain containing protein, and cannot per se be extrapolated to another protein. Accordingly, the use of additives cannot be extrapolated from a specific protein to another un-related protein. Indeed, the use of additives—while improving storage—can still result in inactive polypeptides. In addition, in the case of lyophilization, the rehydration step can introduce conditions that result in inactivation of the polypeptide by, for example, aggregation or denaturation (Hora et al. (1992), Pharm. Res., 9:33-36; Liu et al. (1991), Biotechnol. Bioeng., 37:177-184). In fact, aggregation of polypeptides is undesirable as it may result in immunogenicity (Cleland et al. (1993), Crit. Rev. Therapeutic Drug Carrier Systems, 10:307-377; and Robbins et al. (1987), Diabetes, 36:838-845).

Maintenance of biological activity during the development and manufacture of pharmaceutical products depends on the inherent stability of the macromolecule, as well as the stabilization techniques employed. A range of protein stabilization techniques exist; including addition of chemical "stabilizers" to the aqueous solution or suspension of a protein. For example, U.S. Pat. No. 4,297,344 discloses stabilization of coagulation factors II and VIII, antithrombin III and plasminogen against heat by adding selected amino acids. U.S. Pat. No. 4,783,441 discloses a method for stabilizing proteins by adding surface-active substances. U.S. Pat. No. 4,812,557 discloses a method for stabilizing interleukin-2 using human serum albumin. Freeze/thaw methods in which the preparation is mixed with a cryoprotectant and stored at very low temperatures is another option to stabilize a protein. However, not all proteins will survive a freeze/thaw cycle. Cold storage with cryoprotectant additive, normally glycerol is a further option. Storage in the glass form, as described in U.S. Pat. No. 5,098,893 could also be made. In this case, proteins are dissolved in water-soluble or water-swellable substances which are in amorphous or glassy state. The most widely used method for the stabilization of proteins is freeze-drying or lyophilization. Whenever sufficient protein stability cannot be achieved in aqueous solution, lyophilization provides the most viable alternative. One disadvantage of lyophilization is that it requires sophisticated processing, is time consuming and expensive. In addition, if lyophilization is not carried out carefully, most preparations are at least partially denatured by the freezing and dehydration steps of the technique. The result is frequently irreversible aggregation of a portion of protein molecules, rendering a formulation unacceptable for parenteral administration.

Generally spoken, the degradation of proteins has been well described in the literature, but the storage and solubility of compounds neutralizing Granulocyte-macrophage colony stimulating factor (further referred to as GM-CSF), in particular of polypeptides and anti-GM-CSF antibodies, has not been described.

In addition, while it was known in the art that a multitude of options for protein stabilizing agents as well as for agents which allow a high concentration of a protein while being kept stable were available, up to the present invention, it was not recognized in the art that a formulation comprising compounds neutralizing GM-CSF in high concentrations could be unstable and thus require improvement.

In the preparation of a pharmaceutical composition comprising a protein, such as an antibody, e.g., a monoclonal antibody, it is an aim to develop high concentration liquid formulations due to the potential of subcutaneous administration which results in higher convenience for the patient. However, there is a general consensus that development of high-concentration formulations of antibodies, in particular monoclonal antibodies, poses serious challenges with respect to the physical and chemical stability of the monoclonal antibodies such as increased formation of soluble as well as insoluble aggregates which enhance the probability of an immunogenic response as well as give rise to low bioactivity.

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other challenges such as blockage of tubing, membranes, or pumps when the polypeptide-containing pharmaceutical composition is administered using an infusion system. Furthermore, high-concentration formulations of antibodies have been reported to result in increased viscosity thereby creating serious challenges for the manufacturability and injectability. Highly viscous formulations are difficult to manufacture, draw into a syringe, and inject. The use of force in manipulating the viscous formulations leads to excessive frothing, which can lead to denaturation and inactivation of active monoclonal antibodies.

Therefore, there is a high need for a stable high-concentrated protein pharmaceutical composition comprising a compound neutralizing GM-CSF, e.g., an antibody and having a low and feasible viscosity which is suitable for subcutaneous administration, such as in a ready to use device. Furthermore, from a patient point of view it would be highly desirable to have room temperature stable products. At this moment, there are in particular no marketed antibody formulations where storage at room temperature is a possibility throughout the shelf life of the drug product. Typically, increased protein aggregation occurs causing an unacceptably high level of aggregates and protein related impurities, which may give rise to immunogenic reactions. Many of the marketed monoclonal antibody products contain surfactants in their formulation. Typically, surfactants are added in order to reduce interfacial stress which can induce protein aggregation and particle formation leading to unacceptable product quality. Examples of interfacial stress could be contact of the protein with i) air ii) container closure material, such as rubber plunger, piston, glass, pre-filled syringes iii) production related materials, such as steel tanks, tubings and pumps iv) ice, during freeze/thaw, etc. However, surfactants such as polysorbates typically contain a residue of peroxides which may oxidize the protein molecule leading to a compromised product quality. Furthermore, from a manufacturing point of view addition of polysorbates requires an extra step in the production since ultra/diafiltration is challenging to conduct when the formulation contains said polysorbates. Preventing the formation of oxidized products is a challenging issue, therefore a careful handling of polysorbates is required in order to control the formation of oxidized products. Thus, it would also be desirable to design formulations without surfactants, both from a stability—and manufacturing point of view.

Granulocyte-macrophage colony stimulating factor (GM-CSF), initially identified as a hematopoietic growth factor, has more recently been shown to be an important cytokine in inflammation and autoimmunity. Elevated levels of GM-CSF mRNA or protein are measured in a variety of inflammatory sites including in allergic and psoriatic patients, arthritic and asthmatic patients. Numerous in vivo studies have shown over the past few years that blockade of GM-CSF via neutralizing antibodies can prevent or even cure pro-inflammatory diseases in various models of inflammation including models for arthritis experimental autoimmune encephalitis, psoriasis, and lung disease. Therefore, it is highly desirable to have available a formulation with a GM-CSF neutralizing compound that is, in particular, stable, contains high amounts of a GM-CSF neutralizing compound and/or can be administered via the subcutaneous route.

Hence, the technical challenge of the present invention is to comply with the needs described above.

The present invention addresses these needs and thus provides as a solution to the technical challenge the embodiments concerning formulations as well as methods and uses applying these formulations in the treatment of subjects suffering from diseases which would benefit from the administration of compounds neutralizing GM-CSF. These embodiments are characterized and described herein, illustrated in the Examples, and reflected in the claims.

Definitions

It must be noted that as used herein, the singular forms "a", "an", and "the", include plural references unless the context clearly indicates otherwise. Thus, for example, reference to "an antibody" includes one or more of such different antibodies and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having" or could even be replaced by consisting of.

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "consisting essentially of" and "consisting of" may be replaced with each other.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

DETAILED DESCRIPTION OF THE INVENTION

With the goal in mind of providing a formulation which has a high concentration of compounds neutralizing GM-CSF, the present inventors recognized that compounds neutralizing GM-CSF may be unstable at high concentrations and may also be unstable over a prolonged period of storage.

Indeed, there are many ways in which compounds neutralizing GM-CSF, like proteins, can be unstable. For example, protein instability could be caused by protein aggregation or degradation, but also by chemical instability due to deamination, deamidation, oxidation, disulfide bond breakage and formation, hydrolysis, succimmidation, non-disulfide crosslinking, deglycosylation or "enzymatic browning" (Maillard reaction) or any combination of these phenomena; see, for example, Wang et al. (1999), Int. J. Pharm. 185:129-188. Furthermore, physicochemical parameters such as the temperature, pH value, surface adsorption, salts, metal ions, chelating agents, physical forces such as shear forces, protein denaturants, non-aqueous solvents, protein concentration, source and purity of the protein, protein morphism or pressure can influence protein stability.

Yet, while many factors can influence protein stability, many measures could also be taken to stabilize a protein. For example, a protein can be stabilized internally (by changing amino acids) or externally. External stabilization could be achieved by the addition of chelating agents, metal ions, reducing agents, polymers, polyethylene glycols/polyols, serum albumin, surfactants, sugars and polyols, fatty acids and phospholipids, amino acids, buffers, etc.; see, for example, Wang, Y and Hanson M (1988), J. Parental Sci. & Technology, 42, Supplement: 4-26; Wang et al. (1999), Int. J. Pharm. 185:129-188. In sum, for stabilizing GM-CSF neutralizing compounds such as antibodies in a formulation, the skilled person would have had many options available.

In the present case, the inventors observed that the compounds neutralizing GM-CSF may show aggregation and/or may not be dissolved in higher concentrations. Many different factors can, cause aggregation of a protein in a formulation. Typical purification and storage procedures can expose protein formulations to conditions and components that cause the protein to aggregate. For example, proteins in a formulation may aggregate as a result of any one or more of the following: storage, exposure to elevated temperatures, the pH of the formulation, the ionic strength of the formulation, and the presence of certain surfactants (e.g., polysorbate-20 and polysorbate-80) and emulsifying agents. Similarly, proteins may aggregate when exposed to shear stress, such as, reconstituting a lyophilized protein cake in solution, filter-purifying a protein sample, freeze-thawing, shaking, or transferring a protein solution via syringe. Aggregation can also occur as a result of interactions of polypeptide molecules in solution and at the liquid-air interfaces within storage vials. Conformational changes may occur in polypeptides adsorbed to air-liquid and solid-liquid interfaces during compression or extension of the interfaces resulting from agitation during transportation. Such agitation can cause the protein of a formulation to aggregate and ultimately precipitate with other adsorbed proteins.

In addition, exposure of a protein formulation to light can cause the protein to aggregate. The present invention thus provides formulations which enable high concentrations of compounds neutralizing GM-CSF and which reduce aggregation of these compounds. Without being bound by theory the reduction of aggregation is believed to be achieved by controlling one or more of the above-mentioned aggregation mechanisms. This can result in, for example, improved product stability, and greater flexibility in manufacturing processes and storage conditions.

The present inventors aimed at providing a formulation with a high concentration of compounds neutralizing GM-CSF, in order to, e.g., enable a lower injection volume which is suitable to reduce side effects like pain due to high injection volume or allows for subcutaneous administration at a low volume.

That being so, the present inventors have observed during their studies a certain instability of compounds neutralizing GM-CSF and, thus, aimed at improving this undesired observation. Accordingly, they aimed at concentrating compounds neutralizing GM-CSF while keeping it in solution, i.e., in a dissolved stage. In doing so, they had a multitude of options and alternatives available, without, however, any indication that any of them would be suitable to solve the objective problem.

"Dissolved stage" means that the compound neutralizing GM-CSF, preferably in a concentration of at least about 20 mg/ml, is in solution, i.e., (dis)solved and/or dispersed directly in the aqueous solution (i.e., in the aqueous phase) of the formulation. Preferably, the compound neutralizing GM-CSF is homogenously (dis)solved and/or dispersed. Homogenously means that the compound neutralizing GM-CSF that is (dis)solved and/or dispersed in the aqueous formulation is nearly evenly, preferably evenly, distributed in the aqueous formulation so that the concentration ("c") of the compound neutralizing GM-CSF ("n" in case of molar mass or "m" in case of mass) is nearly identical, preferably identical in (or throughout) the volume ("v") of the aqueous solution, i.e., c=n/v or c=m/v, respectively, is nearly constant, preferably constant. Preferably there is no concentration gradient within the formulation.

Accordingly, the stable formulation of the present invention comprising a compound neutralizing GM-CSF can preferably be regarded as an aqueous solution, wherein a compound neutralizing GM-CSF is directly dissolved and/or dispersed therein.

A "solution" is a homogenous mixture of two or more substances/components. In such a mixture, a solute (in the present invention a compound neutralizing GM-CSF) is dissolved (as described above) in another substance (in the present invention preferably an aqueous formulation), also known as solvent.

Given the above, the compound neutralizing GM-CSF is preferably not heterogeneously (dis)solved and/or dispersed in the aqueous solution. The term "dissolved state" also includes that the compound neutralizing GM-CSF is preferably essentially not emulsified, or more preferably not emulsified at all in the aqueous solution.

Also, the term "dissolved state" includes that the compound neutralizing GM-CSF is preferably not essentially encapsulated and/or entrapped (preferably less than 2%, 1%, or 0.5% of the compound neutralizing GM-CSF may be encapsulated and/or entrapped, or more preferably not encapsulated and/or entrapped at all, e.g., in liposomes, multilamellar liposomes or the like.

Accordingly, one preferred embodiment of the present invention is a liquid formulation containing a compound neutralizing GM-CSF which is stable and does not undergo the formation of conjugates/aggregates or fragments/degradation products when stored for a long period, and which formulation is suitable for subcutaneous administration.

Specifically, after testing many different stabilizing agents, the present inventors found that compounds neutralizing GM-CSF could be stabilized if a tonicity modifier is added to the solution which is to be stored. Examples for tonicity modifiers include, but are not limited to, sugars and sugar alcohols. Simple sugars are called monosaccharides and include glucose, fructose, galactose, xylose, ribose, mannose, lactulose, allose, altrose, gulose, idose, talose, arabinose and lyxose. More preferred for the present inventions are disaccharides which include for example sucrose, maltose, lactose, isomaltose, trehalose and cellubiose. Sugar alcohols include sorbitol, mannitol, glycerin, erythritol, maltitol, xylitol, polyglycitol. In a preferred embodiment, the sugar is a non-reducing sugar such as sucrose or trehalose. Non-reducing sugars are characterized by the absence of an open chain structure, so they are not susceptible to oxidation-reduction reactions. Therefore one or more of non-reducing sugars, such as sucrose or trehalose, or one or more of sugar alcohols, such as mannitol or sorbitol could be added to the formulation comprising a compound neutralizing GM-CSF. Also combinations of non-reducing sugars and sugar alcohols could be added to the solution, such as sucrose and mannitol, sucrose and sorbitol, trehalose and mannitol, or trehalose and sorbitol. More preferably the sugar alcohols mannitol and/or sorbitol are added, preferably in their D-form, most preferably sorbitol is added to the solution. The concentration of the tonicity modifier, preferably sorbitol, is between about 1% and about 15% (w/v), preferably between about 2% and about 10% (w/v), more preferably between about 3% and about 7% (w/v), more preferably between about 4% and about 6% (w/v) and most preferably about 5% (w/v).

Another specifically preferred substance to stabilize compounds neutralizing GM-CSF at a high concentration with regard to long-term storage is a buffer system with a pH of between about 4 and about 10, preferably between about 4 and about 7, more preferably between about 4 and about 6 or between about 5 and about 7, even more preferably between about 5.5 and about 6.5, and most preferably with a pH of about 5.8. The buffer may be preferably selected from a histidine buffer, an acetate buffer and a citrate buffer. When referred herein, an amino acid is meant to be an L-amino acid or D-amino acid, wherein L-amino is preferred. Preferably histidine or a salt thereof; is used for the buffer system. Preferably the salt is a chloride, phosphate, acetate or sulphate, more preferably the salt is a chloride. The pH of the histidine buffer system is between about 5 and about 7, preferably between about 5.5 and about 6.5, more preferred the pH is about or exactly 5.8. The pH may be adjusted by the use of conventionally used bases and acids, preferably NaOH. The concentration of the buffer system, preferably the histidine buffer system, is between about 10 mM and about 50 mM, preferably between about 20 mM and about 40 mM, more preferably about 30 mM.

According to a preferred embodiment, a combination of the buffer system, preferably the histidine buffer, and the tonicity modifier, preferably the sugar alcohol, more preferably mannitol or even more preferably sorbitol, is used to stabilize the compounds neutralizing GM-CSF in the solution, in order to prevent aggregation and to render the formulation sufficiently stable for long-term storage and/or one or more freeze/thaw cycles. It was shown that it is preferable in terms of stability to have about 6% (w/v) and higher of sugar alcohol, preferably sorbitol, in the formulation. However, the upper limit for osmolality of the formulation is set to be about 470 mOsm/kg which is still hyperosmotic but similar to the osmolality of an approved product (Synagis; I.m. administration). A compromise between optimal stability, tonicity and concentration of the compound neutralizing GM-CSF had therefore to be found as described in the Examples of the present invention. A preferable concentration of sugar alcohol, preferably sorbitol, is therefore between about 3% and about 7% (w/v), more preferably between about 4% and about 6% (w/v) and most preferably about 5% (w/v).

In some embodiments of the present invention, the formulations or compositions of the invention comprising a compound neutralizing GM-CSF do not require further excipients in addition to those disclosed above (i.e., a buffer and a tonicity modifier), such as, for example, surfactants and amino acids, which are used in traditional formulations to stabilize proteins in solution. In addition, the formulations described herein are preferred over standard formulations because they have decreased immunogenicity due to the lack of additional agents commonly needed for protein stabilization.

It is known that amino acids are useful to stabilize proteins at a high concentration by, inter alia, mediating protein solubility and/or inhibiting protein aggregation. Although threonine (e.g., at 250 mM) indicates a minor stabilizing effect, the liquid formulation of the present invention is preferably free from further amino acids.

Furthermore, it is preferred that the present formulation is free or essentially free of sodium chloride. By "essentially free" is meant that the concentration of sodium chloride is at or very near to 0 (zero) mM, e.g., less than about 50 mM, preferably less than about 20 mM, more preferably less than about 10 mM, even more preferably less than about 5 mM and most preferably less than about 2 mM or even less than about 1 mM.

In biopharmaceutical products, the addition of surfactants can be useful to reduce protein degradation during storage. The polysorbates 20 and 80 (Tween 20 and Tween 80) are well established excipients for this purpose. However, due to no or negative effects on the stability of the compounds neutralizing GM-CSF, the liquid formulation of the present invention preferably does not comprise any surfactants.

The concentration of the respective compounds neutralizing GM-CSF used is at least about 20 mg/ml, preferably at least about 50 mg/ml, more preferably at least about 100 mg/ml in the liquid formulation which is to be stored, freeze/thawed and/or ready to use. Concentrations of about 20 mg/ml to about 200 mg/mg, preferably about 50 mg/ml to about 200 mg/ml, more preferably about 100 mg/ml to about 180 mg/ml, even more preferably about 130 mg/ml to about 170 mg/ml, even more preferably about 135 mg/ml to about 165 mg/ml, and most preferred about 150 mg/ml are used in the present invention.

The shelf life of the produced liquid formulation has a preferred minimum requirement of 24 months at 2 to 8° C., preferably 36 months at 2 to 8° C., more preferably 48 months at 2 to 8° C., most preferably 60 months at 2 to 8° C., or at least 28 days at ambient temperature (25° C.±2° C.).

The present invention is directed to a stable formulation, preferably a stable liquid formulation that surprisingly allows for long-term storage of compounds neutralizing GM-CSF. This formulation is useful, in part, because it is more convenient to use for the patient, as the compounds neutralizing GM-CSF of this formulation are highly concentrated so as to reduce side effects like pain due to high volume injection.

Accordingly, one aspect of the invention is based, on the discovery that formulations comprising
a compound neutralizing GM-CSF,
a buffer system preferably selected from a histidine buffer, an acetate buffer and/or a citrate buffer with a preferred pH of between 5 and 7,
and a tonicity modifier preferably selected from non-reducing sugars, such as sucrose or trehalose, or sugar alcohols, such as mannitol or sorbitol are rendered sufficiently stable for long-term storage and/or freeze/thaw cycles and/or shear stress (shaking stability). The formulation of the invention has many advantages over standard buffered formulations. In one aspect, the formulation shows minimal aggregation behaviour upon long-term storage without deleterious effects that might be expected with high protein formulations. Other advantages of the formulation according to the invention are: minimal fragmentation of the compound neutralizing GM-CSF and no significant impact on bioactivity of the compound neutralizing GM-CSF over long-term storage, and low viscosity of the composition. Finally, in a preferred embodiment, the formulation is free of further excipients such as surfactants, additional amino acids and/or sodium chloride.

Preferred embodiments of the first aspect of the invention are the following: Formulations according to the invention, wherein the compound neutralizing GM-CSF is a polypeptide, a peptidomimetic, a nucleic acid, or a small molecule.

In a preferred embodiment, the compound neutralizing GM-CSF (which is preferably a polypeptide and more preferably an antibody or a functional fragment thereof) binds or specifically binds to GM-CSF or to the GM-CSF receptor. It is envisaged that the GM-CSF or GM-CSF receptor is of an animal, including but not limited to mammals such as laboratory animals (rodents such as rats, guinea-pigs, hamsters or mice, non-human primates such as cynomolgus or macaque monkey), domestic or pet animals (e.g., dogs or cats), farm or agricultural animals (e.g., bovine, ovine, caprine and porcine animals) and/or human. Preferably, the GM-CSF or GM-CSF receptor is human GM-CSF (*Homo sapiens*) or human GM-CSF receptor, respectively, or non-human primate GM-CSF or non-human primate GM-CSF receptor, respectively. Especially preferred variants (homologs) of non-human primate GM-CSF or non-human primate GM-CSF receptor include those of gibbon monkey (nomascus *concolor*, also known as the western black crested gibbon) and of monkeys of the *macaca* family, for example rhesus monkey (*Macaca mulatta*) and cynomolgous monkey (*Macaca fascicularis*). According to a particularly preferred embodiment of the invention, the compound binding to GM-CSF or to the GM-CSF receptor (preferably the antibody or fragment thereof) exhibits cross reactivity between both human and at least one of the monkey species mentioned above. For example, an antibody or fragment thereof is capable of binding to (and neutralizing) both the human GM-CSF and the GM-CSF of the cynomolgus monkey (*Macaca fascicularis*). This is especially advantageous for an antibody molecule which is intended for therapeutic administration in human subjects, since such an antibody will normally have to proceed through a multitude of tests prior to regulatory approval, of which certain early tests involve non-human animal species. In performing such tests, it is generally desirable to use as a non-human species a species bearing a high degree of genetic similarity to humans (e.g., non-human primates such as cynomolgus monkey), since the results so obtained will generally be highly predictive of corresponding results which may be expected when administering the same molecule to humans. However, such predictive power based on animal tests depends at least partially on the comparability of the molecule, and is very high when, due to a cross-species reactivity, the same therapeutic molecule may be administered to humans and animal models. As in this embodiment of the invention, when an antibody molecule is cross reactive for the same antigen in humans and in another closely related species, tests may be performed using the same antibody molecule in humans and in this closely related species, for example in one of the monkey species mentioned above. This increases both the efficiency of the tests themselves as well as predictive power provided by such tests regarding the behavior of such antibodies in humans, the ultimate species of interest from a therapeutic standpoint. It is preferred that the antibody or a functional fragment thereof binding to GM-CSF or to the GM-CSF receptor is a monoclonal antibody or a functional fragment thereof. The same holds true for alternative embodiments with compounds neutralizing GM-CSF, which are not antibodies or not antibody derived.

Preferably the compound neutralizing GM-CSF is a human monoclonal antibody or a functional fragment thereof.

The compound neutralizing GM-CSF may be an antibody or a functional fragment thereof that binds to an epitope of human and non-human primate GM-CSF. This epitope preferably comprises amino acids 23-27 (RRLLN) and/or amino acids 65-77 (GLR/QGSLTKLKGPL). The variability at position 67 within the amino acid sequence stretch 65-77 reflects the heterogeneity in this portion of GM-CSF between, on the one hand, human and gibbon GM-CSF (in which position 67 is R) and, on the other hand, monkeys of the *macaca* family, for example cynomolgous and rhesus monkeys (in which position 67 is Q). If the epitope comprises two amino acid sequence stretches which are non-adjacent, such as 23-27 (RRLLN) and 65-77 (GLR/QGSLTKLKGPL), the epitope can also be called a "discontinuous" epitope. Said GM-CSF epitope or said GM-CSF discontinuous epitope may further comprise amino acids 28-31 (LSRD), amino acids 32-33 (TA), and/or amino acids 21-22 (EA).

The human monoclonal antibody or the functional fragment thereof preferably comprises in its heavy chain variable region a CDR3 comprising an amino acid sequence selected from the group consisting of those set out in SEQ ID NOs: 1-13 and 56; preferably the heavy chain variable region CDR3 comprises the amino acid sequence set out in SEQ ID NO:2.

Any of said heavy chain variable region CDR3 sequences can further exist together in a heavy chain variable region with the heavy chain variable region CDR1 comprising the amino acid sequence set out in SEQ ID NO:14 and the heavy chain variable region CDR2 comprising the amino acid sequence set out in SEQ ID NO:15.

Further, the human monoclonal antibody or the functional fragment thereof can comprise in its light chain variable region a CDR1 comprising the amino acid sequence set out in SEQ ID NO:16, a CDR2 comprising the amino acid sequence set out in SEQ ID NO:17, and a CDR3 comprising the amino acid sequence set out in SEQ ID NO:18.

In a especially preferred aspect of the invention, the human monoclonal antibody or the functional fragment thereof comprises in its light chain variable region a CDR1 comprising an amino acid sequence as set out in SEQ ID NO:16, a CDR2 comprising an amino acid sequence as set out in SEQ ID NO:17 and a CDR3 comprising an amino acid sequence as set out in SEQ ID NO:18, and in its heavy chain variable region a CDR1 comprising an amino acid sequence as set out in SEQ ID NO:14, a CDR2 comprising an amino acid sequence as set out in SEQ ID NO:15 and a CDR3 comprising an amino acid sequence selected from the group consisting of those set out in SEQ ID NOs:1-13 and 56, most preferably SEQ ID NO:2.

According to a preferred embodiment, the human monoclonal antibody or functional fragment thereof comprises in its light chain variable region an amino acid sequence selected from the group consisting of those set out in SEQ ID NOs:19, 54 and 55. According to another preferred embodiment, the human monoclonal antibody or functional fragment thereof comprises in its heavy chain variable region an amino acid sequence selected from the group consisting of those set out in SEQ ID NOs:20-33, 52 and 53. The human monoclonal antibody or the functional fragment thereof may in a further embodiment comprise a light chain amino acid sequence as set out in SEQ ID NO:34 and/or a heavy chain amino acid sequence selected from the group consisting of those set out in any of SEQ ID NOs:35-48, most preferably SEQ ID NO:35.

The human monoclonal antibody or the functional fragment thereof can comprise one or more amino acid sequences bearing at least 70%, 80%, 90%, 95%, 98% or 99% homology to the respective amino acid sequence as set out in any of SEQ ID NOs:1-48 and 52-56, preferably to the respective amino acid sequence as set out in any of SEQ ID NOs:1-18 and 56 and/or to the amino acid sequence of the framework regions (FRs) within the amino acid sequence as set out in any of SEQ ID NOs:19-48 and 52-55. Thus, in a preferred embodiment the human monoclonal antibody or the functional fragment thereof can comprise one or more amino acid sequences bearing at least 70%, 80%, 90%, 95%, 98% or 99% homology to the respective amino acid sequence as set out in any of SEQ ID NOs:1-18 and 56.

Alternatively, in any one of the amino acid sequences of a CDR set out in any of SEQ ID NOs:1-18 and 56 one, two, three four, five, six, seven, eight, nine, or 10 amino acids may be substituted. Preferably, such a CDR having substitutions is still capable of binding to GM-CSF as described herein.

In the alternative or in addition to, it is preferred that the human monoclonal antibody or the functional fragment thereof can comprise one or more amino acid sequences bearing at least 70%, 80%, 90%, 95%, 98% or 99% homology to the respective amino acid sequence of a VH, VL, H or L region, respectively, as set out in any of SEQ ID NOs:19-48 and 52-55. Preferably, the homology is over the entire VH, VL, H or L amino acid sequence. More preferably, the homology is within the CDRs as described before or the homology is within the FRs (or non-CDRs) of such a VH, VL, H or L region as set out in any of SEQ ID NOs:19-48 and 52-55. Accordingly, 1, 2, 3, 4, 5, 6, 7, 8, 9, 10, 11, 12, 13, 14, 15, 16, 17, 18, 19, 20, or 25 amino acids may be substituted in each of the FRs. Such a FR substitution variant is still capable of binding to GM-CSF as described herein.

The skilled person can easily identify the FRs (or non-CDRs) within SEQ ID NOs:19-48 and 52-55, since SEQ ID NOs:1-18 and 56 show CDR sequences comprised in one or more of the VH, VL, H or L sequences shown in SEQ ID NOs:19-48 and 52-55. Namely, the sequence listing provides in sequence identifier <223> the designation of each of the amino acid sequences. Identical designations indicate that these amino acid sequences "belong" together, meaning that a CDR is contained in a VH, VL, H, or L region, e.g., SEQ ID NOs:16, 17, 18 are amino acid sequences of CDRs that are contained in the amino acid sequence shown in SEQ ID NO:19 (since all of them are designated "5-306").

By way of further illustration, if amino acids are substituted in one or more or all of the CDRs or FRs of the heavy and/or light chain, it is preferred that the then-obtained "substituted" sequence is at least 70%, more preferably 80%, even more preferably 90%, particularly preferable 95%, more particularly preferable 98% or 99% identical to the "original" CDR or FR sequence. This means that it is dependent on the length of the CDR or FR to which degree it is homologous to the "substituted" sequence.

Homology is determined by standard sequence alignment programs such as Vector NTI (InforMax™, Maryland, USA) or, more preferably by the program BLASTP, preferably version blastp 2.2.5 (Nov. 16, 2002; cf. Altschul, S. F. et al. (1997) Nucl. Acids Res. 25, 3389-3402). The percentage of homology is based on the alignment of the entire polypeptide sequences (matrix: BLOSUM 62; gap costs: 11.1; cutoff value set to $10^{-3}$) using any one of the CDR, VH, VL, H or L amino acid sequence as reference in a pairwise comparison. It is calculated as the percentage of numbers of "positives" (homologous amino acids) indicated as result in the BLASTP program output divided by the total number of amino acids selected by the program for the alignment.

When used herein, homology of amino acid or nucleotide sequences may be used interchangeably with the term "identity". The term "homology" is used in the present invention means the percentage of pair-wise identical residues—following homology alignment of a sequence of an amino acid sequence or nucleotide sequence of the present invention with a sequence in question—with respect to the number of residues in the longer of these two sequences. As described above, programs for determining homology (or identity) compare aligned sequences on an amino acid-by-amino acid basis, and can be set to various levels of stringency for the comparison (e.g., identical amino acid, conservative amino acid substitution, etc.). As the term is used herein, two amino acids in question are considered as being "conservative substitutions" of one another if they each belong to the same chemical class, i.e., acidic, nonpolar/hydrophobic, uncharged polar and basic. By way of non-limiting example, two different amino acids belonging to the class of non-polar amino acids would be considered "conservative substitutions" of one another, even if these two amino acids were not identical, whereas a nonpolar amino acid on the one hand and a basic amino acid on the other hand would not be considered "conservative substitutions" of one another. Panel 3.1 of "Molecular Biology of the Cell", 4th Edition (2002), by Alberts, Johnson, Lewis, Raff, Roberts and Walter groups amino acids into four main groups: acidic, nonpolar, uncharged polar and basic. Such a grouping may be used for the purposes of determining, in the context of the present invention, whether or not a particular amino acid is a conservative substitution of another amino acid in question. The above mentioned main groups can further be sub-classified into e.g., small non-polar and large non-polar amino acids, large aromatic amino acids etc. The term "conservative amino acid substitution" also indicates any amino acid substitution for a given amino acid residue, where the substitute residue is so chemically similar to that of the given residue that no substantial decrease in polypeptide function (e.g., binding) results.

The compound neutralizing GM-CSF is typically formulated as a pharmaceutical composition for parenteral, e.g., intravenous, intra-peritoneal, subcutaneous, intramuscular, topical or intradermal administration to a subject, whereby subcutaneous administration is preferred. In certain embodiments, the pharmaceutical composition is a liquid composition, preferably an aqueous composition.

In one embodiment, the concentration of the compound neutralizing GM-CSF in the liquid pharmaceutical composition is at least 20 mg/ml, preferably at least 50 mg/ml, more preferably at least 100 mg/ml, even more preferably between about 100 mg/ml and about 200 mg/ml, such as about 150 mg/ml. In some embodiments, e.g., when the composition is intended for subcutaneous delivery, higher concentrations of the compound neutralizing GM-CSF can be used.

As noted above, the compositions of the present invention comprise a buffer. As used herein, the term "buffer" refers to an added composition that allows a liquid formulation to resist changes in pH. In certain embodiments, the added buffer allows a liquid formulation to resist changes in pH by the action of its acid-base conjugate components. Examples of suitable buffers include, but are not limited to, a buffered histidine, acetate or citrate system.

The term "specifically binds" or related expressions such as "specific binding", "binding specifically", "specific binder" etc. as used herein refer to the ability of the GM-CSF-neutralizing compound and preferably the (human) (monoclonal) antibody or functional fragment thereof to discriminate between its target (e.g., GM-CSF or the GM-CSF receptor) and any other potential antigen different from GM-CSF or the GM-CSF receptor to such an extent that, from a plurality of different antigens as potential binding partners, only GM-CSF/the GM-CSF receptor is bound, or is significantly bound. Within the meaning of the invention, a target is "significantly" bound when, from among a plurality of equally accessible different antigens as potential binding partners, the target is bound at least 10-fold, preferably at least 50-fold, most preferably at least 100-fold or greater more frequently (in a kinetic sense) than any other antigen different from the target. Such kinetic measurements can be performed e.g., using SPR technology such as a Biacore instrument. As used herein, the terms "(specifically) binding to" or related terms such as "(specifically) recognizing", "directed to", "(specifically) interacting with" and "(specifically) reacting with" mean in accordance with this invention that a compound neutralizing GM-CSF (e.g., an antibody) exhibits appreciable affinity for its target (e.g., GM-CSF or the GM-CSF receptor) and, generally, does not exhibit significant reactivity with proteins or antigens other than the aforementioned targets. "Appreciable affinity" includes binding with an affinity of about $10^{-6}$ M (KD) or stronger, such as $10^{-7}$M or stronger. Preferably, binding is considered specific when binding affinity is about $10^{-11}$ to $10^{-8}$ M, preferably of about $10^{-11}$ to $10^{-9}$ M, more preferably of about $10^{-11}$ to $10^{-10}$ M. Whether a compound (e.g., an antibody) specifically reacts with or binds to a target can be tested readily by, inter alia, comparing the reaction of said compound with its target protein or antigen with the reaction of said compound with proteins or antigens other than its target. Preferably, a compound according to the invention does not essentially bind or is not capable of binding to proteins or antigens other than GM-CSF or the GM-CSF receptor. The term "does not essentially bind" or "is not capable of binding" means that the compounds of the present invention do not show reactivity of more than 30%, preferably more than 20%, more preferably more than 10%, particularly preferably more than 9%, 8%, 7%, 6% or 5% with proteins or antigens other than GM-CSF or the GM-CSF receptor.

As used herein, "neutralization", "neutralizer", "neutralizing" and grammatically related variants thereof refer to partial or complete attenuation of the biological effect(s) of GM-CSF. Such partial or complete attenuation of the biological effect(s) of GM-CSF results from modification, interruption and/or abrogation of GM-CSF-mediated processes such as signal transduction, as manifested, for example, in intracellular signalling, cellular proliferation or release of soluble substances, up- or down-regulation of intracellular gene activation, that results e.g., in expression of surface receptors for ligands other than GM-CSF. As one of skill in the art understands, there exist multiple modes of determining whether a compound, for example an antibody or functional fragment thereof, is to be classified as a neutralizer. As an example, this may be accomplished by a standard in vitro test performed generally as follows: In a first proliferation experiment, a cell line, the degree of proliferation of which is known to depend on the activity of GM-CSF, is incubated with a series of samples with varying concentrations of GM-CSF, following which incubation the degree of proliferation of the cell line is measured. From this measurement, the concentration of GM-CSF allowing half-maximal proliferation of the cells is determined. A second proliferation experiment is then performed employing in each of the series of samples the same number of cells as used in the first proliferation experiment, the above-determined concentration of GM-CSF and, this time, varying concentrations of the compound suspected of being a neutralizer of GM-CSF. Cell proliferation is again measured to determine the concentration of the analyzed compound which is sufficient to cause half-maximal growth inhibition. If the resulting graph of growth inhibition vs. concentration of the analyzed compound is sigmoidal in shape, resulting in decreased cell proliferation with increasing concentration of the analyzed compound, then some degree of growth inhibition has been effected, i.e., the activity of GM-CSF has been neutralized to some extent. In such a case, the compound in question may be considered a "neutralizer" in the sense of the present invention. One example of a cell line, the degree of proliferation of which is known to depend on the activity of GM-CSF, is the TF-1 cell line, as described in Kitamura, T. et al. (1989), J Cell Physiol 140, 323-34.

As one of ordinary skill in the art understands, the degree of cellular proliferation is not the only parameter by which the GM-CSF neutralizing capacity may be established. For example, measurement of the level of signaling molecules (e.g., cytokines), the level of secretion of which depends on GM-CSF, may be used to identify a suspected GM-CSF neutralizer/GM-CSF inhibiting compound).

Other examples of cell lines which can be used to determine whether a compound in question, such as an antibody or functional fragment thereof, is a neutralizer of GM-CSF activity, include AML-193 (Lange, B. et al. (1987), Blood 70, 192-9); GF-D8 (Rambaldi, A. et al. (1993), Blood 81, 1376-83); GM/SO (Oez, S. et al. (1990), Experimental Hematology 18, 1108-11); MOTE (Avanzi, G. C. et al. (1990), Journal of Cellular Physiology 145, 458-64); TALL-103 (Valtieri, M. et al. (1987), Journal of Immunology 138, 4042-50); and UT-7 (Komatsu, N. et al. (1991), Cancer Research 51, 341-8).

It is understood that neutralization of GM-CSF, in line with the present invention, can be effected either outside the cells bearing GM-CSF receptors or inside said cells. Thus, the neutralization of GM-CSF by a compound can either be an inhibition or prevention of the binding of GM-CSF to its specific receptor or an inhibition of the intracellular signal induced by a binding of the cytokines to their receptors. A compound neutralizing GM-CSF may e.g., bind to GM-CSF directly or to the GM-CSF receptor, thereby interfering in both cases with the biological effects of GM-CSF.

As defined herein above, inhibitors of GM-CSF can be selected from the group consisting of a polypeptide, a peptidomimetic, a nucleic acid molecule, and a small molecule.

The term "polypeptide" as used herein describes a group of molecules, which usually consist of at least 30 amino acids coupled to each other via a covalent peptide bond. In accordance with the invention, the group of polypeptides comprises "proteins" consisting of a single polypeptide or more than one polypeptide. The term "polypeptide" also describes fragments of proteins as long as these fragments consist of at least 30 amino acids. It is well known in the art that polypeptides may form multimers such as dimers, trimers and higher oligomers, i.e., consisting of more than one polypeptide molecule. Such multimers are also included in the definition of the term "polypeptide". Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "polypeptide" and "protein" also refer to naturally or non-naturally modified polypeptides/proteins wherein the modification is effected e.g., by post-translational modifications like glycosylation, acetylation, phosphorylation, formation of disulfide bridges and the like or by chemical modifications such as PEGylation. Such modifications are well known in the art.

The term "nucleic acid" or "polynucleotide" defines in the context of the invention polymeric macromolecules consisting of multiple repeat units of phosphoric acid, sugar and purine and pyrimidine bases. Embodiments of these molecules include DNA, RNA and PNA. The nucleic acid can be single-stranded or double-stranded, linear or circular. A particularly preferred embodiment of a nucleic acid in the context of the invention is an aptamer. Nucleic acid aptamers are DNA or RNA molecules that have been selected from random pools based on their ability to bind other molecules. Aptamers have been selected which bind nucleic acid, proteins, small organic compounds, and even entire organisms. They consist of usually short strands of oligonucleotides, typically 50 bases or less.

The term "small molecule" defines a group of organic drug compounds having a molecular weight of less than 1000 Daltons, preferably up to 800 Daltons, and more preferably of 300 to 700 Daltons. The upper molecular weight limit for a small molecule allows for the possibility to rapidly diffuse across cell membranes so that they can reach intracellular sites of action. Corresponding small molecules can be derived from an at least partially randomized peptide library. Libraries of small molecules suitable according to the present invention are well known in the art and/or can be purchased from commercial distributors.

The term "peptidomimetic" describes a small protein-like chain designed to mimic a peptide. This type of molecule is artificially derived by modifying an existing peptide in order to alter the molecule's properties. For example, the parent existing peptide is modified to change the molecule's stability or biological activity. These modifications comprise the alteration of the backbone and the incorporation of nonnatural amino acids.

The term "GM-CSF receptor" refers to the physiological cell surface receptor of GM-CSF, which is described in the art as a heteromer of an alpha-chain (CD116) and a common beta (beta-c) subunit.

A preferred embodiment of a neutralizing polypeptide is an antibody or functional fragments thereof, more preferably a human antibody or functional fragments thereof. Techniques for the production of antibodies are well known in the art and described, e.g., in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

The definition of the term "antibody" includes embodiments such as monoclonal, chimeric, single chain, humanized and human antibodies. In addition to full-length antibodies, the definition also includes antibody derivatives and antibody fragments, like, inter alia, Fab fragments. Antibody fragments or derivatives further comprise F(ab')$_2$, Fv, scFv fragments or single domain antibodies such as domain antibodies or nanobodies, single variable domain antibodies or immunoglobulin single variable domain comprising merely one variable domain, which might be VHH, VH or VL, that specifically bind an antigen or epitope independently of other V regions or domains; see, for example, Harlow and Lane (1988) and (1999), loc. cit.; Kontermann and Dübel, Antibody Engineering, Springer, 2nd ed. 2010 and Little, Recombinant Antibodies for Immunotherapy, Cambridge University Press 2009. Said term also includes diabodies or Dual-Affinity Re-Targeting (DART) antibodies. Further envisaged are (bispecific) single chain diabody, tandem diabody (Tandab), "minibodies" exemplified by a structure which is as follows: (VH-VL-CH3)$_2$, (scFv-CH3)$_2$ or (scFv-CH3-scFv)$_2$, "Fc DART" and "IgG DART", multibodies such as triabodies. Immunoglobulin single variable domains encompass not only an isolated antibody single variable domain polypeptide, but also larger polypeptides that comprise one or more monomers of an antibody single variable domain polypeptide sequence.

Furthermore, the term "antibody" as employed herein also relates to derivatives or variants of the antibodies described herein which display the same specificity as the described antibodies. Examples of "antibody variants" include humanized variants of non-human antibodies, "affinity matured" antibodies (see, e.g., Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dübel (2010), loc. cit. and Little (2009), loc. cit.).

The term "antibody" also comprises immunoglobulins (Ig's) of different classes (i.e., IgA, IgG, IgM, IgD and IgE) and subclasses (such as IgG1, IgG2 etc.). Derivatives of antibodies, which also fall under the definition of the term antibody in the meaning of the invention, include modifications of such molecules as for example glycosylation, acetylation, phosphorylation, disulfide bond formation, farnesylation, hydroxylation, methylation or esterification.

A functional fragment of an antibody includes the domain of a F(ab')$_2$ fragment, a Fab fragment, scFv or constructs comprising single immunoglobulin variable domains or single domain antibody polypeptides, e.g., single heavy chain variable domains or single light chain variable domains as well as other antibody fragments as described herein above. The F(ab')$_2$ or Fab may be engineered to minimize or completely remove the intermolecular disulphide interactions that occur between the $C_{H1}$ and $C_L$ domains.

The term "human" antibody as used herein is to be understood as meaning that the antibody or its functional fragment, comprises (an) amino acid sequence(s) contained in the human germline antibody repertoire. For the purposes of definition herein, an antibody, or its fragment, may therefore be considered human if it consists of such (a) human germline amino acid sequence(s), i.e., if the amino acid sequence(s) of the antibody in question or functional fragment thereof is (are) identical to (an) expressed human germline amino acid sequence(s). An antibody or functional fragment thereof may also be regarded as human if it consists of (a) sequence(s) that deviate(s) from its (their) closest human germline sequence(s) by no more than would be expected due to the imprint of somatic hypermutation. Additionally, the antibodies of many non-human mammals, for example rodents such as mice and rats, comprise VH CDR3 amino acid sequences which one may expect to exist in the expressed human antibody repertoire as well. Any such sequence(s) of human or nonhuman origin which may be expected to exist in the expressed human repertoire would also be considered "human" for the purposes of the present invention. The term "human antibody" hence includes antibodies having variable and constant regions corresponding substantially to human germline immunoglobulin sequences known in the art, including, for example, those described by Kabat et al. (See Kabat et al. (1991) loc. cit.). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The non-human and human antibodies or functional fragments thereof are preferably monoclonal. It is particularly difficult to prepare human antibodies which are monoclonal. In contrast to fusions of murine B cells with immortalized cell lines, fusions of human B cells with immortalized cell lines are not viable. Thus, the human monoclonal antibodies are the result of overcoming significant technical hurdles generally acknowledged to exist in the field of antibody technology. The monoclonal nature of the antibodies makes them particularly well suited for use as therapeutic agents, since such antibodies will exist as a single, homogeneous molecular species which can be well-characterized and reproducibly made and purified. These factors result in products whose biological activities can be predicted with a high level of precision, very important if such molecules are going to gain regulatory approval for therapeutic administration in humans. The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

It is especially preferred that the monoclonal antibodies or corresponding functional fragments be human antibodies or corresponding functional fragments. In contemplating antibody agents intended for therapeutic administration to humans, it is highly advantageous that the antibodies are of human origin. Following administration to a human patient, a human antibody or functional fragment thereof will most probably not elicit a strong immunogenic response by the patient's immune system, i.e., will not be recognized as being a foreign that is non-human protein. This means that no host, i.e., patient, antibodies will be generated against the therapeutic antibody which would otherwise block the therapeutic antibody's activity and/or accelerate the therapeutic antibody's elimination from the body of the patient, thus preventing it from exerting its desired therapeutic effect.

According to a preferred embodiment of the invention, the human monoclonal antibody or functional fragment thereof to be utilized for pharmaceutical purposes exhibits reactivity between both human and at least one monkey species. The same cross-species reactivity is also preferred for all other non-antibody or non-antibody derived neutralizing/inhibiting compounds of GM-CSF.

According to a further embodiment of the invention, the antibody may be an IgG antibody. An IgG isotype comprises not only the variable antibody regions of the heavy and light chains responsible for the highly discriminative antigen recognition and binding, but also the constant regions of the heavy and light antibody polypeptide chains normally present in "naturally" produced antibodies and, in some cases, even modification at one or more sites with carbohydrates. Such glycosylation is generally a hallmark of the IgG format, and located in the constant regions comprising the so called Fc region of a full antibody which is known to elicit various effector functions in vivo. In addition, the Fc region mediates binding of IgG to Fc receptor, as well as facilitating homing of the IgG to locations with increased Fc receptor presence—inflamed tissue, for example. Advantageously, the IgG antibody is an IgG1 antibody or an IgG4 antibody, formats which are preferred since their mechanism of action in vivo is particularly well understood and characterized. This is especially the case for IgG1 antibodies.

According to a further embodiment of the invention, the functional fragment of the antibody may preferably be an scFv, a single domain antibody, an Fv, a VHH antibody, a diabody, a tandem diabody, a Fab, a Fab' or a F(ab)2. These formats may generally be divided into two subclasses, namely those which consist of a single polypeptide chain, and those which comprise at least two polypeptide chains. Members of the former subclass include a scFv (comprising one VH region and one VL region joined into a single polypeptide chain via a polypeptide linker); a single domain antibody (comprising a single antibody variable region) such as a VHH antibody (comprising a single VH region). Members of the latter subclass include an Fv (comprising one VH region and one VL region as separate polypeptide chains which are non-covalently associated with one another); a diabody (comprising two non-covalently associated polypeptide chains, each of which comprises two antibody variable regions—normally one VH and one VL per polypeptide chain—the two polypeptide chains being arranged in a head-to-tail conformation so that a bivalent antibody molecule results); a tandem diabody (bispecific single-chain Fv antibodies comprising four covalently linked immunoglobulin variable—VH and VL—regions of two different specificities, forming a homodimer that is twice as large as the diabody described above); a Fab (comprising as one polypeptide chain an entire antibody light chain, itself comprising a VL region and the entire light chain constant region and, as another polypeptide chain, a part of an antibody heavy chain comprising a complete VH region and part of the heavy chain constant region, said two polypeptide chains being intermolecularly connected via an interchain disulfide bond); a Fab5 (as a Fab, above, except with additional reduced disulfide bonds comprised on the antibody heavy chain); and a F(ab)2 (comprising two Fab' molecules, each Fab' molecule being linked to the respective other Fab' molecule via interchain disulfide bonds). In general, functional antibody fragments of the type described hereinabove allow great flexibility in tailoring, for example, the pharmacokinetic properties of an antibody desired for therapeutic administration to the particular exigencies at hand. For example, it may be desirable to reduce the size of the antibody administered in order to increase the degree of tissue penetration when treating tissues known to be poorly vascularized (for example, joints). Under some circumstances, it may also be desirable to increase the rate at which the therapeutic antibody is eliminated from the body, said rate generally being accelerable by decreasing the size of the antibody administered. An antibody fragment is defined as a functional antibody fragment in the context of the invention as long as the fragment maintains the specific binding characteristics for the epitope/target of the parent antibody, i.e., as long as it specifically binds to GM-CSF or to the GM-CSF receptor.

According to a further embodiment of the invention, said antibody or functional fragment thereof may be present in monovalent monospecific; multivalent monospecific, in particular bivalent monospecific; or multivalent multispecific, in particular bivalent bispecific forms. In general, a multivalent monospecific, in particular bivalent monospecific antibody such as a full human IgG as described hereinabove may bring with it the therapeutic advantage that the neutralization effected by such an antibody is potentiated by avidity effects, i.e., binding by the same antibody to multiple molecules of the same antigen, here GM-CSF or the GM-CSF receptor. Several monovalent monospecific forms of fragments of antibodies have been described above (for example, a scFv, an Fv, a VHH or a single domain antibody). Multivalent multi-specific, in particular bivalent bi-specific forms of an antibody may include a full IgG in which one binding arm binds to primate GM-CSF/the GM-CSF receptor, while the other binding arm of which binds to another antigen different from GM-CSF/the GM-CSF receptor. A further multivalent multi-specific, in particular bivalent bi-specific form may advantageously be a human single chain bi-specific antibody, i.e., a recombinant human antibody construct comprising two scFv entities as described above, connected into one contiguous polypeptide chain by a short interposed polypeptide spacer as generally known in the art (see for example WO 99/54440 for an anti-CD19×anti-CD3 bi-specific single chain antibody). Here, one scFv portion of the bi-specific single chain antibody comprised within the bispecific single chain antibody will specifically bind GM-CSF/the GM-CSF receptor as set out above, while the respective other scFv portion of this bi-specific single chain antibody will bind another antigen determined to be of therapeutic benefit.

According to a further embodiment the antibodies or functional fragments thereof may be derivatized, for example with an organic polymer, for example with one or more molecules of polyethylene glycol ("PEG") and/or polyvinyl pyrrolidone ("PVP"). As is known in the art, such derivatization can be advantageous in modulating the pharmacodynamic properties of antibodies or functional fragments thereof. Especially preferred are PEG molecules derivatized as PEG-maleimide, enabling conjugation with the antibody or functional fragment thereof in a site-specific manner via the sulfhydryl group of a cysteine amino acid. Of these, especially preferred are 20 kD and/or 40 kD PEG-maleimide, in either branched or straight-chain form. It may be especially advantageous to increase the effective molecular weight of smaller human anti-GM-CSF antibody fragments such as scFv fragments by coupling the latter to one or more molecules of PEG, especially PEG-maleimide.

The antibodies of the present invention also include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include "primitized" antibodies comprising variable domain antigen-binding sequences derived from a non-human primate (e.g., Old World Monkey, Ape etc.) and human constant region sequences.

"Humanized" forms of non-human (e.g., murine) antibodies are chimeric immunoglobulins, immunoglobulin chains or fragments thereof (such as Fv, Fab, Fab' F(ab')2 or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992).

As used herein, the numbering of the amino acid residues or positions of human and non-human primate GM-CSF refers to that of mature GM-CSF, i.e., GM-CSF without its 17 amino acid signal sequence (the total length of mature GM-CSF in both human and nonhuman primate species described above is 127 amino acids). The sequence of human GM-CSF and gibbon GM-CSF is as follows:

SEQ ID NO: 49

APARSPSPST QPWEHVNAIQ EARRLLN*LSR D*TAAEMNETV

EVISEMFDLQ EPTCLQTRLE LYKQGLRGSL TKLKGPLTMM

ASHYKQHCPP TPETSCATQI ITFESFKENL KDFLLVIPFD

CWEPVQE

The sequence of GM-CSF in certain members of the *macaca* monkey family such as for example rhesus monkey and cynomolgous monkey is as follows:

SEQ ID NO: 50

APARSPSPGT QPWEHVNAIQ EARRLLN*LSR D*TAAEMNKTV

EVVSEMFDLQ EPSCLQTRLE LYKQGLQGSL TKLKGPLTMM

ASHYKQHCPP TPETSCATQI ITFQSEKENL KDFLLVIPFD

CWEPVQE

The sequence of human GM-CSF is also shown in SEQ ID NO:57. That of gibbon GM-CSF is also shown in SEQ ID NO:58:

(SEQ ID NO: 57 and 58)

APARSPSPST QPWEHVNAIQ EARRLLN*LSR D*TAAEMNETV

EVISEMFDLQ EPTCLQTRLE LYKQGLRGSL TKLKGPLTMM

ASHYKQHCPP TPETSCATQI ITFESFKENL KDFLLVIPFD

CWEPVQE

The sequence of GM-CSF in certain members of the *macaca* monkey family such as for example rhesus monkey (SEQ ID NO:59) and cynomolgous monkey (SEQ ID NO:60) is also as follows:

(SEQ ID NO: 59 and 60)

APARSPSPGT QPWEHVNAIQ EARRLLN*LSR D*TAAEMNKTV

EVVSEMFDLQ EPSCLQTRLE LYKQGLQGSL TKLKGPLTMM

ASHYKQHCPP TPETSCATQI ITFQSFKENL KDFLLVIPFD

CWEPVQE

The minimum epitope, advantageously a discontinuous epitope as described herein, bound by the antibody, preferably a human monoclonal antibody (or functional fragment thereof) is indicated in the GM-CSF sequence(s) is shown above in boldface.

According to a preferred embodiment, the compound neutralizing GM-CSF is an antibody (preferably a human monoclonal antibody) or functional fragment thereof which binds to GM-CSF. More preferably, it binds to an epitope of GM-CSF which preferably comprises amino acids 23-27 (RRLLN) and/or amino acids 65-77 (GLR/QGSLTKLKGPL). These amino acid sequence stretches are indicated in the above GM-CSF sequence in boldface. The term "epitope" refers to a site on an antigen or a target (e.g., GM-CSF) to which a compound, such as an antibody or functional fragment thereof, specifically binds. Said binding/interaction is also understood to define a "specific recognition". "Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids or more in a unique sequence. In the context of the present invention, it is preferred that the GM-CSF epitope is a discontinuous epitope. In case that the antibody binds to both sequence stretches 23-27 and 65-77, the epitope can be called "discontinuous". In the secondary structure of human GM-CSF, amino acids 15-35 are situated in helix A while residues corresponding to positions 65-77 are part of a loop-structure located between helices C and D. A three-dimensional model of folding of the molecule reveals close sterical proximity of these sites with respect to one another (see also WO 2006/111353). As used herein, the term "discontinuous epitope" is to be understood as at least two non-adjacent amino acid sequence stretches within a given polypeptide chain, here mature human and non-human primate GM-CSF, which are simultaneously and specifically bound by an antibody. According to this definition, such simultaneous specific binding may be of the GM-CSF polypeptide in linear form. Here, one may imagine the mature GM-CSF polypeptide forming an extended loop, in one region of which the two sequences indicated in boldface above line up, for example more or less in parallel and in proximity of one another. In this state they are specifically and simultaneously bound by the antibody fragment. According to this definition, simultaneous specific binding of the two sequence stretches of mature GM-CSF indicated above may also take the form of antibody binding to a conformational epitope. Here, mature GM-CSF has already formed its tertiary conformation as it normally exists in vivo. In this tertiary conformation, the polypeptide chain of mature GM-CSF is folded in such a manner as to bring the two sequence stretches indicated above into spatial proximity, for example on the outer surface of a particular region of mature, folded GM-CSF, where they are then recognized by virtue of their three-dimensional conformation in the context of the surrounding polypeptide sequences.

In a further preferred embodiment, the above epitope or the above discontinuous epitope of GM-CSF further comprises:
    amino acids 28-31 (LSRD), italicized in the above sequences of human and nonhuman primate GM-CSF;
    amino acids 32-33 (TA), underlined in the above sequences of human and nonhuman primate GM-CSF; and/or
    amino acids 21-22 (EA), underlined in the above sequences of human and nonhuman primate GM-CSF.

Preferred human monoclonal anti-GM-CSF antibodies or functional fragments thereof are those as disclosed specifically in WO2006/111353 under the referenced SEQ ID NOs 1 to 48 and 52 to 56, depicting amino acid sequences of heavy and light chain complementary determining regions (CDRs) 1-3 as well as variable regions of heavy and light chains and full length heavy and light chains.

Especially preferred are anti-GM-CSF antibodies or functional fragments thereof comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:1; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:2; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:3; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:4; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:5; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:6; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:7; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:8; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:9; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:10; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:11; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:12; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:13; or comprising a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:56.

Still more preferred, any of the above 14 combinations of heavy chain CDR1, CDR2 and CDR3 sequences exists in an antibody or functional fragment thereof further comprising in its light chain variable region a CDR1 comprising the amino acid sequence set out in SEQ ID NO:16, a CDR2 comprising the amino acid sequence set out in SEQ ID NO:17, and a CDR3 comprising the amino acid sequence set out in SEQ ID NO:18.

An especially preferred anti-GM-CSF antibody or functional fragment thereof comprises a heavy chain variable region CDR1 sequence as set out in SEQ ID NO:14, a heavy chain variable region CDR2 sequence as set out in SEQ ID NO:15 and a heavy chain variable region CDR3 sequence as set out in SEQ ID NO:2 and further comprises in its light chain variable region a CDR1 comprising the amino acid sequence set out in SEQ ID NO:16, a CDR2 comprising the amino acid sequence set out in SEQ ID NO:17, and a CDR3 comprising the amino acid sequence set out in SEQ ID NO:18. This anti-GM-CSF antibody is a most preferred compound for neutralizing GM-CSF and is also described in WO 2006/111353.

According to a further embodiment, the anti-GM-CSF antibody or functional fragment thereof comprises in its light chain variable region an amino acid sequence as set out in SEQ ID NO:19. Preferred is an antibody or functional fragment thereof, the light chain variable region comprising an amino acid sequence as set out in SEQ ID NO:19 and a heavy chain variable region comprising an amino acid sequence as set out in SEQ ID NO:20; or an antibody or functional fragment thereof, the light chain variable region comprising an amino acid sequence as set out in SEQ ID NO:19 and a heavy chain variable region comprising an amino acid sequence as set out in SEQ ID NO:21; or an antibody or functional fragment thereof, the light chain variable region comprising an amino acid sequence as set out in SEQ ID NO:19 and a heavy chain variable region comprising an amino acid sequence as set out in SEQ ID NO:22; or an antibody or functional fragment thereof, the light chain variable region comprising an amino acid sequence as set out in SEQ ID NO:19 and a heavy chain variable region comprising an amino acid sequence as set out in SEQ ID NO:23; or an antibody or functional fragment thereof, the light chain variable region comprising an amino acid sequence as set out in SEQ ID NO:19 and a heavy chain variable region comprising an amino acid sequence as set out in SEQ ID NO:24; or an antibody or functional fragment thereof, the light chain variable region comprising an amino acid sequence as set out in SEQ ID NO:19 and a heavy chain variable region comprising an amino acid sequence as set out in SEQ ID NO:25; or an antibody or functional fragment thereof, the light chain variable region comprising an amino acid sequence as set out in SEQ ID NO:19 and a heavy chain variable region comprising an amino acid sequence as set out in SEQ ID NO:26; or an antibody or functional fragment thereof, the light chain variable region comprising an amino acid sequence as set out in SEQ ID NO:19 and a heavy chain variable region comprising an amino acid sequence as set out in SEQ ID NO:27; or an antibody or functional fragment thereof, the light chain variable region comprising an amino acid sequence as set out in SEQ ID NO:19 and a heavy chain variable region comprising an amino acid sequence as set out in SEQ ID NO:28; or an antibody or functional fragment thereof, the light chain variable region comprising an amino acid sequence as set out in SEQ ID NO:19 and a heavy chain variable region comprising an amino acid sequence as set out in SEQ ID NO:29; or an antibody or functional fragment thereof, the light chain variable region comprising an amino acid sequence as set out in SEQ ID NO:19 and a heavy chain variable region comprising an amino acid sequence as set out in SEQ ID NO:30; or an antibody or functional fragment thereof, the light chain variable region comprising an amino acid sequence as set out in SEQ ID NO:19 and a heavy chain variable region comprising an amino acid sequence as set out in SEQ ID NO:31; or an antibody or functional fragment thereof, the light chain variable region comprising an amino acid sequence as set out in SEQ ID NO:19 and a heavy chain variable region comprising an amino acid sequence as set out in SEQ ID NO:32; or an antibody or functional fragment thereof, the light chain variable region comprising an amino acid sequence as set out in SEQ ID NO:19 and a heavy chain variable region comprising an amino acid sequence as set out in SEQ ID NO:33; or an antibody or functional fragment thereof, the light chain variable region comprising an amino acid sequence as set out in SEQ ID NO:19 and a heavy chain variable region comprising an amino acid sequence as set out in SEQ ID NO:52; or an antibody or functional fragment thereof, the light chain variable region comprising an amino acid sequence as set out in SEQ ID NO:19 and a heavy chain variable region comprising an amino acid sequence as set out in SEQ ID NO:53.

According to a further embodiment, the anti-GM-CSF antibody or functional fragment thereof comprises in its light chain variable region an amino acid sequence as set out in SEQ ID NO:54. Preferred is an antibody or functional fragment thereof, the light chain variable region comprising an amino acid sequence as set out in SEQ ID NO:54 and a heavy chain variable region comprising an amino acid sequence as set out in SEQ ID NO:20; or an antibody or functional fragment thereof, the light chain variable region comprising an amino acid sequence as set out in SEQ ID NO:54 and a heavy chain variable region comprising an amino acid sequence as set out in SEQ ID NO:21; or an antibody or functional fragment thereof, the light chain variable region comprising an amino acid sequence as set out in SEQ ID NO:54 and a heavy chain variable region comprising an amino acid sequence as set out in SEQ ID NO:22; or an antibody or functional fragment thereof, the light chain variable region comprising an amino acid sequence as set out in SEQ ID NO:54 and a heavy chain variable region comprising an amino acid sequence as set out in SEQ ID NO:23; or an antibody or functional fragment thereof, the light chain variable region comprising an amino acid sequence as set out in SEQ ID NO:54 and a heavy chain variable region comprising an amino acid sequence as set out in SEQ ID NO:24; or an antibody or functional fragment thereof, the light chain variable region comprising an amino acid sequence as set out in SEQ ID NO:54 and a heavy chain variable region comprising an amino acid sequence as set out in SEQ ID NO:25; or an antibody or functional fragment thereof, the light chain variable region comprising an amino acid sequence as set out in SEQ ID NO:54 and a heavy chain variable region comprising an amino acid sequence as set out in SEQ ID NO:26; or an antibody or functional fragment thereof, the light chain variable region comprising an amino acid sequence as set out in SEQ ID NO:54 and a heavy chain variable region comprising an amino acid sequence as set out in SEQ ID NO:27; or an antibody or functional fragment thereof, the light chain variable region comprising an amino acid sequence as set out in SEQ ID NO:54 and a heavy chain variable region comprising an amino acid sequence as set out in SEQ ID NO:28; or an antibody or functional fragment thereof, the light chain variable region comprising an amino acid sequence as set out in SEQ ID NO:54 and a heavy chain variable region comprising an amino acid sequence as set out in SEQ ID NO:29; or an antibody or functional fragment thereof, the light chain variable region comprising an amino acid sequence as set out in SEQ ID NO:54 and a heavy chain variable region comprising an amino acid sequence as set out in SEQ ID NO:30; or an antibody or functional fragment thereof, the light chain variable region comprising an amino acid sequence as set out in SEQ ID NO:54 and a heavy chain variable region comprising an amino acid sequence as set out in SEQ ID NO:31; or an antibody or functional fragment thereof, the light chain variable region comprising an amino acid sequence as set out in SEQ ID NO:54 and a heavy chain variable region comprising an amino acid sequence as set out in SEQ ID NO:32; or an antibody or functional fragment thereof, the light chain variable region comprising an amino acid sequence as set out in SEQ ID NO:54 and a heavy chain variable region comprising an amino acid sequence as set out in SEQ ID NO:33; or an antibody or functional fragment thereof, the light chain variable region comprising an amino acid sequence as set out in SEQ ID NO:54 and a heavy chain variable region comprising an amino acid sequence as set out in SEQ ID NO:52; or an antibody or functional fragment thereof, the light chain variable region comprising an amino acid sequence as set out in SEQ ID NO:54 and a heavy chain variable region comprising an amino acid sequence as set out in SEQ ID NO:53.

According to a further embodiment, the anti-GM-CSF antibody or functional fragment thereof comprises in its light chain variable region an amino acid sequence as set out in SEQ ID NO:55. Preferred is an antibody or functional fragment thereof, the light chain variable region comprising an amino acid sequence as set out in SEQ ID NO:55 and a heavy chain variable region comprising an amino acid sequence as set out in SEQ ID NO:20; or an antibody or functional fragment thereof, the light chain variable region comprising an amino acid sequence as set out in SEQ ID NO:55 and a heavy chain variable region comprising an amino acid sequence as set out in SEQ ID NO:21; or an antibody or functional fragment thereof, the light chain variable region comprising an amino acid sequence as set out in SEQ ID NO:55 and a heavy chain variable region comprising an amino acid sequence as set out in SEQ ID NO:22; or an antibody or functional fragment thereof, the light chain variable region comprising an amino acid sequence as set out in SEQ ID NO:55 and a heavy chain variable region comprising an amino acid sequence as set out in SEQ ID NO:23; or an antibody or functional fragment thereof, the light chain variable region comprising an amino acid sequence as set out in SEQ ID NO:55 and a heavy chain variable region comprising an amino acid sequence as set out in SEQ ID NO:24; or an antibody or functional fragment thereof, the light chain variable region comprising an amino acid sequence as set out in SEQ ID NO:55 and a heavy chain variable region comprising an amino acid sequence as set out in SEQ ID NO:25; or an antibody or functional fragment thereof, the light chain variable region comprising an amino acid sequence as set out in SEQ ID NO:55 and a heavy chain variable region comprising an amino acid sequence as set out in SEQ ID NO:26; or an antibody or functional fragment thereof, the light chain variable region comprising an amino acid sequence as set out in SEQ ID NO:55 and a heavy chain variable region comprising an amino acid sequence as set out in SEQ ID NO:27; or an antibody or functional fragment thereof, the light chain variable region comprising an amino acid sequence as set out in SEQ ID NO:55 and a heavy chain variable region comprising an amino acid sequence as set out in SEQ ID NO:28; or an antibody or functional fragment thereof, the light chain variable region comprising an amino acid sequence as set out in SEQ ID NO:55 and a heavy chain variable region comprising an amino acid sequence as set out in SEQ ID NO:29; or an antibody or functional fragment thereof, the light chain variable region comprising an amino acid sequence as set out in SEQ ID NO:55 and a heavy chain variable region comprising an amino acid sequence as set out in SEQ ID NO:30; or an antibody or functional fragment thereof, the light chain variable region comprising an amino acid sequence as set out in SEQ ID NO:55 and a heavy chain variable region comprising an amino acid sequence as set out in SEQ ID NO:31; or an antibody or functional fragment thereof, the light chain variable region comprising an amino acid sequence as set out in SEQ ID NO:55 and a heavy chain variable region comprising an amino acid sequence as set out in SEQ ID NO:32; or an antibody or functional fragment thereof, the light chain variable region comprising an amino acid sequence as set out in SEQ ID NO:55 and a heavy chain variable region comprising an amino acid sequence as set out in SEQ ID NO:33; or an antibody or functional fragment thereof, the light chain variable region comprising an amino acid sequence as set out in SEQ ID NO:55 and a heavy chain variable region comprising an amino acid sequence as set out in SEQ ID NO:52; or an antibody or functional fragment thereof, the light chain variable region comprising an amino acid sequence as set out in SEQ ID NO:55 and a heavy chain variable region comprising an amino acid sequence as set out in SEQ ID NO:53.

A preferred anti-GM-CSF antibody or functional fragment thereof comprises in its light chain variable region a CDR1 comprising an amino acid sequence as set out in SEQ ID NO:16, a CDR2 comprising an amino acid sequence as set out in SEQ ID NO:17 and a CDR3 comprising an amino acid sequence as set out in SEQ ID NO:18 and comprises in its heavy chain variable region a CDR1 comprising an amino acid sequence as set out in SEQ ID NO:14, a CDR2 comprising an amino acid sequence as set out in SEQ ID NO:15 and a CDR3 comprising an amino acid sequence as set out in any of SEQ ID NOs:1, 2, 3, 4, 5, 6, 7, 8, 9, 10, 11, 12, 13 or 56.

In a further preferred embodiment the antibody comprises in its light chain an amino acid sequence as set out in SEQ ID NO:34 and in its heavy chain an amino acid sequence as set out in SEQ ID NO:35; or in its light chain an amino acid sequence as set out in SEQ ID NO:34 and in its heavy chain an amino acid sequence as set out in SEQ ID NO:36; or in its light chain an amino acid sequence as set out in SEQ ID NO:34 and in its heavy chain an amino acid sequence as set out in SEQ ID NO:37; or in its light chain an amino acid sequence as set out in SEQ ID NO:34 and in its heavy chain an amino acid sequence as set out in SEQ ID NO:38; or in its light chain an amino acid sequence as set out in SEQ ID NO:34 and in its heavy chain an amino acid sequence as set out in SEQ ID NO:39; or in its light chain an amino acid sequence as set out in SEQ ID NO:34 and in its heavy chain an amino acid sequence as set out in SEQ ID NO:40; or in its light chain an amino acid sequence as set out in SEQ ID NO:34 and in its heavy chain an amino acid sequence as set out in SEQ ID NO:41; or in its light chain an amino acid sequence as set out in SEQ ID NO:34 and in its heavy chain an amino acid sequence as set out in SEQ ID NO:42; or in its light chain an amino acid sequence as set out in SEQ ID NO:34 and in its heavy chain an amino acid sequence as set out in SEQ ID NO:43; or in its light chain an amino acid sequence as set out in SEQ ID NO:34 and in its heavy chain an amino acid sequence as set out in SEQ ID NO:44; or in its light chain an amino acid sequence as set out in SEQ ID NO:34 and in its heavy chain an amino acid sequence as set out in SEQ ID NO:45; or in its light chain an amino acid sequence as set out in SEQ ID NO:34 and in its heavy chain an amino acid sequence as set out in SEQ ID NO:46; or in its light chain an amino acid sequence as set out in SEQ ID NO:34 and in its heavy chain an amino acid sequence as set out in SEQ ID NO:47; or in its light chain an amino acid sequence as set out in SEQ ID NO:34 and in its heavy chain an amino acid sequence as set out in SEQ ID NO:48. The anti-GM-CSF antibody comprising in its light chain an amino acid sequence as set out in SEQ ID NO:34 and in its heavy chain an amino acid sequence as set out in SEQ ID NO:35 is a most preferred compound for neutralizing GM-CSF and is also described in WO 2006/111353.

The preferred embodiments above provide antibody molecules and/or functional fragments thereof, preferably human monoclonal antibody molecules and/or functional fragments thereof, which are especially advantageous as neutralizers of the activity of primate and human GM-CSF. Antibodies or functional fragments thereof according to these especially preferred embodiments are highly advantageous for several reasons.

First, they recognize primate and human GM-CSF with high specificity. That is to say that from a mixture of primate GM-CSF with other primate colony stimulating factors (for example primate G-CSF and M-CSF), the binding molecules according to these especially preferred embodiments are highly discriminating for primate GM-CSF, whereas the other colony stimulating factors in the same milieu are not recognized. The same applies mutatis mutandis to the human GM-CSF. This means that an antibody or functional fragment thereof according to these embodiments, when administered to a human, will be expected to specifically bind to and neutralize only the desired target, whereas other undesired targets are neither bound nor neutralized. Ultimately, this leads to a high degree of predictability concerning the therapeutic mode of action in vivo.

Second, binders according to these especially preferred embodiments bind to primate and human GM-CSF with appreciable affinity. "Appreciable affinity" includes binding with an affinity of about $10^{-6}$ M (KD) or stronger. Preferably, binding is considered appreciable (or high or specific) when binding affinity is about $10^{-12}$ to $10^{-8}$ M, $10^{-12}$ to $10^{-9}$ M, $10^{-12}$ to $10^{-10}$ M, $10^{-11}$ to $10^{-8}$M, preferably of about $10^{-11}$ to $10^{-9}$ M. Accordingly, a binder of the invention has preferably a $K_D$ within that range. Given the fact that $K_D$ values of from about $4\times10^{-9}$M down to as low as about $0.04\times10^{-9}$ M, the latter corresponding to about 40 pM, have been observed for antibody molecules described herein, it is preferred that antibody molecules of the invention have a $K_D$ within that range. However, it is also preferred that antibody molecules of the invention have a $K_D$ as described herein above. Since the kinetic on-rate of such molecules in aqueous media is largely diffusion controlled and therefore cannot be improved beyond what the local diffusion conditions will allow under physiological conditions, the low $K_D$ arises primarily as a result of the kinetic off-rate, $k_{off}$, which for the highest affinity antibody binder is approximately $10^{-5}$ $s^{-1}$. This means that once the complex between a human monoclonal antibody or functional fragment thereof according to any of these embodiments on the one hand and GM-CSF on the other hand is formed, it does not readily, or at least does not quickly separate. For binding molecules intended as neutralizers of biological activity, these characteristics are highly advantageous since the desirable neutralizing effect will normally last only as long as the molecule, the biological activity of which is to be neutralized (here primate and human GM-CSF) remains bound by the neutralizing binding molecule. So a neutralizing molecule which remains bound to its intended target for a long time will continue to neutralize for a correspondingly long time.

The high binding affinity of antibodies or functional fragments thereof to primate and human GM-CSF has an additional advantage. Normally, antibodies or functional fragments thereof will be eliminated from the bloodstream of a patient in a size-dependent fashion, with smaller molecules being excreted and eliminated before larger ones. Since the complex of the two polypeptides—antibody or antibody fragment and bound GM-CSF—is obviously larger than the antibody alone, the low $k_{off}$ mentioned above has the effect that the therapeutic neutralizer is excreted and eliminated from the patient's body more slowly than would be the case, were it not bound to GM-CSF. Thus, not only the magnitude of the neutralizing activity but also its duration in vivo is increased.

The neutralizing activity determined for binders according to the above embodiments is surprisingly high. As will be described in more detail herein below, GM-CSF-neutralizing activity was measured in vitro using a TF-1 growth inhibition assay (Kitamura, T. et al. (1989), J. Cell Physiol. 140, 323-34). As an indication of neutralizing potential, $IC_{50}$ values were measured, $IC_{50}$ representing the concentration of the antibody or functional fragment thereof according to any of these embodiments required to elicit a half-maximal inhibition of TF-1 cell proliferation. For the human monoclonal anti-GM-CSF antibodies or functional fragments thereof specified above an $IC_{50}$ value of approximately $3\times10^{-10}$ M, or about 0.3 nM was determined. The binding molecules are therefore highly potent neutralizers of the activity of primate and human GM-CSF.

Other examples of neutralizing anti-GM-CSF antibodies are the human E10 antibody and human G9 antibody described in Li et al. (2006) PNAS 103(10):3557-3562. E10 and G9 are IgG class antibodies. E10 has an 870 pM binding affinity for GM-CSF and G9 has a 14 pM affinity for GM-CSF. Both antibodies are specific for binding to human GM-CSF and show strong neutralizing activity as assessed with a TF-1 cell proliferation assay. Other examples are the human anti-GM-CSF antibodies as disclosed in WO 2006/122797.

GM-CSF antagonists or neutralizers that are anti-GM-CSF receptor antibodies can also be employed in the present invention. Such GM-CSF antagonists include antibodies to the GM-CSF receptor alpha chain or beta chain. An anti-GM-CSF receptor antibody employed in the invention can be in any antibody form as explained above, e.g., intact, chimeric, monoclonal, polyclonal, antibody fragment or derivative, single-chain, humanized, humaneered, and the like. Examples of anti-GM-CSF receptor antibodies, e.g., neutralizing high-affinity antibodies, suitable for use in the invention are known in the art (see e.g., U.S. Pat. No. 5,747,032 and Nicola et al., Blood 82:15 1724, 1993).

Even further sequences for suitable antibodies are provided in applications and are incorporated by reference in their entirety. Anti-GM-CSF antibodies are provided in WO2006/122797, WO2007/049472, WO2007/092939, WO2009/134805, WO2009/064399, WO2009/038760. Antibodies against the GM-CSF receptor are provided in WO2007/110631.

In summary, the anti-GM-CSF antibodies or functional fragments thereof exhibit a high degree of discrimination for the desired antigen, bind this antigen extremely tightly and for a long time and exhibit highly potent neutralizing activity for the long time they remain bound. At the same time, the long persistence of the binder-antigen complex slows elimination of this binder from the body, thereby lengthening the duration of the desired therapeutic effect in vivo. The same characteristics preferably also apply for antibodies that recognize the GM-CSF receptor, as described above.

The composition according to the present invention is preferably a pharmaceutical composition. In accordance with the present embodiments, the term "pharmaceutical composition" relates to a composition for administration to a patient, preferably a human patient. Pharmaceutical compositions or formulations are usually in such a form as to allow the biological activity of the active ingredient to be effective and may therefore be administered to a subject for therapeutic use as described herein. Usually, a pharmaceutical composition comprises suitable (i.e., pharmaceutically acceptable) formulations of carriers, stabilizers and/or excipients. In a preferred embodiment, the pharmaceutical composition is a composition for parenteral, trans-dermal, intra-luminal, intra-arterial, intra-thecal and/or intranasal administration or for direct injection into tissue. It is in particular envisaged that said composition is administered to a patient via infusion or injection. Administration of the suitable compositions may be effected by different ways, e.g., by intravenous, intra-peritoneal, subcutaneous, intramuscular, topical or intra-dermal administration. The composition of the present invention may further comprise a pharmaceutically acceptable carrier. Examples of suitable pharmaceutical carriers are well known in the art and include buffered saline solutions, water, emulsions, such as oil/water emulsions, various types of wetting agents, sterile solutions, liposomes, etc. Compositions comprising such carriers can be formulated by well-known conventional methods.

In accordance with the present embodiments, the term "effective amount" refers to an amount of the compound neutralizing GM-CSF that is effective for the treatment of diseases associated with GM-CSF, like inflammatory and autoimmune disorders.

Preferred dosages and preferred methods of administration are such that after administration the compound neutralizing GM-CSF is present in the blood in effective dosages. The administration schedule can be adjusted by observing the disease conditions and analyzing serum levels of the compound neutralizing GM-CSF in laboratory tests followed by either extending the administration interval e.g., from twice per week or once per week to once per two weeks, once per three weeks, once per four weeks, and the like, or, alternatively, reducing the administration interval correspondingly.

The pharmaceutical compositions can be administered to the subject at a suitable dose. The dosage regimen will be determined by the attending physician and by clinical factors. As is well known in the medical arts, dosages for any one patient depend upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the pharmaceutical composition in accordance with the present invention might comprise proteinaceous carriers, like, e.g., serum albumin or immunoglobulin, preferably of human origin. It is envisaged that the pharmaceutical composition in accordance with the invention might comprise, in addition to the above described compounds further biologically active agents, depending on the intended use of the pharmaceutical composition. Such agents might be drugs acting on the gastrointestinal system, drugs acting as cytostatica, drugs preventing hyperurikemia, drugs inhibiting immunoreactions (e.g., corticosteroids), drugs modulating the inflammatory response, drugs acting on the circulatory system and/or agents such as cytokines known in the art.

To analyze the effect of a GM-CSF neutralizing compound for example in rheumatoid arthritis (RA), outcome measures can be selected e.g., from pharmacokinetics, immunogenicity, and the potential to improve clinical signs and symptoms of RA as measured by DAS28, ACR20/50/70 and/or EULAR response criteria, MRI imaging for synovitis and bone edema as well as patient reported outcomes. ACR is a measure summarizing improvement in the number of tender and swollen joints, pain scale, patients' and physicians' assessment of improvement and certain laboratory markers. ACR 20 describes the percentage of study participants who achieved a 20 percent improvement in clinical signs and symptoms, e.g., 20 percent improvement in tender or swollen joint counts as well as 20 percent improvement in three other disease-relevant criteria.

Another major challenge in the development of drugs such as the pharmaceutical composition in accordance with the invention is the predictable modulation of pharmacokinetic properties. To this end, a pharmacokinetic profile of the drug candidate, i.e., a profile of the pharmacokinetic parameters that affect the ability of a particular drug to treat a given condition, is established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above. "Half-life" means the time where 50% of an administered drug are eliminated through biological processes, e.g., metabolism, excretion, etc. By "hepatic first-pass metabolism" is meant the propensity of a drug to be metabolized upon first contact with the liver, i.e., during its first pass through the liver. "Volume of distribution" means the degree of retention of a drug throughout the various compartments of the body, like e.g., intracellular and extracellular spaces, tissues and organs, etc. and the distribution of the drug within these compartments. "Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates and/or Cmax for a given amount of drug administered. "Bioavailability" means the amount of a drug in the blood compartment. "Lag time" means the time delay between the administration of the drug and its detection and measurability in blood or plasma. "Tmax" is the time after which maximal blood concentration of the drug is reached, the absorption is defined as the movement of a drug from the site of administration into the systemic circulation, and "Cmax" is the blood concentration maximally obtained with a given drug. The time to reach a blood or tissue concentration of the drug which is required for its biological effect is influenced by all parameters.

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The terms "safety", "in vivo safety" or "tolerability" as used herein define the administration of a drug without inducing severe adverse events directly after administration (local tolerance) and during a longer period of application of the drug. "Safety", "in vivo safety" or "tolerability" can be evaluated e.g., at regular intervals during the treatment and follow-up period. Measurements include clinical evaluation, e.g., organ manifestations, and screening of laboratory abnormalities. Clinical evaluation may be carried out and deviating to normal findings recorded/coded according to NCI-CTC and/or MedDRA standards. Organ manifestations may include criteria such as allergy/immunology, blood/bone marrow, cardiac arrhythmia, coagulation and the like, as set forth e.g., in the Common Terminology Criteria for adverse events v3.0 (CTCAE). Laboratory parameters which may be tested include for instance haematology, clinical chemistry, coagulation profile and urine analysis and examination of other body fluids such as serum, plasma, lymphoid or spinal fluid, liquor and the like. Safety can thus be assessed e.g., by physical examination, imaging techniques (i.e., ultrasound, x-ray, CT scans, Magnetic Resonance Imaging (MRI), other measures with technical devices (i.e., electrocardiogram), vital signs, by measuring laboratory parameters and recording adverse events. The term "effective and non-toxic dose" as used herein refers to a tolerable dose of the compound neutralizing GM-CSF, preferably the antibody as defined herein, which is high enough to cure or stabilize the disease of interest without or essentially without major toxic effects. Such effective and non-toxic doses may be determined e.g., by dose escalation studies described in the art and should be below the dose inducing severe adverse side events (dose limiting toxicity, DLT).

The formulation of the invention (sometimes also referred to herein as "composition of matter", "composition", or "solution") may preferably be in various physical states such as liquid, frozen, lyophilized, freeze-dried, spray-dried and reconstituted formulations, with liquid and frozen being preferred.

"Liquid formulation" as used herein refers to a composition of matter that is found as a liquid, characterized by free movement of the constituent molecules among themselves but without the tendency to separate at room temperature. Liquid formulations include aqueous and non-aqueous liquid, with aqueous formulations being preferred. An aqueous formulation is a formulation in which the solvent or main solvent is water, preferably water for injection (WFI). The dissolution of the compound neutralizing GM-CSF in the formulation may be homogenous or heterogeneous, with homogenous being preferred as described above.

Any suitable non-aqueous liquid may be employed provided that it provides stability to the formulation of the invention. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425 and PPG 725.

"Mixed aqueous/non-aqueous liquid formulation" as used herein refers to a liquid formulation that contains a mixture of water, preferably WFI, and an additional liquid composition.

When used herein a "formulation" or "composition" is a mixture of a compound neutralizing GM-CSF (i.e., the active drug/substance) and further chemical substances and/or additives required for a medicinal product which is preferably in a liquid state. A formulation of the invention includes a pharmaceutical formulation.

The preparation of the formulation includes the process in which different chemical substances, including the active drug, are combined to produce a final medicinal product such as a pharmaceutical composition. The active drug of the formulation of the invention is a compound neutralizing GM-CSF.

In certain embodiments, the compound neutralizing GM-CSF to be formulated is essentially pure and/or essentially homogeneous (i.e., substantially free from contaminating substances, e.g., proteins, etc. which can be product-related and/or process-related impurities). The term "essentially pure" means a composition comprising at least about 80%, preferably about 90% by weight of the compound, preferably at least about 95% by weight of the compound, more preferably at least about 97% by weight of the compound or most preferably at least about 98% by weight of the compound, preferably of the compound in a monomeric state. The term "essentially homogeneous" means a composition comprising at least about 99% by weight of the compound, preferably of the compound in a monomeric state, excluding the mass of various stabilizers and water in solution.

When used herein, the term "about" is understood to mean that there can be variation in the respective value or range (such as pH, concentration, percentage, molarity, number of amino acids, time etc.) that can be up to 5%, up to 10%, up to 15% or up to and including 20% of the given value. For example, if a formulation comprises about 5 mg/ml of a compound, this is understood to mean that a formulation can have between 4 and 6 mg/ml, preferably between 4.25 and 5.75 mg/ml, more preferably between 4.5 and 5.5 mg/ml and even more preferably between 4.75 and 5.25 mg/ml, with the most preferred being 5 mg/ml. As used herein, an interval which is defined as "(from) X to Y" equates with an interval which is defined as "between X and Y". Both intervals specifically include the upper limit and also the lower limit. This means that for example an interval of "5 mg/ml to 10 mg/ml" or "between 5 mg/ml and 10 mg/ml" includes a concentration of 5, 6, 7, 8, 9, and 10 mg/ml as well as any given intermediate value.

A "stable" formulation is one in which the compound neutralizing GM-CSF therein essentially retains its physical stability and/or chemical stability and/or biological activity upon storage and/or does not show substantial signs of aggregation, precipitation, fragmentation, degradation and/or denaturation compared to a control sample, preferably upon visual examination of colour and/or clarity, or as measured by UV light scattering or by size exclusion chromatography. Various further analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993), for example.

"During storage," as used herein, means a formulation that once prepared, is not immediately used; rather, following its preparation, it is packaged for storage, either in a liquid form, in a frozen state, or in a dried form for later reconstitution into a liquid form or other form.

It is envisaged that the compound neutralizing GM-CSF is preferably stable insofar as it does not substantially form aggregates or fragments/degradation products (for example, because of one or more of the aforementioned causes) during storage and/or during or after freeze/thawing and/or during or after shear (e.g., shaking) stress. Accordingly, it is preferably envisaged that not more than 10% of a compound neutralizing GM-CSF, more preferably not more than 8%, even more preferably not more than 5%, particularly preferably not more than 2% relative to the amount of the compound neutralizing GM-CSF at the beginning of storage or before carrying out one or more freeze/thaw cycles or before carrying out shaking studies forms aggregates and/or fragments. This stability preferably applies for a time range of at least 1 month, at least 2 months or at least 3 months; preferably at least 4 months, at least 5 months or at least 6 months; more preferably at least 9 months or at least 12 months; even more preferably at least 18 months or at least 24 months; and most preferably at least 30 months or at least 36 months or at least 48 months or at least 54 months or at least 60 months. The preferred storage temperature conditions are up to room temperature (about 20° C. to about 25° C.), more preferably about 2-8° C., the most preferred time range is at least 3 years or even at least 4 years. The number of freeze/thaw cycles during which the compound is preferably stable according to the above parameters is at least one cycle, preferably at least 2, 3, or 4 cycles, more preferably at least 5, 6 or 7 cycles, and most preferably at least 8, 9 or 10 cycles. The number of days of shaking during which the compound is preferably stable according to the above parameters (e.g., at a temperature of +5° C.±3° C., see also Example 12d) is at least 1 day, preferably at least 2, 3, or 4 days, more preferably at least 5, 6 or 7 days, even more preferably at least 8, 9, 10 or 11 days and most preferably at least 12, 13 or 14 days.

In the alternative, it is envisaged that a compound neutralizing GM-CSF is preferably stable insofar that it does not form dimers, oligomers or fragments. Put it differently, the stability of a compound neutralizing GM-CSF can be determined according to the percentage of monomer protein in the solution, with a low percentage of degraded (e.g., fragmented) and/or aggregated protein. For example, a formulation of the invention comprising a GM-CSF neutralizing compound such as an antibody may include at least 90%, more preferably at least 92%, even more preferably at least 95%, particularly preferably at least 98%, and most preferably at least 99% monomer of the compound neutralizing GM-CSF.

By "aggregate" is meant a physical interaction between protein molecules that results in the formation of covalent or non-covalent dimers or oligomers (i.e., high molecular weight entities) which may remain soluble, or form insoluble aggregates that precipitate out of solution. An "aggregate" also includes degraded and/or fragmented protein.

As mentioned herein above, a number of different analytical methods can be used to detect the presence and levels of aggregates in a formulation comprising a compound neutralizing GM-CSF. These include, but are not limited to, for example, native polyacrylamide gel electrophoresis (PAGE), sodium dodecyl sulfate-polyacrylamide gel electrophoresis (SDS-PAGE), capillary gel electrophoresis (CGE), size exclusion chromatography (SEC), analytical ultracentrifugation (AUC), field flow fractionation (FFF), light scattering detection, sedimentation velocity, UV spectroscopy, differential scanning calorimietry, turbidimetry, nephelometry, microscopy, size exclusion-high performance liquid chromatography (SE-HPLC), reverse phase-high performance liquid chromatography (RP-HPLC), electrospray ionization tandem mass spectroscopy (ESI-MS), and tandem RP-HPLC/ESI-MS, flow field-flow fractionation technique and static and/or dynamic light scattering. These methods may be used either alone, or in combination. Preferably, the analytical methods to detect the presence and levels of aggregates and/or fragments in a formulation comprising a compound neutralizing GM-CSF, are size exclusion chromatography such as SE-HPLC, analytical ultracentrifugation and asymmetric field flow fractionation. A method of determining the biologic activity of a compound neutralizing GM-CSF is e.g., the measurement of its degree of binding to (immobilized) GM-CSF (or GM-CSF receptor) is the so-called surface plasmon resonance (SPR).

A common challenge with a formulation comprising a protein is the irreversible accumulation of aggregates with time, thermal, or shear stress. Typically, when aggregates precipitate they form large particles that are easy to detect. Smaller, non-covalent soluble aggregates, however, which are often precursors of precipitation into large particles, are more difficult to detect and to quantify. Thus, methods to detect and to quantify protein aggregation in a protein formulation need to be based on the kind of aggregate being assessed.

Among the above methods, the suggested methods to determine the presence and/or amounts of soluble, covalent aggregates in a protein formulation are: SEC/light scattering, SDS-PAGE, CGE, RP-HPLC/ESI-MS, FFF and AUC: The suggested methods to determine the presence and/or amounts of soluble, non-covalent aggregates in a protein formulation are: SEC, PAGE, SDS-PAGE, CGE, FFF, AUC, and dynamic light scattering. The suggested methods to determine the presence and/or amounts of insoluble, non-covalent aggregates in a protein formulation are: UV spectroscopy, turbidimetry, nephelometry, microscopy, AUC, asymmetric field flow fractionation and dynamic light scattering.

Moreover, the formulation of the invention preferably provides improved long-term storage such that the compound neutralizing GM-CSF is stable over the course of storage either in liquid or frozen, preferably in liquid form. As used herein, the phrase “long-term” storage is understood to mean that the formulation can be stored for at least one month, two or three months or more, for six months or more, and preferably for one year and more or even 2 years, 3 years or 4 years or 5 years and more. Long term storage is also understood to mean that the pharmaceutical composition is stored either at 2-8° C. or at ambient temperature, preferably at 2-8° C., thereby the formulation preferably does not lose its biological activity to the extent as described herein and/or does not form aggregates to the extent as described herein and/or comprises monomers to the extent as described herein. Tests for these properties are described herein elsewhere.

In one aspect of the invention, the compound neutralizing GM-CSF in the formulations is stable in a liquid form for at least 1 month, 2 months, 3 months; at least 4 months, at least 5 months; at least 6 months; at least 12 months; at least 24 months; at least 36 months; at least 48 months, at last 60 months. Ranges intermediate to the above recited time periods are also intended to be part of this invention, e.g., 9 months, and so forth. In addition, ranges of values using a combination of any of the above recited values as upper and/or lower limits are intended to be included. Preferably, the formulation is stable at room temperature (about 20° C. to 25° C.) for at least 1 month and/or stable at about 2-8° C. for at least 1, 2, 3, 4, 5, 6, 7, 8, 9, 10, 11 or 12 months, or more preferably stable at about 2-8° C. for at least 2 years, at least 3 years, at least 4 years or even at least 5 years.

Another important aspect of stability is that the compound neutralizing GM-CSF within the composition according to the invention maintains its biological activity or potency during the time of storage and within the storage conditions, especially the temperature and possible temperature changes. The activity or potency is e.g., reflected by the compound's neutralizing capacity itself (which can be measured in cell-based assays, as described herein above) or by the capacity of the GM-CSF neutralizing compound to bind to GM-CSF or to the GM-CSF receptor. The binding affinity can be assessed by SPR or other methods well known in the art, e.g., a Biacore or a Scatchard assay.

The formulation of the invention is prepared by adding to a compound neutralizing GM-CSF as described herein, e.g., in an aqueous solution, a buffer and a tonicity modifier. Persons having ordinary skill in the art will understand that the combining of the various components to be included in the formulation can be done in any appropriate order. For example, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture.

In a preferred aspect of the invention the formulation comprises a buffer. The term "buffer" or "buffering agent" as used herein, includes those agents that maintain the pH in a desired range. A buffer is an aqueous solution consisting of a mixture of a weak acid and its conjugate base or a weak base and its conjugated acid. It has the property that the pH of the solution changes very little when a small amount of a strong acid or base is added. Buffer solutions are used as a means of keeping pH at a nearly constant value in a wide variety of chemical applications. In general, a buffer when applied in the formulation of the invention preferably stabilizes the compound neutralizing GM-CSF.

"Amino acid buffers" when used herein include, for example, the amino acid base e.g., histidine and its conjugated salt. An example of an amino acid buffer is histidine/histidine chloride. This example is preferably applied in the invention.

The preferred pH of a formulation as described herein may be chosen from the following ranges: from about 4 to about 10, preferably from about 4 to about 6 or from about 5 to about 7, more preferably from about 5.5 to about 6.5. Most preferably the pH is about or exactly 5.8. Accordingly, a buffer that can maintain a solution at pH 5 to 7 is preferably used. The term "about" when used in the context of pH value/range preferably means a numeric value having a range of +/−20% around the cited value. When the pH of the pharmaceutical composition is set at or near physiological levels, comfort of the patient upon administration is maximized. It is to be understood that the pH can be adjusted as necessary to maximize stability and solubility of the compound neutralizing GM-CSF in a particular formulation and as such, a pH outside of physiological ranges, yet preferably tolerable to the patient, is within the scope of the invention.

Non-limiting examples of buffers that may be used in a formulation described herein include, histidine, succinate, gluconate, citrate, arginine, lysine, aspartic acid, glutamic acid, tris (trometamol), Bis-Tris, MOPS, ACES, TES, HEPES, EPPS, ethylenediamine, phosphoric acid, maleic acid/phosphate, 2-morpholinoethanesulfonic acid (MES), phosphate, acetate and diethanolamine.

Preferred buffers are histidine, acetate and citrate buffers. More preferably a histidine buffer is applied in the formulation of the invention, preferably between pH 5 and 7, more preferably between pH 5.5 and 6.5, even more preferably at pH 5.8. The buffers applied in the invention are well known in the art and are manufactured by known methods and available from commercial suppliers.

In some embodiments, the formulation further comprises sodium hydroxide (NaOH). In particular embodiments, the formulation comprises 1-200 mM, or less than 50 mM, less than 40 mM, less than 35 mM, less than 30 mM, less than 25 mM, less than 20 mM, or less than 15 mM, e.g., 10 mM NaOH or less, such as 5 mM or 1 mM sodium hydroxide.

In addition to the compound neutralizing GM-CSF and the buffer, a formulation according to the invention may also contain other substances which include, but are not limited to, stabilizing agents (stabilizers).

Accordingly, in a preferred aspect, the formulation comprises a stabilizer which may also act as a tonicity modifier. The term "stabilizing agent" refers to an agent that improves or otherwise enhances stability of the formulation, in particular of the compounds neutralizing GM-CSF. A stabilizing agent which is a tonicity modifier may be a non-reducing sugar, a sugar alcohol or a combination thereof. The tonicity modifiers in the liquid compositions of the present invention ensure that the tonicity, i.e., osmolarity, of the solution is essentially the same as normal physiological fluids and thus prevent post-administration swelling or rapid absorption of the composition because of differential ion concentrations between the composition and physiological fluids. Generally, the nature of a formulation as described herein is such that the osmolality of the formulation is between about 240 and about 470 mOsmol/kg, more preferably between about 300 and about 400 mOsmol/kg, most preferably about 350 mOsmol/kg.

Preferably, the stabilizing agent/tonicity modifier may be one or more of non-reducing sugars, such as sucrose or trehalose or one or more of sugar alcohols, such as mannitol or sorbitol, also combinations of non-reducing sugars and sugar alcohols are preferred. In certain embodiments, the concentration of the stabilizing agent/tonicity modifier in the composition is chosen from the following ranges: from 1 to 15% (w/v), from 2 to 10% (w/v), from 3 to 8% (w/v), from 4 to 6.5% (w/w), from 4.5 to 6%, (w/v). In particular embodiments, the concentration is about 5 to 6% (w/v). A preferred stabilizer/tonicity modifier applied in the formulation of the invention is sorbitol, preferably at 5% (w/v).

In a preferred embodiment, a formulation described herein does not comprise further excipients, like amino-acids (except when the buffer is chosen from an amino acid buffer such as a histidine buffer) or surfactants.

In less preferred embodiments, a formulation described herein comprises an additional excipient. Preferably the excipient is selected from the group consisting of an amino-acid, a cryoprotectant, a lyoprotectant, a surfactant, a bulking agent, an antioxidant, and combinations thereof.

Excipients, also referred to as chemical additives, co-solutes, or co-solvents, that preferably stabilize the compounds neutralizing GM-CSF while in solution (also in dried or frozen forms) can be added to a formulation of the invention. Preferably, excipients contribute to the stability of the compounds neutralizing GM-CSF, but it is to be understood that excipients may otherwise contribute to the physical, chemical, and biological properties of the formulation. Excipients are well known in the art and are manufactured by known methods and available from commercial suppliers.

Examples of excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), d extra n, PVA, hydroxypropyl methylcellulose (HPMC), polyethyleneimine, gelatin, polyvinylpyrrolidone (PVP), hydroxyethylcellulose (HEC), hydroxyethylstarch (HES); non-aqueous solvents such as: polyhydric alcohols, (e.g., PEG, ethylene glycol and glycerol) dimethysulfoxide (DMSO) and dimethylformamide (DMF); amino acids such as: threonine, serine, proline, alanine, valine, glutamine, methionine, cysteine, isoleucine, aspartic acid, glutamic acid, arginine, glycine, histidine, lysine, phenylalanine, leucine, asparagine, tryptophan and tyrosin; surfactants such as: Tween-80, Tween-20, SDS, polysorbate, polyoxyethylene copolymer; and miscellaneous excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate or any combination of the above.

"Cryoprotectants" include substances that provide stability to the frozen protein during production, freezing, storage, handling, distribution, reconstitution, or use. In a particular aspect, "cryoprotectants" include substances that protect the protein from stresses induced by the freezing process. Cryoprotectants may have lyoprotectant effects. Non-limiting examples of cryoprotectants include sugars, such as sucrose, glucose, trehalose, mannitol, sorbitol, mannose, and lactose; polymers, such as d extra n, hydroxyethyl starch, Polyvinylpyrrolidone (PVP) and polyethylene glycol; surfactants, such as polysorbates (e.g., PS-20 or PS-80); and amino acids, such as glycine, arginine, leucine, and serine. A cryoprotectant exhibiting low toxicity in biological systems is generally used.

A disaccharide as described herein may act as a lyoprotectant or cryoprotectant. "Lyoprotectants" include substances that prevent or reduce chemical or physical instability of a protein upon lyophilization and subsequent storage. In one aspect, the lyoprotectant prevents or reduces chemical or physical instabilities in the protein as water is removed from the composition during the drying process. In a further aspect, the lyoprotectant stabilizes the protein by helping maintain the proper conformation of the protein through hydrogen bonding.

Accordingly, in one aspect, a disaccharide as described herein may serve to stabilize the compounds neutralizing GM-CSF during freezing. As protection during freezing may depend upon the absolute concentration of the disaccharide (Carpenter et al., Pharm. Res. (1997), 14:969-975, concentrations greater than 5% may be necessary to maximize stability.

In one embodiment, a lyoprotectant is added to a formulation described herein. The term "lyoprotectant" as used herein, includes agents that provide stability to the protein during the freeze-drying or dehydration process (primary and secondary freeze-drying cycles), by providing an amorphous glassy matrix and by binding with the protein through hydrogen bonding, replacing the water molecules that are removed during the drying process. This helps to maintain the protein conformation, minimize protein degradation during the lyophilization cycle, and improve the long-term product stability. The lyoprotectant is added to the pre-lyophilized formulation in a "lyoprotecting amount" which means that, following lyophilization of the compounds neutralizing GM-CSF in the presence of the lyoprotecting amount of the lyoprotectant, the compounds essentially retains their physical and chemical stability and integrity upon lyophilization and storage.

Non-limiting examples of lyoprotectants include sugars, such as sucrose or trehalose; an amino acid, such as monosodium glutamate, glycine or histidine; a methylamine, such as betaine; a lyotropic salt, such as magnesium sulfate; a polyol, such as trihydric or higher sugar alcohols, e.g., arabitol, xylitol, sorbitol, and mannitol; polyethylene glycol; pluronics; and combinations thereof. Preferably lyoprotectans are as described above for stabilizing agents. The amount of lyoprotectant added to a formulation is generally an amount that does not lead to an unacceptable degree of degradation/aggregation of the protein when the protein formulation is lyophilized.

Another excipient is a surfactant. The term "surfactant" generally includes those agents that protect the compounds neutralizing GM-CSF from air/solution interface-induced stresses and solution/surface induced-stresses. For example surfactants may protect the protein from aggregation.

Examples of surfactants include, without limitation, non-ionic surfactants, such as polysorbates (e.g., polysorbate 80 or polysorbate 20); poloxamers (e.g., poloxamer 188); Triton, sodium dodecyl sulfate (SDS); sodium laurel sulfate; sodium octyl glycoside; lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine (e.g., lauroamidopropyl), myristarnidopropyl-, palmidopropyl-, or isostearamidopropyl-dimethylamine; sodium methyl cocoyl-, or disodium methyl ofeyl-taurate; and the Monaquat series (Mona Industries, Inc., Paterson, N.J.), polyethyl glycol, polypropyl glycol, and copolymers of ethylene and propylene glycol (e.g., pluronics, PF68). The amount of surfactant added is such that it maintains aggregation of the protein at an acceptable level as assayed using, e.g., SEC-HPLC, or light obscuration measurements to determine the percentage of high molecular weight (HMW) species or low molecular weight (LMW) species, and minimizes the formation of particulates of a protein formulation described herein.

A further preferred excipient may by a bulking agent. The term "bulking agent" as used herein, includes agents that provide the structure of a freeze-dried product without interacting directly with the pharmaceutical product. In addition to providing a pharmaceutically elegant cake, bulking agents may also impart useful qualities in regard to modifying the collapse temperature, providing freeze-thaw protection, and enhancing the protein stability over long-term storage. Non-limiting examples of bulking agents include mannitol, glycine, lactose, and sucrose. Bulking agents may be crystalline (such as glycine, mannitol, or sodium chloride) or amorphous (such as dextran, hydroxyethyl starch) and are generally used in protein formulations in an amount from 0.5% to 10%.

Preferably, the bulking agent applied in the formulation of the invention promotes the formation of a cake that is aesthetically acceptable, uniform, or mechanically strong. Bulking agents also preferably promote the formation of an open pore structure and the ease and speed of reconstitution. Bulking agents also preferably reduce or prevent cake collapse, eutectic melting, or retention of residual moisture. In another aspect, bulking agents preferably help protect the compounds neutralizing GM-CSF against stresses (e.g., physical and chemical stresses) and help maintain protein activity.

Another preferred excipient may be an antioxidant. As used herein, an "antioxidant" is a molecule capable of slowing or preventing the oxidation of other molecules. Oxidation is a chemical reaction that transfers electrons from a substance to an oxidizing agent. For use in the composition of the invention, physiologically acceptable antioxidants are of interest. Such antioxidants include, without limitation, reducing agents, ascorbic acid (vitamin C), lipoic acid, melatonin, uric acid, carotenes, retinols, tocopherols and tocotrienols, e.g., α-tocopherol (vitamin E), ubiquinone (coenzyme Q), and the like.

In some embodiments, the formulation may optionally contain a preservative. A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl parabene, catechol, resorcinol, cyclohexanol, 3-pentanol, and m-cresol. The most preferred preservative herein is benzyl alcohol.

Accordingly, in more preferred embodiments, the formulation of the invention is a liquid, preferably aqueous, formulation for long-term storage which comprises between about 100 mg/ml and 200 mg/ml of a compound neutralizing GM-CSF and a buffer selected from the group consisting of histidine, acetate and citrate, at a pH of about 5 to about 7, and the formulation may additionally comprises one or more of sucrose, trehalose, mannitol and/or sorbitol as stabilizer/tonicity modifier.

In particular preferred embodiments a formulation of the invention is a liquid, preferably aqueous, formulation for long-term storage which comprises between about 100 mg/ml and 200 mg/ml of a compound neutralizing GM-CSF, more preferably about 150 mg/ml, and a histidine buffer at a concentration of about 20 mM to about 40 mM, more preferably about 30 mM, at a pH of about 5.5 to about 6.5, more preferably 5.8, and the formulation may additionally comprises about 4% to about 6%, more preferably about 5% (w/v) sorbitol and optionally no additional excipients like surfactants, amino acids and/or NaCl.

It is to be understood that certain components of the composition may be interchanged with alternatives known in the art. However, one skilled in the art will also understand that inclusion of certain components will preclude the use of other components, concentrations, or methods of preparing the formulation, for reasons that include, but are not limited to, chemical compatibility, pH, tonicity, and stability.

It is beneficial for the liquid formulation of the invention to have a low and feasible viscosity which is suitable for subcutaneous administration, such as in a ready to use device The viscosity of the formulation according to the invention is hence preferably below 20 mPa*s at a shear rate between about 50 and about 1000 [1/sec] and at a temperature of about 20° C. More preferably the viscosity is below 15 mPa*s at the above conditions.

As mentioned herein, this application generally relates to the discovery that the addition of several substances to a formulation comprising compounds neutralizing GM-CSF can reduce aggregation and/or degradation/fragmentation of these compounds in a formulation. Regardless of what causes a compound neutralizing GM-CSF in a formulation to aggregate or to be degraded, the addition of the substances as described herein reduces aggregation/fragmentation of the compounds neutralizing GM-CSF in the formulation. In certain embodiments, addition of a the described substances reduces aggregation/degradation in a formulation caused, for example, by storage, exposure to elevated temperatures, exposure to light, exposure to shear stress, the presence of surfactants, pH and ionic conditions, and any combinations thereof.

The measures found by the present inventors may be used to decrease aggregation and/or degradation/fragmentation of compounds neutralizing GM-CSF formulated, in particular, in liquid and frozen form. The reduced aggregation/fragmentation is thus preferably observed in a liquid formulation. It is assumed that a reduced aggregation/degradation may also be observed when stored directly in liquid form for later use, stored in a frozen state and thawed prior to use, or prepared in a dried form, such as a lyophilized, air-dried, or spray-dried form, for later reconstitution into a liquid form or other form prior to use.

Thus, it is envisaged that a formulation described herein may be stored by any method known to one of skill in the art. Non-limiting examples include cooling, freezing, lyophilizing, and spray drying the formulation, wherein storage by cooling is preferred.

In some cases, the protein formulations are frozen for storage. Accordingly, it is desirable that the formulation be relatively stable under such conditions, including under freeze-thaw cycles. One method of determining this suitability of a formulation is to subject a sample of the formulation to at least one, e.g., one, three, five, seven and up to ten cycles of freezing and thawing (for example by freezing at about −80° C.±10° C. over night and fast thaw at room temperature or slow thaw on ice, e.g., for 6 hours), determining the amount of low molecular weight (LMW) species and/or high molecular weight (HMW) species that accumulate after the freeze-thaw cycles and comparing it to the amount of LMW species or BMW species present in the sample prior to the freeze-thaw procedure. An increase in the LMW or HMW species indicates decreased stability of a protein stored as part of the formulation. Size exclusion high performance liquid chromatography (SE-HPLC) can be used to determine the presence of LMW and BMW species.

Preferably, the protein formulations may be stored as a liquid. Accordingly, as described herein, it is desirable that the liquid formulation be stable under such conditions, including at various temperatures. For example, one method of determining the suitability of a formulation is to store the sample formulation at several temperatures (such as 2-8° C., 15° C., 20° C., 25° C., 30° C., 35° C., 40° C., and 50° C.) and monitoring the amount of HMW and/or LMW species that accumulate over time. The smaller the amounts of HMW and/or LMW species that accumulate over time, the better the storage condition for the formulation. Additionally, the charge profile of the protein may be monitored by cation exchange-high performance liquid chromatography (CEX-HPLC). Alternatively, formulations can be stored after lyophilization. It is furthermore desirable that the formulation is stable under conditions of shear stress. One method of determining the suitability of a formulation is to joggle the formulation in a recipient on a shaker, e.g., a vertical shaker, at a desired temperature (such as 2-8° C., 15° C., 20° C., 25° C., 30° C., 35° C., 40° C., and 50° C., preferably +5° C.±3° C.). The recipient (e.g., a vial) can be stored on a shaker for a desired period of time, for example up to 14 days or longer, versus a control which is stored unshaken at the same temperature. Data point collection can be carried out e.g., after 0, 1, 2, 3, 4, 5, 6, 7, 8, 9, 10, 11, 12 14 and 14 days. The amount of low molecular weight (LMW) species and/or high molecular weight (HMW) species that accumulate after the shaking storage can be determined and compared to the amount of LMW species or BMW species present in the unshaken sample. An increase in the LMW or BMW species indicates decreased stability of a protein stored as part of the formulation. Size exclusion high performance liquid chromatography (SE-HPLC) can be used to determine the presence of LMW and HMW species.

In some cases, a formulation is spray-dried and then stored. For spray-drying, a liquid formulation is aerosolized in the presence of a dry gas stream. Water is removed from the formulation droplets into the gas stream, resulting in dried particles of the drug formulation. Excipients may be included in the formulation to (i) protect the protein during the spray-drying dehydration, (ii) protect the protein during storage after spray-drying, and/or (iii) give the solution properties suitable for aerosolization. The method is similar to that described above for freezing, except that the sample formulation is spray-dried instead of frozen, reconstituted in a diluent, and the reconstituted formulation is tested for the presence of LMW species and/or HMW species. An increase in LMW or BMW species in the spray-dried sample compared to a corresponding sample formulation that was not lyophilized indicates decreased stability in the spray-dried sample.

The term "lyophilized" or "freeze-dried" includes a state of a substance that has been subjected to a drying procedure such as lyophilization, where at least 90% preferably 95%, most preferably 98% of moisture has been removed. Accordingly, the term "lyophilization" as used herein, refers to a process by which the material to be dried is first frozen followed by removal of the ice or frozen solvent by sublimation in a vacuum environment. An excipient (e.g., lyoprotectant) may be included in formulations that are to be lyophilized so as to enhance stability of the lyophilized product upon storage. The term "reconstituted formulation" as used herein, refers to a formulation that has been prepared by dissolving a lyophilized protein formulation in a diluent such that the compound neutralizing GM-CSF is dispersed in the diluent.

The term "diluent" as used herein, is a substance that is pharmaceutically acceptable (safe and non-toxic for administration to a human) and is useful for the preparation of a liquid formulation, such as a formulation reconstituted after lyophilization. Non-limiting examples of diluents include sterile water, bacteriostatic water for injection (BWFI), a pH buffered solution (e.g., phosphate-buffered saline), sterile saline solution, Ringer's solution, dextrose solution, or aqueous solutions of salts and/or buffers.

In another aspect of the invention, the formulation is envisaged for use in therapy. Accordingly, the invention envisages a pharmaceutical composition (or medicament) comprising the formulation described herein.

In yet another embodiment, the invention provides a method of treating a subject comprising administering a therapeutically effective amount of the formulation described herein, wherein the subject has a disease or disorder that can be beneficially treated with a compound neutralizing GM-CSF.

Preferably, the formulation described herein is applied in the prophylaxis and/or treatment of a disease that can be prevented and/or treated and/or ameliorated with compounds neutralizing GM-CSF.

The term "subject" is intended to include living organisms. Examples of subjects include mammals, e.g., humans, dogs, cows, horses, pigs, sheep, goats, cats, mice, rabbits, rats, and transgenic non-human animals. In preferred embodiments of the invention, the subject is a human.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the medical condition and the general state of the subject's own immune system. The term "patient" includes human and other mammalian subjects that receive either prophylactic or therapeutic treatment.

The appropriate dosage, or therapeutically effective amount, of the formulation will depend on the condition to be treated, the severity of the condition prior to therapy, and the patient's clinical history and response to the therapeutic agent. The proper dose can be adjusted according to the judgment of the attending physician such that it can be administered to the patient once or over a series of administrations. The pharmaceutical composition can be administered as a sole therapeutic or in combination with additional therapies as needed.

The pharmaceutical compositions of this invention are particularly useful for parenteral administration, i.e., subcutaneously, intramuscularly, intravenously, intra-articular and/or intra-synovial, wherein subcutaneous administration is preferred. Parenteral administration can be carried out by bolus injection or continuous infusion.

Pharmaceutical compositions for injection may be presented in unit dosage form, e.g., in ampoules or in multidose containers, with an added preservative. In addition, a number of recent drug delivery approaches have been developed and the pharmaceutical compositions of the present invention are suitable for administration using these new methods, e.g., Inject-ease, Genject, injector pens such as Genen, and needleless devices such as MediJector and BioJector. The present pharmaceutical composition can also be adapted for yet to be discovered administration methods. See also Langer, 1990, Science, 249:1527-1533.

The lyophilized pharmaceutical compositions may preferably be presented in a vial containing the active ingredient. In one embodiment the pharmaceutical compositions additionally comprise a solution for reconstruction.

The pharmaceutical composition may further comprise additional pharmaceutically acceptable components. Other pharmaceutically acceptable carriers, excipients, or stabilizers, such as those described in Remington's Pharmaceutical Sciences 16th edition, Osol, A. Ed. (1980) may also be included in a protein formulation described herein, provided that they do not adversely affect the desired characteristics of the formulation. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are non-toxic to recipients at the dosages and concentrations employed and include: tonicity modifiers; additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counter-ions, such as sodium, polyhydric sugar alcohols; amino acids, such as alanine, glycine, asparagine, 2-phenylalanine, and threonine; sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatine, or other immunoglobulins; and hydrophilic polymers, such as polyvinylpyrrolidone.

The formulations described herein are useful as pharmaceutical compositions in the treatment and/or prevention and/or amelioration of a disease, or disorder in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

Those "in need of treatment" include those already with the disorder, as well as those in which the disorder is to be prevented. The term "disorder" is any condition that would benefit from treatment with the protein formulation described herein. This includes chronic and acute disorders or diseases including those pathological conditions that predispose the mammal to the disorder in question. Non-limiting examples of disorders to be treated herein include inflammatory and autoimmune disorders, preferably including allergic and psoriatic disorders, as well as arthritic and asthmatic disorders, e.g., arthritis, rheumatoid arthritis (RA), autoimmune encephalitis, psoriasis, multiple sclerosis, lung disease such as asthma, chronic obstructive pulmonary disease (COPD) and Acute Respiratory Distress Syndrome (ARDS); Crohn's Disease, Idiopathic Pulmonary Fibrosis (IPF), Inflammatory Bowel Disease (IBD), uveitis, macular degeneration, colitis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus, atopic dermatitis, and inflammatory, arthritic and osteoarthritic pain.

An allergic disorder is any disorder that is caused by an allergy or an allergic reaction. An allergy is a hypersensitivity disorder of the immune system. It occurs when a person's immune system reacts or overreacts to normally harmless foreign substances (allergens), such as food, pollen, molds, house dust, animal dander, dust mites.

Psoriasis is an autoimmune disease that mainly affects the skin. The growth cycle of skin cells speeds up due to erroneous signals sent out by the immune system. There are five types of psoriasis: plaque, guttate, inverse, pustular, and erythrodermic. The most common form, plaque psoriasis, is commonly seen as red and white hues of scaly patches appearing on the top first layer of the epidermis (skin). Some patients, though, have no dermatological signs or symptoms. The disorder is a chronic recurring condition that varies in severity from minor localized patches to complete body coverage. Fingernails and toenails are frequently affected (psoriatic nail dystrophy) and can be seen as an isolated sign. Psoriasis can also cause inflammation of the joints, which is known as psoriatic arthritis.

Arthritis is a form of joint disorder that involves inflammation of one or more joints. There are over 100 different forms of arthritis. The most common form osteoarthritis (degenerative joint disease) is a result of trauma to the joint, infection of the joint, or age. Other arthritis forms are rheumatoid arthritis, psoriatic arthritis and other related autoimmune diseases. Septic arthritis is caused by joint infection.

Asthma is a common chronic inflammatory disorder of the airways in which many cells and cellular elements play a role. Asthma is associated with airway hyperresponsiveness that leads to recurrent episodes of wheezing, coughing, chest tightness, and shortness of breath. These episodes are usually associated with widespread, but variable airflow obstruction within the lung that is often reversible either spontaneously or with treatment. Asthma can be classified according to the frequency of symptoms, forced expiratory volume in one second and peak expiratory flow rate. Asthma may also be classified as atopic (extrinsic) or non-atopic (intrinsic).

In addition to the compounds neutralizing GM-CSF, the pharmaceutical composition of the invention can comprise additional therapeutic or biologically active agents. For example, therapeutic factors useful in the treatment of a particular indication such as osteoarthritis (e.g., one or more inhibitors that are involved in destruction of articular cartilage or synovial components selected from, but not limited to anti-metalloproteinases, cycline compounds, cytokine antagonists, corticosteroids, TNF inhibitors, IL-inhibitors, anti-angiogenic substances, aggrecanase inhibitors, p38 kinase inhibitors, apoptosis inhibitors, hyaluronidase inhibitors and inhibitors of proteolytic enzymes) can be present. Factors that control inflammation including infliximab, etanercept, adalimulab, nerelimonmab, lenercept and the like, or combinations thereof can also be part of the composition. It is also envisaged that the pharmaceutical composition may include extracellular matrix components such as hyaluronic acid or a derivative thereof including salts, ester, inner ester and sulphated derivates, preferably partial ester of hyaluronic acid.

In another embodiment, the present invention is directed to a kit (or article of manufacture) or container, which contains a formulation of the invention. The formulation may preferably already be in a liquid state. However, alternatively, it may preferably be in a lyophilized state. It may also be in a frozen, lyophilized, freeze-dried or spray-dried state. Accordingly, if the formulation is in state other than liquid, it can be prepared by the practitioner as (liquid) aqueous pharmaceutical composition. For example, the formulation may be lyophilized and would then have to be reconstituted. Accordingly, the kit may further comprise means for the reconstitution of a frozen, lyophilized, freeze-dried or spray-dried formulation and/or means for diluting the formulation and/or means for administering the formulation or pharmaceutical composition, respectively, such as a syringe, pump, infuser, needle or the like. The kit may comprise one or more vials containing the formulation of the invention. The kit can also be accompanied by instructions for use.

Thus, an article of manufacture is provided which contains a formulation described herein and preferably provides instructions for its use. The article of manufacture comprises a container suitable for containing the formulation. Suitable containers include, without limitation, bottles, vials (e.g., dual chamber vials), syringes (e.g., single or dual chamber syringes), test tubes, nebulizers, inhalers (e.g., metered dose inhalers or dry powder inhalers), or depots. The container can be formed from a variety of materials, such as glass, metal or plastic (e.g., polycarbonate, polystyrene, polypropylene, polyolefine). The container holds the formulation, and the label on, or associated with, the container may indicate directions for reconstitution and/or use. The label may further indicate that the formulation is useful or intended for subcutaneous administration. The container holding the formulation may be a multi-use vial, which allows for repeated administrations (e.g., from 2-6 administrations) of the formulation. The article of manufacture may further comprise a second container comprising a suitable diluent (e.g., WFI, 0.9% NaCl, BWFI, phosphate buffered saline). When the article of manufacture comprises a lyophilized version of a compound neutralizing GM-CSF formulation, mixing of a diluent with the lyophilized formulation will provide a desired final protein concentration in the reconstituted formulation. The article of manufacture may further include other materials desirable from a commercial and user standpoint, including other buffers, diluents, filters, needles, syringes, and package inserts with instructions for use.

Also included in the invention are devices that may be used to deliver the formulation of the invention. Examples of such devices include, but are not limited to, a syringe, a pen, an implant, a needle-free injection device, an inhalation device, and a patch.

The invention is further illustrated by the Figures and Examples which are merely illustrative and are not constructed as a limitation of the scope of the present invention.

Figure 1:
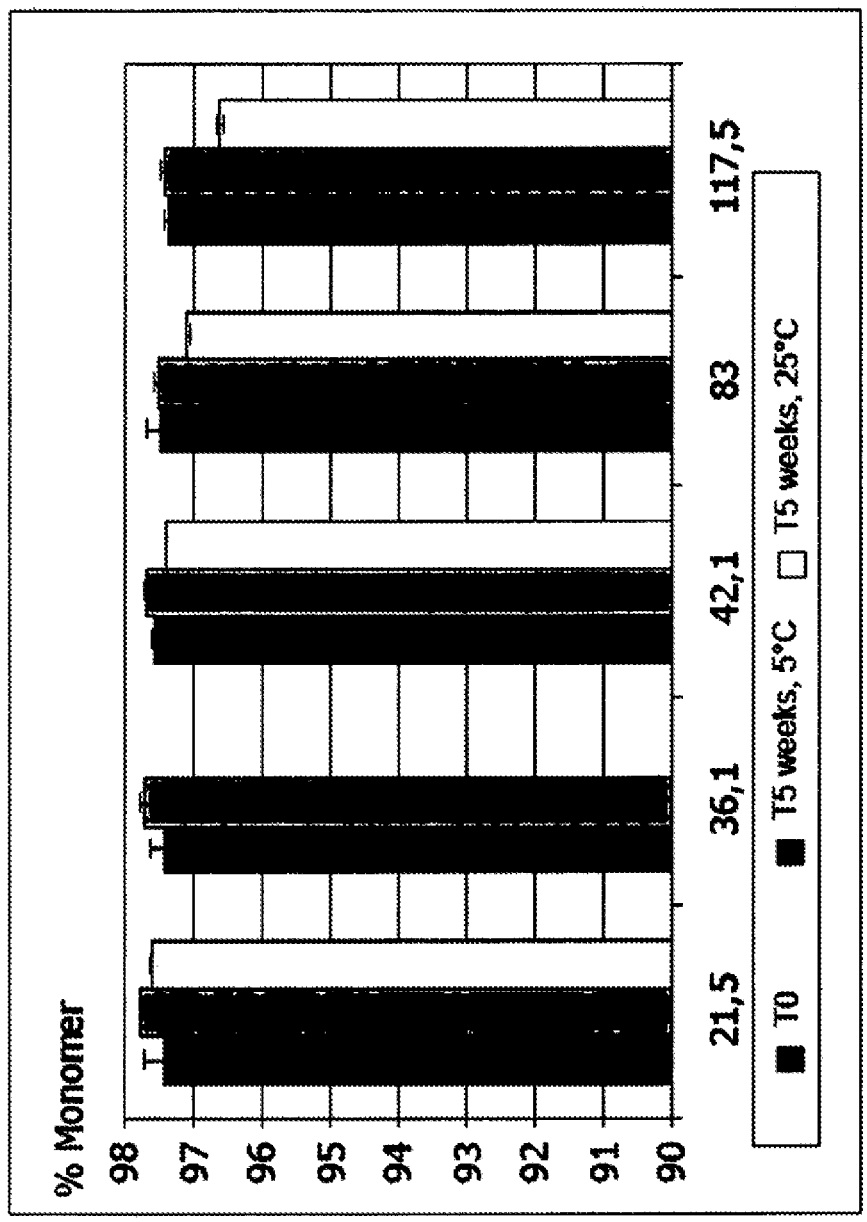
FIG. 1 shows the effect of storage time, storage temperature, and protein concentration on the monomer level of the anti-GM-CSF antibody.

The following items also characterize the present invention:

1. A composition comprising a compound neutralizing GM-CSF in a concentration of at least about 20 mg/ml, a tonicity modifier and a buffer, wherein the composition is stable.

2. The composition according to item 1, wherein the compound neutralizing GM-CSF is present in a concentration of at least about 50 mg/ml, the tonicity modifier is present in a concentration from about 1% to about 15% (w/v) and the buffer is present in a concentration from about 10 mM to about 50 mM.

3. The composition according to item 1 or 2, wherein the tonicity modifier is selected from mannitol, sorbitol, sucrose and/or trehalose.

4. The composition according to any one of items 1 to 3, wherein the buffer is selected from a histidine, acetate and/or citrate buffer.

5. The composition according to any one of items 1 to 4, wherein the compound neutralizing GM-CSF is present in a concentration of at least about 100 mg/ml and less than about 200 mg/ml, the tonicity modifier is present in a concentration from about 3% to about 7% (w/v) and the buffer is present in a concentration from about 20 mM to about 40 mM.

6. The composition according to any one of items 1 to 5, wherein the pH is between about 5 and about 7.

7. The composition according to any one of items 1 to 6, wherein the tonicity modifier is sorbitol and the buffer is a histidine buffer.

8. The composition according to any one of items 1 to 6, which is free of surfactants or amino acids.

9. The composition according to any one of items 4 to 7, which is free of surfactants or further amino acids.

10. The composition according to any one of items 1 to 9, which is essentially free of sodium chloride.

11. The composition according to any one of items 1 to 10, which is free of any further excipient.

12. The composition according to any one of items 1 to 11, wherein the compound neutralizing GM-CSF is selected from the group consisting of a polypeptide, a peptidomimetic, a nucleic acid, and a small molecule.

13. The composition according to item 12, wherein the polypeptide is an antibody or a functional fragment thereof binding to GM-CSF or to the GM-CSF receptor.

14. The composition according to item 13, wherein the antibody or the functional fragment thereof is a human monoclonal antibody or a functional fragment thereof.

15. The composition according to item 13 or 14, wherein the antibody is an IgG, an IgG1 or an IgG4 antibody.

16. The composition according to any one of items 13 to 15, wherein the antibody or the functional fragment thereof binds to an epitope of GM-CSF, the epitope preferably comprising amino acids 23-27 (RRLLN) and/or amino acids 65-77 (GLR/QGSLTKLKGPL).

17. The composition according to item 16, wherein said epitope further comprises:
(i) amino acids 28-31 (LSRD);
(ii) amino acids 32-33 (TA); and/or
(iii) amino acids 21-22 (EA).

18. The composition according to item 16 or 17, wherein said epitope is a discontinuous epitope.

19. The composition according to any one of items 13 to 18, wherein said antibody or functional fragment thereof comprises in its heavy chain variable region a CDR3 comprising an amino acid sequence chosen from the group consisting of those set out in any of the SEQ ID NOs:1-13 and 56.

20. The composition according to item 19, wherein any of said heavy chain variable region CDR3 sequences exists together in a heavy chain variable region with the heavy chain variable region CDR1 comprising the amino acid sequence set out in SEQ ID NO:14 and heavy chain variable region CDR2 comprising the amino acid sequence set out in SEQ ID NO:15.

21. The composition according to any one of items 13 to 20, wherein said antibody or functional fragment thereof comprises in its light chain variable region a CDR1 comprising the amino acid sequence set out in SEQ ID NO:16, a CDR2 comprising the amino acid sequence set out in SEQ ID NO:17, and a CDR3 comprising the amino acid sequence set out in SEQ ID NO:18.

22. The composition according to any one of items 13 to 21, wherein said antibody or functional fragment thereof comprises in its light chain variable region an amino acid sequence as set out in any of SEQ ID NOs:19, 54 and 55.

23. The composition according to any one of items 13 to 22, wherein said antibody or functional fragment thereof comprises in its heavy chain variable region an amino acid sequence as set out in any of SEQ ID NOs:20-33, 52 and 53.

24. The composition according to any one of items 13 to 23, wherein said antibody or functional fragment thereof comprises in its light chain variable region a CDR1 comprising an amino acid sequence as set out in SEQ ID NO:16, a CDR2 comprising an amino acid sequence as set out in SEQ ID NO:17 and a CDR3 comprising an amino acid sequence as set out in SEQ ID NO:18; and comprises in its heavy chain variable region a CDR1 comprising an amino acid sequence as set out in SEQ ID NO:14, a CDR2 comprising an amino acid sequence as set out in SEQ ID NO:15 and a CDR3 comprising an amino acid sequence as set out in any of SEQ ID NOs:1-13 and 56.

25. The composition according to any one of items 13 to 24, wherein said antibody or functional fragment thereof comprises in its light chain variable region a CDR1 comprising an amino acid sequence as set out in SEQ ID NO:16, a CDR2 comprising an amino acid sequence as set out in SEQ ID NO:17 and a CDR3 comprising an amino acid sequence as set out in SEQ ID NO:18; and comprises in its heavy chain variable region a CDR1 comprising an amino acid sequence as set out in SEQ ID NO:14, a CDR2 comprising an amino acid sequence as set out in SEQ ID NO:15 and a CDR3 comprising an amino acid sequence as set out in SEQ ID NO:2.

26. The composition according to any one of items 13 to 25, wherein said antibody or functional fragment thereof comprises a light chain amino acid sequence as set out in SEQ ID NO:34 and a heavy chain amino acid sequence chosen from the group consisting of those as set out in any of SEQ ID NOs:35-48.

27. The composition according to any one of items 13 to 26, wherein said antibody or functional fragment thereof comprises an amino acid sequence bearing at least 70% homology to the respective amino acid sequence as set out in any of SEQ ID NOs:1-48 and 52-56, preferably to the respective amino acid sequence as set out in any of SEQ ID NOs:1-18 and 56 and/or to the amino acid sequence of the framework regions within the amino acid sequence as set out in any of SEQ ID NOs:19-48 and 52-55.

28. The composition according to any one of the preceding items which comprises:
   i) about 100 mg/ml to about 180 mg/ml of a compound neutralizing GM-CSF;
   ii) about 5% (w/v) sorbitol;
   iii) about 30 mM L-histidine; and
   iv) has a pH of about 5.8.

29. The composition according to item 28, which comprises about 150 mg/ml of a compound neutralizing GM-CSF.

30. The composition according to any one of the preceding items which is a liquid, preferably an aqueous composition.

31. The composition according to any one of the preceding items, which is stable for at least 24 months at about 2-8° C. or at least 28 days at room temperature.

32. The composition according to any one of the preceding items for use in therapy.

33. The composition according to any one of the preceding items, which is for intravenous and/or subcutaneous administration.

34. The composition according to any one of the preceding items for use in the treatment of inflammatory and autoimmune disorders, preferably including allergic and psoriatic disorders, as well as arthritic and asthmatic disorders.

35. A kit comprising the composition of any one of the preceding items.

It should be understood that the inventions disclosed herein are not limited to particular methodology, protocols, or reagents, as such can vary. The discussion and examples provided herein are presented for the purpose of describing particular embodiments only and are not intended to limit the scope of the present invention, which is defined solely by the claims. The following examples will illustrate the present invention.

EXAMPLES

Example 1

Material

The following examples were carried out with a human monoclonal IgG1 antibody (in the following denoted as "the antibody") that binds to and neutralizes with high affinity and specificity human GM-CSF and that is described in WO 2006/111353. Its generation is described in Example 2 of WO 2006/111353. More specifically, the antibody comprises the light chain and heavy chain CDR sequences as depicted in SEQ ID NOs:16, 17, 18, 14, 15 and 2. These CDR sequences are comprised in the heavy and light chain variable domain, respectively, that are shown in SEQ ID NOs:34 and 35, respectively. GM-CSF is aberrantly overproduced in a multitude of pro-inflammatory and autoimmune human diseases, and addition of recombinant GM-CSF was found to aggravate such diseases. Possible disease indications for treatment with a GM-CSF-neutralizing antibody include rheumatoid arthritis (RA), asthma and other forms of lung inflammation, multiple sclerosis (MS) and psoriasis.

The antibody was produced in a bioreactor using serum- and protein-free medium. The inoculum for the production fermenter was prepared from a single vial of the antibody producing clone. Upon completion of the fermentation process, the harvest containing secreted antibody is processed by filtration to separate cells and debris from the supernatant. Purification of the harvest is based on common chromatographic approaches to reduce HCPs, DNA and potential viruses. An integral virus inactivation step was an additional part of the downstream process. For the formulation, a concentration and buffer exchange step was performed.

Example 2

Test Methods

Size Exclusion High Performance Liquid Chromatography (SE-HPLC) was established to determine the degree of aggregation of the antibody (HPLC: Agilent 1100 Chemstation; column: Tosoh Biosep TSKgel G4OOOSWXL). The SE-HPLC method was qualified by performing a nine-point range test, from which precision (six replicate injections) and linearity (triplicate standard curves) were determined and tested. All assays were performed using 100 mM $KH_2PO_4$, 200 mM $Na_2SO_4$, pH 6.6 as running buffer.

The surface plasmon resonance (SPR) method was established to determine the degree of antibody binding activity to immobilized GM-CSF (Biacore 3000/CM5 sensor chip/HBS-EP running buffer). The SPR method was qualified by performing a nine-point range test, from which precision (six replicate injections) and linearity (triplicate standard curves) were determined and tested.

Reducing and non-educing SDS-PAGE was performed for the detection of degradation products (fragments) and aggregates of the antibody.

Example 3

Effect of pH and Temperature Stress

A study was conducted to evaluate the stability of the antibody in low ionic strength screening buffer (LISSB: 2 mM glycine, 2 mM citric acid, 2 mM HEPES, 2 mM MES, and 2 mM Tris) at pH values ranging from 3 to 10. Antibody samples were stored in the respective solutions at 55° C. for a period of 14 days. At T0, T7 and T14 (days) samples were analyzed. The SPR analysis indicates that the antibody is most stable at pH 4-7. When analyzed by SE-HPLC the antibody monomer was found to be most stable at pH 4-6 (T14). Both non-reducing and reducing SDS-PAGE of the T14 samples show only minimal formation of degradation products and aggregates at pH 4-6.

Example 4

Effect of Ionic Strength and Temperature Stress

A study was conducted to evaluate the stability of the antibody in low ionic strength screening buffer (LISSB) in the presence of 0, 10, 100 and 500 mM NaCl. Antibody samples were dialyzed into solutions of LISSB (pH 4.5 and pH 7.5) with additional NaCl to a concentration of approximately 1 mg/ml and stored at 55° C. for a period of 14 days. At T0, T7 and T14 (days) samples were analyzed by SE-HPLC and SPR.

The HPLC and SPR studies indicate that the addition of salt deteriorates the stability of the antibody and that the effect is more pronounced at pH 4.5 than at pH 7.5. Furthermore, SE-HPLC data show that the destabilization of the antibody with elevated concentrations of salt (≥100 mM) at pH 4.5 mainly results in the accumulation of aggregates of the antibody. At pH 7.5 the destabilization of the antibody with elevated concentrations of salt (500 mM) mainly results in the accumulation of degradation products of the antibody. In LISSB pH 4.5; 500 mM NaCl, the level of precipitation (T7 and T14) of the antibody was very high.

Example 5

Effect of Buffers

A study was conducted to evaluate the stability of the antibody in various buffers pH 5-7. Antibody samples were dialyzed into solutions of 20 mM citrate buffer pH 5, 6 and 7; 20 mM phosphate buffer pH 6 and pH 7; 20 mM succinate buffer pH 6 and pH 7, 20 mM histidine buffer pH 6 and pH 7; and 20 mM acetate buffer pH 5 and pH 6 to a concentration of approximately 1 mg/ml and stored at 55° C. for a period of 14 days. At T0, T7 and T14 (days) samples were analyzed by SE-HPLC, SPR, and reducing and non-reducing SDS-PAGE.

The SPR study, the HPLC monomer and aggregate data and the reducing and non-reducing SDS-PAGE indicate that the antibody is most stable in acetate buffer pH 5, histidine buffer pH 6 and citrate buffer pH 5, 6 and 7 (T14 data).

Example 6

Effect of Amino Acids

A study was conducted to evaluate the stability of the antibody in low ionic strength screening buffer (LISSB) with the addition of different amino acids. Antibody samples were stored in the solution at pH 6 with 250 mM of the respective amino acid at 55° C. for a period of 14 days. At T0, T7 and T14 (days) samples were analyzed. The SPR study indicates a slight stabilizing effect especially of glutamic acid, threonine, lysine and valine (T14). The HPLC data indicate a stabilizing and significant effect of glutamic acid, threonine and alanine resulting in approximately 2-3% more intact monomer and about 30%, 31% and 20% less aggregates, respectively, compared to the reference without any amino acid added.

Example 7

Effect of Sugars and Surfactants

A study was conducted to evaluate the stability of the antibody in low ionic strength screening buffer (LISSB) with the addition of various sugars or surfactants. Antibody samples were dialyzed into solutions of LISSB pH 6.0 to a concentration of approximately 1 mg/ml with an additional 6% (w/v) sugars (D-mannitol, D-sorbitol, sucrose, D-mannose, D-maltose, D-trehalose, D-glucose), 0.05% (v/v) Tween 20 or 0.02% (v/v) Tween 80, and stored at 55° C. for a period of 14 days. At T0, T7 and T14 (days) samples were analyzed by SE-HPLC, SPR and reducing and non-reducing SDS-PAGE.

The SPR and HPLC studies indicate that D-sorbitol and D-mannitol improve the stability of the antibody by about 20%/3% (SPR/HPLC data, T14) and 14%/4% (SPR/HPLC data, T14), respectively. Trehalose and sucrose both have reduced effects by 7%/0.7% (SPR/HPLC data, T14) and 6%/2% (SPR/HPLC data, T14), respectively. Furthermore, the HPLC data indicate that D-sorbitol and D-mannitol reduce the formation of the antibody aggregates by 43% and 50%, respectively, which is also supported by data obtained by SDS-PAGE. Neither 0.05% (v/v) Tween 20 nor 0.02% (v/v) Tween 80 seem to significantly improve the stability of the antibody.

Example 8

Effect of Combinations of Buffers, Amino Acids and Sugars

Based on previous studies, a study was conducted to evaluate the stability of 1 mg/ml of the antibody formulated in combinations of buffers, amino acids and sugars. Previous studies indicated stabilizing effects of: 20 mM acetate pH 5; 20 mM histidine pH 6; 250 mM glutamic acid; 250 mM threonine, 6% (w/v) sorbitol and 6% (w/v) mannitol. The antibody was formulated at a concentration of 5.4 mg/ml into solutions of combinations of 20 mM buffer, 250 mM amino acid and 6% (v/v) sugar as indicated in Table 1, and stored at 55° C. for a period of 14 days. Antibody in 1×PBS was included as a control. At T0, T7 and T14 (days), samples were analyzed by SE-HPLC and SPR.

Additionally, T0 samples comprising the antibody (5.4 mg/ml) in 1×PBS were tested for susceptibility to freezing and thawing. Storage vials were frozen slowly at −20° C. in the freezer. After freezing was complete, the samples were thawed at room temperature. This process was repeated until five freezing-thawing cycles had been completed. Each sample was examined for SPR and SE-HPLC recovery after two and five cycles.

TABLE 1

Combination of buffers, sugars and amino acids (Ac = acetate buffer; His = histidine buffer; M = mannitol; S = sorbitol)

| Sample | | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| Buffer | Ac | x | x | | | x | x | | | x | x | x | x | | | | | 1×PBS |
| | His | | | x | x | | | x | x | | | | | x | x | x | x | |
| Amino | Glu | x | | x | | | | x | x | | | x | x | | | | | |
| acid | Thr | | x | | x | | | | | | | x | x | | | x | x | |

TABLE 1-continued

Combination of buffers, sugars and amino acids (Ac = acetate buffer; His = histidine buffer; M = mannitol; S = sorbitol)

| Sample | | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| Sugar | M | | | | | x | | x | | x | | x | | x | | x | | |
| | S | | | | | | x | | x | | x | | x | | x | | x | |

The SPR data show that binding activities in samples 5-16 at T14/55° C. are >93% relative to T0. For the antibody in 1×PBS (sample 17) and samples 1-4 (all without mannitol or sorbitol), the numbers are 62%, 19%, 26%, 91% and 85%, respectively. The SPR data therefore indicate that adding mannitol or sorbitol improves the stability of the binding activity. Furthermore, samples 1-4 appeared yellowish at T7 and T14 indicating oxidation. The SE-HPLC data show that the lowest levels of aggregates (3.5%-5.6%) and degradation products (4.2%-5.4%) are found in samples 5-8, 11-12 and 15-16 (T14/55° C. data), supporting the stabilizing effect of mannitol and sorbitol on the antibody monomer and indicating a possible minor effect of adding 250 mM threonine. The effect of threonine is however at least only minimal judged by the monomer levels found in samples 5-8, 11-12 and 15-16 (91.2%, 89.8%, 91.5%, 90.8%, 89.8%, 89.0%, 91.4% and 90.9%, respectively)—for sample 17 (PBS) the number is 80.3% (T14/55° C. data). 250 mM glutamic acid together with sorbiol or mannitol has a negative effect on the stability of the antibody monomer, especially in acetate buffer. In conclusion, the antibody monomer seems to be most stable in combination of 20 mM acetate buffer pH 5 or 20 mM histidine buffer pH 6 and 6% (w/v) sorbitol or 6% (w/v) mannitol.

The SE-HPLC data from the freezing/thawing experiments indicate a minor superior effect of sorbitol over mannitol in stabilizing the antibody monomer. In samples 6 and 8 the monomer content is 98.6% and 98.4%, respectively, after 5 rounds of freezing/thawing compared to monomer contents in samples 5 and 7 of 96.9% and 96.0%.

Example 9

Effect of Combinations of Histidine or Acetate Buffers, Sorbitol or Mannitol, and Tween 20 or Tween 80

Based on the stability data from the previous studies (showing a stabilizing effect in particular of 20 mM acetate pH 5, 20 mM histidine pH 6, 6% (w/v) sorbitol and 6% (w/v) mannitol), a new study was conducted to evaluate the stability of 10 mg/ml of the antibody formulated in combinations of histidine or acetate buffers, sorbitol or mannitol, and Tween 20 or Tween 80. Due to concentrations of the antibody at 10 mg/ml, addition of 0.02% (w/v) Tween 20 and 0.02% (w/v) Tween 80 was also tested for its effect on aggregation.

The antibody was formulated at a concentration of 10 mg/ml into solutions of 20 mM acetate buffer pH 5.0 or 20 mM histidine buffer pH 6.0 and with the additives as indicated in Table 2, and stored at 55° C. for a period of 14 days. At T0, T7 and T14 (days) samples were analyzed by SE-HPLC and SPR.

Additionally, antibody samples were tested for susceptibility to freezing and thawing. The antibody was frozen slowly in a concentration of 10 mg/ml at −20° C. in the freezer. After freezing was complete, the samples were thawed at room temperature. This process was repeated until three and/or five freezing and thawing cycles had been completed. Each sample was examined for SPR and SE-HPLC recovery after three and/or five freezing and thawing cycles.

TABLE 2

Combination of buffers, sugars and detergents (Ac = acetate buffer; His = histidine buffer; M = mannitol; S = sorbitol; T20 = Tween 20; T80 = Tween 80)

| | Sample | 1 | 2 | 3 | 4 | 5 | 6 | 7 | 8 | 9 | 10 | 11 | 12 |
|---|---|---|---|---|---|---|---|---|---|---|---|---|---|
| Buffer | Ac | x | x | | | x | x | x | x | | | | |
| | His | | | x | x | | | | | x | x | x | x |
| Sugar | M | | x | | x | | x | x | | | x | | x |
| | S | x | | x | | x | x | | x | x | | x | |
| Detergent | T20 | | | | | x | | x | | x | | x | |
| | T80 | | | | | | x | | x | | x | | x |

The HPLC data clearly showed that 0.02% (w/v) Tween 20 and 0.02% (w/v) Tween 80 has a negative effect on the stability of the antibody monomer. After 14 days of storage at 55° C., about 89-90% monomer was left of antibody formulated without detergents and about 83-88% monomer was left of antibody formulated with detergents added. The loss of antibody monomer is mainly causing higher levels of antibody aggregates (about 7.6%-10.3%) when detergents are added. Without Tween 20 and Tween 80 the antibody aggregates constitute about 5.2%-6.4%. Although the difference between acetate and histidine as buffer system is minor, histidine seems at least as good as acetate.

The freezing and thawing experiments indicate that there is at least no positive effect of the detergents on the level of antibody monomer after five rounds of freezing and thawing. However, the antibody monomer is more stable when 6% (w/v) sorbitol is added to the formulation compared to 6% (w/v) mannitol. With mannitol added, the antibody monomer aggregates to a higher degree after five rounds of freezing and thawing. The HPLC data from the freezing and thawing experiment show no difference between the use of acetate and histidine.

In conclusion, a pre-formulation containing 20 mM histidine, pH 6.0 and 6% (w/v) sorbitol seems optimal for the stability of antibody monomer.

Example 10

Short-Term Stability Assessment of a 20 Mm Histidine, 6% (w/v) D-Sorbitol Pre-Formulation Based on the identification of 20 mM histidine pH 6.0, and 6% (w/v) sorbitol as optimal pre-formulation, a short-term stability test was conducted to evaluate this pre-formulation at higher concentrations of the antibody.

The antibody was formulated into the above solution at concentrations of approximately 22, 36, 42, 83 and 118 mg/ml. The formulated antibody was stored at 5° C. and 25°

C. for a period of up to 4 weeks. At T0, T14 and T28 (days) samples were analyzed by SE-HPLC.

The SE-HPLC data clearly show that the antibody is stable in 20 mM histidine pH 6.0, 6% (w/v) sorbitol. The concentration of antibody monomer detected after 28 days of storage at 5° C. or 25° C. was always above 97%, with the exception of the highest antibody concentration tested (118 mg/ml) at 25° C., where the antibody monomer concentration was about 96.5%. The results are shown in FIG. 1.

Example 11

Fine-Tuning of Final Excipients

Based on the data generated in the previous experiments, sorbitol and histidine have been chosen for stabilizing the antibody. In the next step, the amount of excipients as well as the pH value were fine-tuned for antibody concentrations between 10 and 100 mg/ml using "Design of Experiment" (DOE), including 3 center points and resulting in 30 individual runs. The randomized experimental plan was carried out with the following parameters:
  Antibody: 10-55-100 mg/ml
  pH: 5-6-7
  Histidine: 10-30-50 mM
  Sorbitol: 2-6-10% (w/v)

To allow short term evaluation, the samples were stressed at accelerated conditions of 50° C. for 14 days. Furthermore, three freeze thaw cycles (−20° C.) were performed to mimic storage of the antibody.

Results

Figure 2:
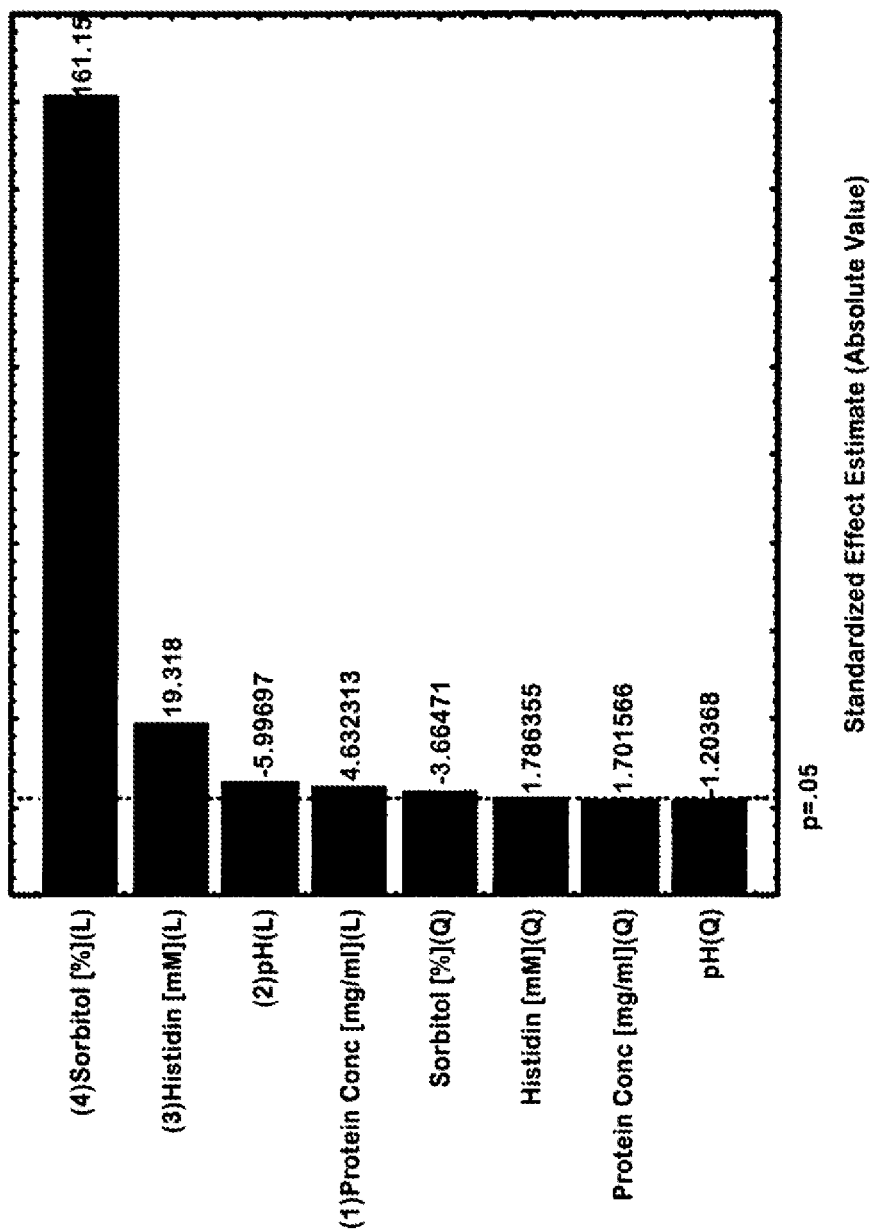
FIG. 2 is a Pareto chart of standardized effect with osmolality [mOsmol/kg] as variable.

Osmolality was determined to ensure physiological conditions for the formulation. For an i.v. or s.c. application of the antibody, an osmolality between 250 and 450 mOsmol/kg is an acceptable range. As shown in FIG. 2, osmolality is mainly controlled by the amount of sorbitol in the formulation. Both histidine in low concentrations (10-50 mM) and the antibody itself have only minimal effects on osmolality.

The dependency of osmolality on the sorbitol and histidine concentration can be depicted in a contour blot. This blot shows that in order to maintain osmolality in the physiological interval, a concentration between 3% and 7% (w/v) sorbitol is necessary. The generated data allude to an optimal sorbitol concentration of about 6%, resulting in a rather high osmolality value (>400 mOsmol/kg). Since a certain reduction of sorbitol does not impact stability of the antibody, sorbitol concentration can be decreased to 5% in order to reach an osmolality of about 350 mOsmol/kg and hence to increase patient convenience.

The optimal histidine concentration was set to 30 mM based on the generated data. In a concentration range between 10 mM and 50 mM histidine, no impact on aggregation or fragmentation, as measured by HP-SEC, was detected.

Aggregation of the antibody is mainly concentration dependent. Increased antibody concentrations result in a higher aggregate level and increased clarity values during freezing/thawing and at accelerated temperature stress conditions. Additionally the pH value affects the monomer content of the antibody. Whereas accelerated stress at pH<6 leads to increased fragmentation of the antibody, the stability during freezing/thawing is not affected, but rather a slightly better stability is observed. At pH values of pH>6, for both accelerated temperature and freeze/thaw treatment, reduced monomer content could be measured using HP-SEC and clarity analysis. In order to balance the contrary effects, a pH of 5.8 seems to be most appropriate for the antibody formulation.

This resulted in a formulation with the following parameters:

| | |
|---|---|
| Antibody | 10 mg/ml-55 mg/ml-100 mg/ml |
| D-sorbitol | 5% (w/v) |
| L-histidine buffer | 30 mM (hydrochloride monohydrate) |
| pH | 5.8 (adjusted with 2M sodium hydroxide) |

The conditions or parameters of this composition can also be transmitted to a composition having higher antibody concentrations, as will be shown in the following examples.

Example 12

Stability Studies a) Long-Term Studies

The study was designed for a testing period of up to 60 months. During this period, antibody samples were stored at +5° C.±3° C. in DIN R2 glass vials. In addition, an accelerated study at +25° C.±2° C. and a stress study at +40° C.±2° C. was performed in DIN R2 glass vials for up to 12 and 6 months, respectively. Testing was carried out using the antibody in a concentration of 106 mg/ml and 145 mg/ml, in a formulation with 30 mM histidine monohydrochloride and 5% (w/v) sorbitol at pH 5.8.

The following parameters were measured: pH, osmolality, concentration (OD280), percentage of monomers, aggregates and fragments by SE-HPLC, potency (cell based assay). The results are shown in the following Tables 3-8.

TABLE 3

Stability Testing at +5° C. ± 3° C. (106 mg/ml antibody)

| Storage Time [Months] | pH | Osmolality [mOsmol ·/kg] | Concentration (OD280) [mg ·/ml] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.83 | 379 | 106.51 | 99.20 | 0.80 | 0 | 0.83 |
| 1 | 5.88 | 379 | 103.00 | 99.18 | 0.82 | 0 | 1.03 |
| 3 | 5.90 | 379 | 108.75 | 99.07 | 0.93 | 0 | 1.23 |
| 6 | 5.89 | 376 | 100.05 | 98.87 | 1.13 | 0 | 0.89 |
| 9 | 5.83 | 377 | 102.59 | 99.01 | 0.99 | 0 | 1.00 |
| 12 | 5.86 | 387 | 103.34 | 98.97 | 1.03 | 0 | 1.01 |
| 18 | 5.87 | 379 | 102.49 | 98.78 | 1.04 | 0.18 | 0.84 |

TABLE 3-continued

Stability Testing at +5° C. ± 3° C. (106 mg/ml antibody)

| Storage Time [Months] | pH | Osmolality [mOsmol ·/kg] | Concentration (OD280) [mg ·/ml] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 24 | 5.85 | 377 | 101.73 | 98.68 | 1.11 | 0.21 | 1.05 |
| 30 | 5.81 | 383 | 102.52 | 98.55 | 1.17 | 0.28 | 0.83 |
| 36 | 5.84 | 380 | 107.78 | 98.56 | 1.18 | 0.25 | 1.06 |
| 42 | 5.92 | 384 | 96.32 | 98.34 | 1.11 | 0.55 | 1.26 |
| 48 | 5.90 | 376 | 94.33 | 98.54 | 1.23 | 0.23 | 1.03 |
| 54 | 5.86 | 382 | 107.67 | 98.25 | 1.28 | 0.47 | 1.04 |
| 60 | 5.90 | 379 | 106.79 | 98.26 | 1.26 | 0.48 | 0.97 |

TABLE 4

Stability Testing at +5° C. ± 3° C. (145 mg/ml antibody)

| Storage Time [Months] | pH | Osmolality [mOsmol · kg$^{-1}$] | Concentration (OD280) [mg · mL$^{-1}$] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.91 | 392 | 143.31 | 99.10 | 0.90 | 0 | 0.72 |
| 1 | 5.91 | 393 | 139.52 | 99.06 | 0.94 | 0 | 0.95 |
| 3 | 5.93 | 385 | 139.44 | 98.89 | 1.11 | 0 | 1.06 |
| 6 | 5.90 | 381 | 145.66 | 98.79 | 1.21 | 0 | 0.81 |
| 9 | 5.87 | 383 | 144.12 | 98.86 | 1.14 | 0 | 1.07 |
| 12 | 5.89 | 388 | 140.52 | 98.80 | 1.20 | 0 | 1.13 |
| 18 | 5.90 | 387 | 143.66 | 98.62 | 1.22 | 0.16 | 1.09 |
| 24 | 5.85 | 385 | 137.07 | 98.45 | 1.38 | 0.17 | 0.83 |
| 30 | 5.84 | 387 | 131.98 | 98.30 | 1.42 | 0.28 | 0.87 |
| 36 | 5.88 | 384 | 148.55 | 98.35 | 1.39 | 0.26 | 0.99 |
| 42 | 5.94 | 383 | 134.11 | 98.17 | 1.33 | 0.50 | 0.97 |
| 48 | 5.94 | 385 | 125.09 | 98.23 | 1.50 | 0.26 | 1.03 |
| 54 | 5.90 | 394 | 150.81 | 97.94 | 1.57 | 0.49 | 1.04 |
| 60 | 5.90 | 386 | 147.01 | 97.94 | 1.53 | 0.53 | 0.82 |

TABLE 5

Stability Testing at +25° C. ± 2° C. (106 mg/ml antibody)

| Storage Time [Months] | pH | Osmolality [mOsmol · kg$^{-1}$] | Concentration (OD280) [mg · mL$^{-1}$] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.83 | 379 | 106.51 | 99.20 | 0.80 | 0 | 0.83 |
| 1 | 5.84 | 385 | 101.35 | 98.77 | 1.06 | 0.17 | 1.20 |
| 3 | 5.90 | 382 | 107.36 | 98.15 | 1.44 | 0.42 | 0.92 |
| 6 | 5.85 | 387 | 100.14 | 97.85 | 1.51 | 0.64 | 1.00 |
| 9 | 5.83 | 374 | 107.49 | 94.71 | 1.49 | 3.80 | 1.10 |
| 12 | 5.85 | 383 | 106.27 | 94.71 | 1.56 | 3.73 | 1.30 |

TABLE 6

Stability Testing at +25° C. ± 2° C. (145 mg/ml antibody)

| Storage Time [Months] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.91 | 392 | 143.31 | 99.10 | 0.90 | 0 | 0.72 |
| 1 | 5.90 | 384 | 142.84 | 98.49 | 1.19 | 0.31 | 0.95 |
| 3 | 5.93 | 386 | 147.84 | 98.12 | 1.50 | 0.37 | 1.04 |
| 6 | 5.88 | 383 | 134.73 | 97.62 | 1.78 | 0.60 | 0.78 |
| 9 | 5.91 | 387 | 144.59 | 94.46 | 1.85 | 3.69 | 0.97 |
| 12 | 5.87 | 387 | 143.12 | 94.36 | 1.90 | 3.74 | 1.23 |

TABLE 7

Stability Testing at +40° C. ± 2° C. (106 mg/ml antibody)

| Storage Time [Months] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.83 | 379 | 106.51 | 99.20 | 0.80 | 0 | 0.83 |
| 1 | 5.88 | 377 | 102.68 | 94.66 | 1.34 | 3.99 | 1.05 |
| 3 | 5.89 | 382 | 108.60 | 91.85 | 2.06 | 6.09 | 1.01 |
| 6 | 5.85 | 378 | 99.75 | 87.39 | 2.46 | 10.15 | 0.97 |

TABLE 8

Stability Testing at +40° C. ± 2° C. (145 mg/ml antibody)

| Storage Time [Months] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.91 | 392 | 143.31 | 99.10 | 0.90 | 0 | 0.72 |
| 1 | 5.92 | 388 | 136.96 | 94.96 | 1.69 | 3.35 | 0.77 |
| 3 | 5.91 | 386 | 143.07 | 92.02 | 2.40 | 5.58 | 0.87 |
| 6 | 5.88 | 388 | 137.11 | 86.56 | 3.33 | 10.11 | 0.94 | b) Accelerated/Stress Studies

To demonstrate comparability of drug substance after scaling up, a stability study has been performed at accelerated (25° C.) and stressed (40° C.) conditions using two batches of drug substance with antibody concentrations of 165 mg/ml and 171 mg/ml formulated in a solution of 30 mM Histidine, 5% sorbitol, pH 5.8.

The following parameters were measured: pH, osmolality, concentration (OD280), percentage of monomers, aggregates and fragments by SE-HPLC, potency (cell based assay). The results for the antibody concentration of 171 mg/ml are shown in the following Tables 9 and 10.

TABLE 9

Stability Testing at +25° C. ± 2° C. (171 mg/ml antibody)

| Storage Time [Months] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.7 | — | 169.00 | >99.0 | 0.6 | <1% | 0.97 |
| 2 | 5.6 | — | 171.00 | 98.3 | 1.7 | <1% | 0.92 |
| 3 | 5.7 | — | 173.00 | 98.0 | 2.0 | <1% | 1.14 |

TABLE 10

Stability Testing at +40° C. ± 2° C. (171 mg/ml antibody)

| Storage Time [Months] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0 | 5.7 | — | 169.0 | >99.0 | 0.6 | <1% | 0.97 |
| 2 | 5.6 | — | 171.0 | 92.5 | 2.9 | <5% | 0.90 |
| 3 | 5.7 | — | 175.0 | 90.3 | 3.5 | <7% | 0.91 | c) Freeze/Thaw Studies

Freeze/thaw stability was tested for antibody concentrations of 106 mg/ml and 145 mg/ml formulated in a solution of 30 mM Histidine pH 5.8 and 5% sorbitol. The antibody was frozen at −80° C.±10° C. for at least over night. Thawing was performed for ≥6 h at room temperature. A number of 0, 1, 3, 5, 7 and 10 freeze/thaw cycles was carried out.

The following parameters were measured: pH, osmolality, concentration (OD280), percentage of monomers, aggregates and fragments by SE-HPLC, potency (cell based assay). The results are shown in the following Tables 11 and 12.

TABLE 11

Freeze/Thaw Stability Testing at −80° C. ± 10° C. (106 mg/ml antibody)

| Number of F/T cycles [No.] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0x | 5.86 | 373 | 99.07 | 99.05 | 0.95 | 0 | 0.84 |
| 1x | 5.86 | 381 | 99.37 | 99.19 | 0.81 | 0 | 1.05 |
| 3x | 5.89 | 379 | 98.23 | 99.20 | 0.80 | 0 | 1.11 |
| 5x | 5.87 | 380 | 99.69 | 99.15 | 0.85 | 0 | 1.15 |
| 7x | 5.86 | 380 | 99.96 | 99.12 | 0.88 | 0 | 1.24 |
| 10x | 5.87 | 378 | 98.94 | 99.08 | 0.92 | 0 | 0.83 |

TABLE 12

Freeze/Thaw Stability Testing at −80° C. ± 10° C. (145 mg/ml antibody)

| Number of F/T cycles [No.] | pH | Osmolality [mOsmol · kg⁻¹] | Concentration (OD280) [mg · mL⁻¹] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0x | 5.86 | 373 | 133.13 | 98.94 | 1.06 | 0 | 0.81 |
| 1x | 5.90 | 379 | 132.98 | 99.11 | 0.89 | 0 | 1.16 |
| 3x | 5.89 | 380 | 134.56 | 99.09 | 0.91 | 0 | 1.04 |
| 5x | 5.90 | 384 | 132.74 | 99.07 | 0.93 | 0 | 1.11 |
| 7x | 5.90 | 383 | 134.54 | 99.03 | 0.97 | 0 | 1.04 |
| 10x | 5.91 | 385 | 132.89 | 98.96 | 1.04 | 0 | 1.05 | d) Shaking Stability

This study was initiated to get information about the impact of shear stress on the antibody during the process from filling to patient (e.g., filling, packaging, shipment). Therefore the antibody in a concentration of 106 mg/ml and 145 mg/ml and formulated in a solution of 30 mM Histidine pH 5.8 and 5% sorbitol was joggled on a vertical shaker in primary packaging material (DIN R2 glass vials). The vials were stored at +5° C.±3° C. up to 14 days on a shaker versus a control (stored unshaken at +5° C.±3° C.). Data point collection was carried out after 0, 1, 2, 3, 7 and 14 days.

The following parameters were measured: pH, osmolality, concentration (OD280), percentage of monomers, aggregates and fragments by SE-HPLC, and potency (cell based assay). The results are shown in the following Tables 13-16.

TABLE 13

Shaking Stability Testing at +5° C. ± 3° C. (106 mg/ml antibody) WITH Shaking

| Storage Time [days] | pH — | Osmolality [mOsmol · kg$^{-1}$] | Concentration (OD280) [mg · mL$^{-1}$] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0  | 5.86 | 373 | 99.07  | 99.05 | 0.95 | 0 | 0.84 |
| 1  | 5.89 | 375 | 96.37  | 99.07 | 0.93 | 0 | n.d. |
| 2  | 5.92 | 376 | 99.84  | 99.04 | 0.96 | 0 | n.d. |
| 3  | 5.88 | 384 | 99.69  | 99.04 | 0.96 | 0 | 0.95 |
| 7  | 5.85 | 377 | 99.39  | 99.05 | 0.95 | 0 | 1.00 |
| 14 | 5.89 | 379 | 100.14 | 99.06 | 0.94 | 0 | 0.87 |

TABLE 14

Shaking Stability Testing at +5° C. ± 3° C. (106 mg/ml antibody) WITHOUT Shaking

| Storage Time [days] | pH — | Osmolality [mOsmol · kg$^{-1}$] | Concentration (OD280) [mg · mL$^{-1}$] | Monomer (M) Aggregates (A) Fragments (F) SE-HPLC M/A/F [%] | | | Potency (Cell Based Assay) Relative potency (compared to reference standard) |
|---|---|---|---|---|---|---|---|
| 0  | 5.86 | 373 | 99.07 | 99.05 | 0.95 | 0 | 0.84 |
| 1  | 5.93 | 380 | 96.54 | 99.09 | 0.91 | 0 | n.d. |
| 2  | 5.94 | 379 | 99.60 | 99.08 | 0.92 | 0 | n.d. |
| 3  | 5.86 | 378 | 98.98 | 99.05 | 0.95 | 0 | 0.98 |
| 7  | 5.85 | 378 | 98.79 | 99.02 | 0.98 | 0 | 1.04 |
| 14 | 5.92 | 384 | 99.43 | 99.08 | 0.92 | 0 | 1.13 |

TABLE 15

Shaking Stability Testing at +5° C. ± 3° C. (145 mg/ml antibody) WITH Shaking

| Storage Time [days] | pH — | Osmolality [mOsmol · kg$^{-1}$] | Concentration (OD280) [mg · mL$^{-1}$] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0  | 5.96 | 382 | 133.13 | 98.94 | 1.06 | 0 | 0.81 |
| 1  | 5.92 | 381 | 132.32 | 98.97 | 1.03 | 0 | n.d. |
| 2  | 5.94 | 385 | 135.31 | 98.93 | 1.07 | 0 | n.d. |
| 3  | 5.89 | 384 | 133.54 | 98.91 | 1.09 | 0 | 0.89 |
| 7  | 5.85 | 382 | 132.17 | 99.01 | 0.99 | 0 | 1.19 |
| 14 | 5.90 | 384 | 134.88 | 98.95 | 1.05 | 0 | 0.98 |

TABLE 16

Shaking Stability Testing at +5° C. ± 3° C. (145 mg/ml antibody) WITHOUT Shaking

| Storage Time [days] | pH — | Osmolality [mOsmol · kg$^{-1}$] | Concentration (OD280) [mg · mL$^{-1}$] | Monomer (M) Aggregates (A) Fragments (F) SE-HPLC M/A/F [%] | | | Potency (Cell Based Assay) Relative Potency (compared to reference standard) |
|---|---|---|---|---|---|---|---|
| 0  | 5.96 | 382 | 133.13 | 98.94 | 1.06 | 0 | 0.81 |
| 1  | 5.92 | 382 | 132.70 | 98.98 | 1.02 | 0 | n.d. |
| 2  | 5.95 | 383 | 137.85 | 98.98 | 1.02 | 0 | n.d. |
| 3  | 5.89 | 385 | 138.28 | 98.93 | 1.07 | 0 | 0.71 |
| 7  | 5.88 | 380 | 133.11 | 98.93 | 1.07 | 0 | 1.16 |
| 14 | 5.90 | 387 | 135.40 | 98.93 | 1.07 | 0 | 0.79 | e) Results and Conclusion

A long term stability study including accelerated and stressed conditions was carried out for up to 60 months for antibody concentrations of about 106 mg/ml and about 145 mg/ml. Additional stability studies under accelerated and stressed conditions were also conducted for antibody concentrations up to about 171 mg/ml.

During the period of 60 months, the samples stored at +5° C.±3° C. for both concentrations showed less than 2% aggregation and had the same potency as compared to reference. After 12 months of storage at accelerated conditions (+25° C.±2° C.), both concentrations (106 mg/ml and 145 mg/ml) showed less than 2% aggregation and had the same potency as compared to the reference. After 6 months of storage at stressed conditions (+40° C.±2° C.), both concentrations showed less than 5% aggregation and had approximately the same potency as compared to the reference.

The data of the additional accelerated/stress studies showed stability for 3 months and 1 month at 25° C. and 40° C., respectively. This indicates that the stability at 2-8° C. can be expected to be comparable to the one obtained for antibody concentrations of 106 mg/ml and 145 mg/ml, as discussed above.

Furthermore the antibody is stable during at least 10 freeze/thaw cycles at −80° C.±10° C. at both tested antibody concentrations of about 106 mg/ml and about 145 mg/ml.

Finally, the shaking stability study was set up for a time period of 14 days on a vertical shaker at +5° C.±3° C. versus an unshaken control. During this period no trends on parameters to assess pH, osmolality, degradation, aggregation, fragmentation, concentration or potency could be detected. The shaking seems to have no impact on antibody stability.

Based on the above data, a shelf life of at least 60 months can be proposed for concentrations up to about 171 mg/ml at +5° C.±3° C.

Example 13

Viscosity Evaluation

Viscosity is determined with a rheometer. A rheometer is used for those fluids which cannot be defined by a single value of viscosity and therefore require more parameters to be set and measured than is the case for a viscometer.

For some fluids, viscosity is a constant over a wide range of shear rates (Newtonian fluids). The fluids without a constant viscosity (non-Newtonian fluids) cannot be described by a single number. Non-Newtonian fluids exhibit a variety of different correlations between shear stress and shear rate. Therefore, the viscosity is dependent on the temperature as well as the shear rate for non-Newtonian fluids. The viscosity is indicated in milli Pascal*seconds (mPas*s) at a given temperature and a given shear rate Y[1/sec].

The viscosity of the formulation with about 150 mg/ml of antibody is below 12 mPas*s at a shear rate between about 50 and about 1000 [1/sec] at a temperature of 20° C.

The viscosity of the formulation with about 150 mg/ml of antibody is below 20 mPas*s at a shear rate between about 50 and about 1000 [1/sec] at a temperature of 5° C.

What is claimed is:

1. An aqueous composition comprising an antibody or a functional fragment thereof binding to GM-CSF or to the GM-CSF receptor present in a concentration of at least about 50 mg/ml, a tonicity modifier selected from mannitol, sorbitol, sucrose and/or trehalose present in a concentration from about 1% to about 15% (w/v), and a buffer selected from a histidine, acetate and/or citrate buffer present in a concentration from about 10 mM to about 50 mM, wherein the pH is between about 5 and about 7 and wherein the composition is stable.

2. The composition according to claim 1, wherein the compound neutralizing GM-CSF is present in a concentration of at least about 100 mg/ml and less than about 200 mg/ml, the tonicity modifier is present in a concentration from about 3% to about 7% (w/v) and the buffer is present in a concentration from about 20 mM to about 40 mM.

3. The composition according to claim 1, wherein the pH is between about 5 and about 7.

4. The composition according to claim 1, wherein the tonicity modifier is sorbitol and the buffer is a histidine buffer.

5. The composition according to claim 1, which is free of surfactants or amino acids.

6. The composition according to claim 1, wherein the antibody or the functional fragment thereof is a human monoclonal antibody or a functional fragment thereof.

7. The composition according to claim 1 which comprises:
   i) about 100 mg/ml to about 180 mg/ml of the antibody or a functional fragment thereof binding to GM-CSF or to the GM-CSF receptor;
   ii) about 5% (w/v) sorbitol;
   iii) about 30 mM L-histidine; and
   iv) has a pH of about 5.8.

8. The composition according to claim 7, which comprises about 150 mg/ml of the antibody or a functional fragment thereof binding to GM-CSF or to the GM-CSF receptor.

9. The composition according to claim 1, which is stable for at least 24 months at about 2-8° C. or at least 28 days at room temperature.

10. The composition according to claim 1, wherein the antibody or functional fragment thereof is a human monoclonal antibody or functional fragment thereof binding to GM-CSF which comprises in its light chain variable region a CDR1 comprising an amino acid sequence as set out in SEQ ID NO: 16, a CDR2 comprising an amino acid sequence as set out in SEQ ID NO: 17 and a CDR3 comprising an amino acid sequence as set out in SEQ ID NO: 18, and in its heavy chain variable region a CDR1 comprising an amino acid sequence as set out in SEQ ID NO: 14, a CDR2 comprising an amino acid sequence as set out in SEQ ID NO: 15 and a CDR3 comprising an amino acid sequence selected from the group consisting of those set out in SEQ ID NOs: 1-13 and 56.

11. The composition according to claim 1, wherein the antibody or functional fragment thereof is a human monoclonal antibody or functional fragment thereof binding to GM-CSF which comprises in its light chain variable region a CDR1 comprising an amino acid sequence as set out in SEQ ID NO: 16, a CDR2 comprising an amino acid sequence as set out in SEQ ID NO: 17 and a CDR3 comprising an amino acid sequence as set out in SEQ ID NO: 18, and in its heavy chain variable region a CDR1 comprising an amino acid sequence as set out in SEQ ID NO: 14, a CDR2 comprising an amino acid sequence as set out in SEQ ID NO: 15 and a CDR3 comprising an amino acid sequence as set out in SEQ ID NO: 2.

12. The composition according to claim 11, wherein the human monoclonal antibody or functional fragment thereof binding to GM-CSF comprises in its light chain variable region an amino acid sequence as set out in any of SEQ ID NOs. 19, 54 and 55 and in its heavy chain variable region an amino acid sequence as set out in any of SEQ ID NOs: 20-33, 52 and 53.

13. The composition according to claim 11, wherein the human monoclonal antibody or functional fragment thereof binding to GM-CSF comprises a light chain amino acid sequence as set out in SEQ ID NO: 34 and a heavy chain amino acid sequence as set out in SEQ ID NO: 35.

14. The composition according to claim 1, which is for intravenous and/or subcutaneous administration.

15. The composition according to claim 1 for use in therapy.

16. The composition according to claim 1 for use in the treatment of inflammatory and autoimmune disorders.

17. The composition according to claim 16, wherein the disorders are selected from allergic, psoriatic, arthritic and asthmatic disorders.

18. A kit comprising the composition according to claim 1.

* * * * *

SEQUENCE LISTING

```
<160> NUMBER OF SEQ ID NOS: 56

<210> SEQ ID NO 1
<211> LENGTH: 10
<212> TYPE: PRT
<213> ORGANISM: artificial sequence
<220> FEATURE:
<223> OTHER INFORMATION: Unknown
      CDR-H3 7A-701

<400> SEQUENCE: 1

Ser Gly Leu Ile Ala Asn His Met Thr Pro
1               5                   10

<210> SEQ ID NO 2
<211> LENGTH: 10
<212> TYPE: PRT
<213> ORGANISM: artificial sequence
<220> FEATURE:
<223> OTHER INFORMATION: Unknown
      CDR-H3 7B1-502

<400> SEQUENCE: 2

Thr Thr Leu Ile Ser Val Tyr Phe Asp Tyr
1               5                   10

<210> SEQ ID NO 3
<211> LENGTH: 10
<212> TYPE: PRT
<213> ORGANISM: artificial sequence
<220> FEATURE:
<223> OTHER INFORMATION: Unknown
      CDR-H3 L38-A1
```

```
<400> SEQUENCE: 3

Ser Gly Leu Ile Phe Asp Tyr Trp Leu Asp
1               5                   10

<210> SEQ ID NO 4
<211> LENGTH: 10
<212> TYPE: PRT
<213> ORGANISM: artificial sequence
<220> FEATURE:
<223> OTHER INFORMATION: Unknown
      CDR-H3 L38-A12

<400> SEQUENCE: 4

Ser Gly Leu Ile Ile Asp Ala Leu Ser Pro
1               5                   10

<210> SEQ ID NO 5
<211> LENGTH: 10
<212> TYPE: PRT
<213> ORGANISM: artificial sequence
<220> FEATURE:
<223> OTHER INFORMATION: Unknown
      CDR-H3 L38-G7

<400> SEQUENCE: 5

Thr Ser Leu Met Ser Ile Tyr Phe Asp Tyr
1               5                   10

<210> SEQ ID NO 6
<211> LENGTH: 10
<212> TYPE: PRT
<213> ORGANISM: artificial sequence
<220> FEATURE:
<223> OTHER INFORMATION: Unknown
      CDR-H3 L39-D11

<400> SEQUENCE: 6

Ser Gly Leu Leu Phe Leu Tyr Phe Asp Tyr
1               5                   10

<210> SEQ ID NO 7
<211> LENGTH: 10
<212> TYPE: PRT
<213> ORGANISM: artificial sequence
<220> FEATURE:
<223> OTHER INFORMATION: Unknown
      CDR-H3 E1-37-E7

<400> SEQUENCE: 7

Ser Gly Leu Ile Asn Leu Gly Met His Pro
1               5                   10

<210> SEQ ID NO 8
<211> LENGTH: 10
<212> TYPE: PRT
<213> ORGANISM: artificial sequence
<220> FEATURE:
<223> OTHER INFORMATION: Unknown
      CDR-H3 M1_3-82

<400> SEQUENCE: 8

Ser Gly Leu Ile Phe Asp Ala Leu Arg Asp
1               5                   10

<210> SEQ ID NO 9
<211> LENGTH: 10
<212> TYPE: PRT
```

```
<213> ORGANISM: artificial sequence
<220> FEATURE:
<223> OTHER INFORMATION: Unknown
      CDR-H3 Ln4p-23

<400> SEQUENCE: 9

Ser Gly Leu Ile Phe Asp Lys Leu Thr Ser
1               5                   10

<210> SEQ ID NO 10
<211> LENGTH: 10
<212> TYPE: PRT
<213> ORGANISM: artificial sequence
<220> FEATURE:
<223> OTHER INFORMATION: Unknown
      CDR-H3 Ln4p-28

<400> SEQUENCE: 10

Ser Gly Leu Ile Asn Leu His Phe Asp Thr
1               5                   10

<210> SEQ ID NO 11
<211> LENGTH: 10
<212> TYPE: PRT
<213> ORGANISM: artificial sequence
<220> FEATURE:
<223> OTHER INFORMATION: Unknown
      CDR-H3 Ln4p-50

<400> SEQUENCE: 11

Ser Thr His Phe Ser Ala Tyr Phe Asp Tyr
1               5                   10

<210> SEQ ID NO 12
<211> LENGTH: 10
<212> TYPE: PRT
<213> ORGANISM: artificial sequence
<220> FEATURE:
<223> OTHER INFORMATION: Unknown
      CDR-H3 Ln4p-65

<400> SEQUENCE: 12

Ser Gly Leu Ile Met Asp Lys Leu Asp Asn
1               5                   10

<210> SEQ ID NO 13
<211> LENGTH: 10
<212> TYPE: PRT
<213> ORGANISM: artificial sequence
<220> FEATURE:
<223> OTHER INFORMATION: Unknown
      CDR-H3 Ln4p-90

<400> SEQUENCE: 13

Ser Gly Leu Ile Ile Asp Asn Leu Asn Pro
1               5                   10

<210> SEQ ID NO 14
<211> LENGTH: 5
<212> TYPE: PRT
<213> ORGANISM: artificial sequence
<220> FEATURE:
<223> OTHER INFORMATION: Unknown
      CDR-H1 7B1-502

<400> SEQUENCE: 14

Asp Tyr Leu Leu His
1               5
```

```
<210> SEQ ID NO 15
<211> LENGTH: 17
<212> TYPE: PRT
<213> ORGANISM: artificial sequence
<220> FEATURE:
<223> OTHER INFORMATION: Unknown
      CDR-H2 7B1-502

<400> SEQUENCE: 15

Trp Leu Asn Pro Tyr Ser Gly Asp Thr Asn Tyr Ala Gln Lys Phe Gln
1               5                   10                  15

Gly

<210> SEQ ID NO 16
<211> LENGTH: 11
<212> TYPE: PRT
<213> ORGANISM: artificial sequence
<220> FEATURE:
<223> OTHER INFORMATION: Unknown
      CDR-L1 5-306

<400> SEQUENCE: 16

Arg Ala Ser Gln Asn Ile Arg Asn Ile Leu Asn
1               5                   10

<210> SEQ ID NO 17
<211> LENGTH: 7
<212> TYPE: PRT
<213> ORGANISM: artificial sequence
<220> FEATURE:
<223> OTHER INFORMATION: Unknown
      CDR-L2 5-306

<400> SEQUENCE: 17

Ala Ala Ser Asn Leu Gln Ser
1               5

<210> SEQ ID NO 18
<211> LENGTH: 9
<212> TYPE: PRT
<213> ORGANISM: artificial sequence
<220> FEATURE:
<223> OTHER INFORMATION: Unknown
      CDR-L3 5-306

<400> SEQUENCE: 18

Gln Gln Ser Tyr Ser Met Pro Arg Thr
1               5

<210> SEQ ID NO 19
<211> LENGTH: 107
<212> TYPE: PRT
<213> ORGANISM: artificial sequence
<220> FEATURE:
<223> OTHER INFORMATION: Unknown
      VL 5-306* L-version

<400> SEQUENCE: 19

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
                20                  25                  30

Leu Asn Trp Tyr Gln Gln Arg Pro Gly Lys Ala Pro Gln Leu Leu Ile
            35                  40                  45
```

```
Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys
                100                 105
```

<210> SEQ ID NO 20
<211> LENGTH: 119
<212> TYPE: PRT
<213> ORGANISM: artificial sequence
<220> FEATURE:
<223> OTHER INFORMATION: Unknown
      VH with CDR-H3 = 7A-701

<400> SEQUENCE: 20

```
Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Asn His Met Thr Pro Trp Gly Gln Gly
                100                 105                 110

Thr Met Val Thr Val Ser Ser
        115
```

<210> SEQ ID NO 21
<211> LENGTH: 119
<212> TYPE: PRT
<213> ORGANISM: artificial sequence
<220> FEATURE:
<223> OTHER INFORMATION: Unknown
      VH with CDR-H3 = 7B1-502*

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Leu Ile Ser Val Tyr Phe Asp Tyr Trp Gly Gln Gly
                100                 105                 110
```

```
Thr Met Val Thr Val Ser Ser
        115

<210> SEQ ID NO 22
<211> LENGTH: 119
<212> TYPE: PRT
<213> ORGANISM: artificial sequence
<220> FEATURE:
<223> OTHER INFORMATION: Unknown
      VH with CDR-H3 = 3077*

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser
        115

<210> SEQ ID NO 23
<211> LENGTH: 119
<212> TYPE: PRT
<213> ORGANISM: artificial sequence
<220> FEATURE:
<223> OTHER INFORMATION: Unknown
      VH with CDR-H3 = L38-A1

<400> SEQUENCE: 23

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Tyr Trp Leu Asp Trp Gly Gln Gly
            100                 105                 110

Thr Met Val Thr Val Ser Ser
        115

<210> SEQ ID NO 24
<211> LENGTH: 119
<212> TYPE: PRT
<213> ORGANISM: artificial sequence
<220> FEATURE:
```

```
<223> OTHER INFORMATION: Unknown
     VH with CDR-H3 = L38-A12

<400> SEQUENCE: 24

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
             20                  25                  30

Leu Leu His Trp Val Arg Gln Ala Pro Gly Gln Gly Leu Glu Trp Val
         35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Ser Gly Leu Ile Ile Asp Ala Leu Ser Pro Trp Gly Gln Gly
            100                 105                 110

Thr Met Val Thr Val Ser Ser
        115

<210> SEQ ID NO 25
<211> LENGTH: 119
<212> TYPE: PRT
<213> ORGANISM: artificial sequence
<220> FEATURE:
<223> OTHER INFORMATION: Unknown
     VH with CDR-H3 = L38-G7

<400> SEQUENCE: 25

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
             20                  25                  30

Leu Leu His Trp Val Arg Gln Ala Pro Gly Gln Gly Leu Glu Trp Val
         35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Thr Arg Thr Ser Leu Met Ser Ile Tyr Phe Asp Tyr Trp Gly Gln Gly
            100                 105                 110

Thr Met Val Thr Val Ser Ser
        115

<210> SEQ ID NO 26
<211> LENGTH: 119
<212> TYPE: PRT
<213> ORGANISM: artificial sequence
<220> FEATURE:
<223> OTHER INFORMATION: Unknown
     VH with CDR-H3 = L39-D11

<400> SEQUENCE: 26

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
```

```
            20                  25                  30
Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Leu Phe Leu Tyr Phe Asp Tyr Trp Gly Gln Gly
            100                 105                 110

Thr Met Val Thr Val Ser Ser
        115

<210> SEQ ID NO 27
<211> LENGTH: 119
<212> TYPE: PRT
<213> ORGANISM: artificial sequence
<220> FEATURE:
<223> OTHER INFORMATION: Unknown
      VH with CDR-H3 = E1-37-E7

<400> SEQUENCE: 27

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu Gly Met His Pro Trp Gly Gln Gly
            100                 105                 110

Thr Met Val Thr Val Ser Ser
        115

<210> SEQ ID NO 28
<211> LENGTH: 119
<212> TYPE: PRT
<213> ORGANISM: artificial sequence
<220> FEATURE:
<223> OTHER INFORMATION: Unknown
      VH with CDR-H3 = M1_3-82

<400> SEQUENCE: 28

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
```

```
                65                  70                  75                  80
Met Glu Leu Ser Arg Leu Arg Ser Asp Asp Thr Ala Val Tyr Tyr Cys
                    85                  90                  95

Ala Arg Ser Gly Leu Ile Phe Asp Ala Leu Arg Asp Trp Gly Gln Gly
            100                 105                 110

Thr Met Val Thr Val Ser Ser
        115
```

<210> SEQ ID NO 29
<211> LENGTH: 119
<212> TYPE: PRT
<213> ORGANISM: artificial sequence
<220> FEATURE:
<223> OTHER INFORMATION: Unknown
      VH with CDR-H3 = Ln4p-23

<400> SEQUENCE: 29

```
Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                    85                  90                  95

Ala Arg Ser Gly Leu Ile Phe Asp Lys Leu Thr Ser Trp Gly Gln Gly
            100                 105                 110

Thr Met Val Thr Val Ser Ser
        115
```

<210> SEQ ID NO 30
<211> LENGTH: 119
<212> TYPE: PRT
<213> ORGANISM: artificial sequence
<220> FEATURE:
<223> OTHER INFORMATION: Unknown
      VH with CDR-H3 = Ln4p-28

<400> SEQUENCE: 30

```
Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                    85                  90                  95

Ala Arg Ser Gly Leu Ile Asn Leu His Phe Asp Thr Trp Gly Gln Gly
            100                 105                 110

Thr Met Val Thr Val Ser Ser
```

<210> SEQ ID NO 31
<211> LENGTH: 119
<212> TYPE: PRT
<213> ORGANISM: artificial sequence
<220> FEATURE:
<223> OTHER INFORMATION: Unknown
      VH with CDR-H3 = Ln4p-50

<400> SEQUENCE: 31

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Thr His Phe Ser Ala Tyr Phe Asp Tyr Trp Gly Gln Gly
            100                 105                 110

Thr Met Val Thr Val Ser Ser
        115

<210> SEQ ID NO 32
<211> LENGTH: 119
<212> TYPE: PRT
<213> ORGANISM: artificial sequence
<220> FEATURE:
<223> OTHER INFORMATION: Unknown
      VH with CDR-H3 = Ln4p-65

<400> SEQUENCE: 32

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
            100                 105                 110

Thr Met Val Thr Val Ser Ser
        115

<210> SEQ ID NO 33
<211> LENGTH: 119
<212> TYPE: PRT
<213> ORGANISM: artificial sequence
<220> FEATURE:
<223> OTHER INFORMATION: Unknown VH with CDR-H3 = Ln4p-90

<400> SEQUENCE: 33

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Asn Leu Asn Pro Trp Gly Gln Gly
            100                 105                 110

Thr Met Val Thr Val Ser Ser
            115

<210> SEQ ID NO 34
<211> LENGTH: 214
<212> TYPE: PRT
<213> ORGANISM: artificial sequence
<220> FEATURE:
<223> OTHER INFORMATION: Unknown
      Light Chain 5-306* L-version

<400> SEQUENCE: 34

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys

-continued

```
210

<210> SEQ ID NO 35
<211> LENGTH: 449
<212> TYPE: PRT
<213> ORGANISM: artificial sequence
<220> FEATURE:
<223> OTHER INFORMATION: Unknown
      Heavy Chain with CDR-H3 = 7B1-502*

<400> SEQUENCE: 35
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Pro | Gly | Ala | |
| 1 | | | | 5 | | | | | 10 | | | | | 15 | |
| Ser | Val | Lys | Val | Ser | Cys | Lys | Ala | Phe | Gly | Tyr | Pro | Phe | Thr | Asp | Tyr |
| | | | 20 | | | | | 25 | | | | | 30 | | |
| Leu | Leu | His | Trp | Val | Arg | Gln | Ala | Pro | Gly | Gln | Gly | Leu | Glu | Trp | Val |
| | | | 35 | | | | | 40 | | | | | 45 | | |
| Gly | Trp | Leu | Asn | Pro | Tyr | Ser | Gly | Asp | Thr | Asn | Tyr | Ala | Gln | Lys | Phe |
| | 50 | | | | | 55 | | | | | 60 | | | | |
| Gln | Gly | Arg | Val | Thr | Met | Thr | Arg | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Thr | Arg | Thr | Thr | Leu | Ile | Ser | Val | Tyr | Phe | Asp | Tyr | Trp | Gly | Gln | Gly |
| | | | 100 | | | | | 105 | | | | | 110 | | |
| Thr | Met | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 36
<211> LENGTH: 449
<212> TYPE: PRT
<213> ORGANISM: artificial sequence
<220> FEATURE:
<223> OTHER INFORMATION: Unknown
      Heavy Chain with CDR-H3 =7A-701*

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Asn His Met Thr Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

-continued

```
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Thr Lys Asn Gln Val Ser Leu Thr
    355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
    435                 440                 445
Lys

<210> SEQ ID NO 37
<211> LENGTH: 449
<212> TYPE: PRT
<213> ORGANISM: artificial sequence
<220> FEATURE:
<223> OTHER INFORMATION: Unknown
      Heavy Chain with CDR-H3 = L38-A1*

<400> SEQUENCE: 37

Gln Val Gln Leu Val Gln Ser Gly Ala Glu Val Lys Lys Pro Gly Ala
1               5                   10                  15
Ser Val Lys Val Ser Cys Lys Ala Phe Gly Tyr Pro Phe Thr Asp Tyr
            20                  25                  30
Leu Leu His Trp Val Arg Gln Ala Pro Gly Gln Gly Leu Glu Trp Val
        35                  40                  45
Gly Trp Leu Asn Pro Tyr Ser Gly Asp Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Gly Leu Ile Phe Asp Tyr Trp Leu Asp Trp Gly Gln Gly
            100                 105                 110
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 38
<211> LENGTH: 449
<212> TYPE: PRT
<213> ORGANISM: artificial sequence
<220> FEATURE:
<223> OTHER INFORMATION: Unknown
      Heavy Chain with CDR-H3 = L38-A12*

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60
```

Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Ser Gly Leu Ile Ile Asp Ala Leu Ser Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 39
<211> LENGTH: 449
<212> TYPE: PRT
<213> ORGANISM: artificial sequence
<220> FEATURE:
<223> OTHER INFORMATION: Unknown
      Heavy Chain with CDR-H3 = L38-G7*

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Ser Leu Met Ser Ile Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu

```
385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 40
<211> LENGTH: 449
<212> TYPE: PRT
<213> ORGANISM: artificial sequence
<220> FEATURE:
<223> OTHER INFORMATION: Unknown
      Heavy Chain with CDR-H3 = L39-D11*

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
                35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Leu Phe Leu Tyr Phe Asp Tyr Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
```

```
                    290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 41
<211> LENGTH: 449
<212> TYPE: PRT
<213> ORGANISM: artificial sequence
<220> FEATURE:
<223> OTHER INFORMATION: Unknown
      Heavy Chain with CDR-H3 = E1-37-E7*

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
                35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu Gly Met His Pro Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
```

```
              195                 200                 205
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 42
<211> LENGTH: 449
<212> TYPE: PRT
<213> ORGANISM: artificial sequence
<220> FEATURE:
<223> OTHER INFORMATION: Unknown
      Heavy Chain with CDR-H3 = M1_3-82*

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Ala Leu Arg Asp Trp Gly Gln Gly
```

```
              100                 105                 110
Thr Met Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 43
<211> LENGTH: 449
<212> TYPE: PRT
<213> ORGANISM: artificial sequence
<220> FEATURE:
<223> OTHER INFORMATION: Unknown
      Heavy Chain with CDR-H3 = Ln4p-23*

<400> SEQUENCE: 43

Gln Val Gln Leu Val Gln Ser Gly Ala Glu Val Lys Lys Pro Gly Ala
```

-continued

```
1               5                   10                  15
Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
                35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Ser Gly Leu Ile Phe Asp Lys Leu Thr Ser Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
        435                 440                 445

Lys

<210> SEQ ID NO 44
<211> LENGTH: 449
<212> TYPE: PRT
<213> ORGANISM: artificial sequence
<220> FEATURE:
<223> OTHER INFORMATION: Unknown
      Heavy Chain with CDR-H3 = Ln4p-28*

<400> SEQUENCE: 44

Gln Val Gln Leu Val Gln Ser Gly Ala Glu Val Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu His Phe Asp Thr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

-continued

```
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 45
<211> LENGTH: 449
<212> TYPE: PRT
<213> ORGANISM: artificial sequence
<220> FEATURE:
<223> OTHER INFORMATION: Unknown
      Heavy Chain with CDR-H3 = Ln4p-50*

<400> SEQUENCE: 45

Gln Val Gln Leu Val Gln Ser Gly Ala Glu Val Lys Lys Pro Gly Ala
1               5                   10                  15
Ser Val Lys Val Ser Cys Lys Ala Phe Gly Tyr Pro Phe Thr Asp Tyr
            20                  25                  30
Leu Leu His Trp Val Arg Gln Ala Pro Gly Gln Gly Leu Glu Trp Val
        35                  40                  45
Gly Trp Leu Asn Pro Tyr Ser Gly Asp Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Thr Arg Ser Thr His Phe Ser Ala Tyr Phe Asp Tyr Trp Gly Gln Gly
                100                 105                 110
Thr Met Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
        260             265             270

Pro Glu Val Lys Phe Asn Trp Tyr Val Asp Gly Val Glu Val His Asn
    275             280             285

Ala Lys Thr Lys Pro Arg Glu Glu Gln Tyr Asn Ser Thr Tyr Arg Val
290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
        340             345             350

Leu Pro Pro Ser Arg Asp Glu Leu Thr Lys Asn Gln Val Ser Leu Thr
    355             360             365

Cys Leu Val Lys Gly Phe Tyr Pro Ser Asp Ile Ala Val Glu Trp Glu
370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
        420             425             430

Ala Leu His Asn His Tyr Thr Gln Lys Ser Leu Ser Leu Ser Pro Gly
    435             440             445

Lys

<210> SEQ ID NO 46
<211> LENGTH: 449
<212> TYPE: PRT
<213> ORGANISM: artificial sequence
<220> FEATURE:
<223> OTHER INFORMATION: Unknown
      Heavy Chain with CDR-H3 = Ln4p-65*

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 47
<211> LENGTH: 449
<212> TYPE: PRT
<213> ORGANISM: artificial sequence
<220> FEATURE:
<223> OTHER INFORMATION: Unknown
      Heavy Chain with CDR-H3 = Ln4p-90*

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45
```

-continued

```
Gly Trp Leu Asn Pro Tyr Ser Gly Asp Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Gly Leu Ile Ile Asp Asn Leu Asn Pro Trp Gly Gln Gly
                100                 105                 110

Thr Met Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 48
<211> LENGTH: 449
<212> TYPE: PRT
<213> ORGANISM: artificial sequence
<220> FEATURE:
<223> OTHER INFORMATION: Unknown
      Heavy Chain with CDR-H3 = 3077*

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 49
<211> LENGTH: 127
<212> TYPE: PRT
<213> ORGANISM: Homo sapiens

<400> SEQUENCE: 49

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 50
<211> LENGTH: 127
<212> TYPE: PRT
<213> ORGANISM: Artificial Sequence
<220> FEATURE:
<223> OTHER INFORMATION: Unknown
      Macaca GM-CSF

<400> SEQUENCE: 50

Ala Pro Ala Arg Ser Pro Ser Pro Gly Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Lys Thr Val Glu Val Val Ser Glu Met Phe Asp
            35                  40                  45

Leu Gln Glu Pro Ser Cys Leu Gln Thr Arg Leu Glu Leu Tyr Lys Gln
    50                  55                  60

Gly Leu Gln Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Gln Ser Phe Lys Glu Asn Leu Lys Asp

```
                100             105             110
Phe Leu Leu Val Ile Pro Phe Asp Cys Trp Glu Pro Val Gln Glu
        115             120             125

<210> SEQ ID NO 51
<211> LENGTH: 127
<212> TYPE: PRT
<213> ORGANISM: Artificial Sequence
<220> FEATURE:
<223> OTHER INFORMATION: Unknown
      Gibbon GM-CS

<400> SEQUENCE: 51

Ala Pro Ser Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Ile Asn Glu Thr Val Glu Val Val Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Ile Phe Glu Ser Phe Lys Glu Asn Leu Lys Asp
            100                 105                 110

Phe Leu Leu Val Ile Pro Phe Asp Cys Trp Glu Pro Val Gln Gly
        115                 120                 125

<210> SEQ ID NO 52
<211> LENGTH: 119
<212> TYPE: PRT
<213> ORGANISM: artificial sequence
<220> FEATURE:
<223> OTHER INFORMATION: VH with CDR-H3 7B1-502

<400> SEQUENCE: 52

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
            100                 105                 110

Thr Met Val Thr Val Ser Ser
        115

<210> SEQ ID NO 53
<211> LENGTH: 119
<212> TYPE: PRT
<213> ORGANISM: artificial sequence
```

```
<220> FEATURE:
<223> OTHER INFORMATION: Unknown
      VH with CDR-H3 3077

<400> SEQUENCE: 53

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser
        115

<210> SEQ ID NO 54
<211> LENGTH: 107
<212> TYPE: PRT
<213> ORGANISM: artificial sequence
<220> FEATURE:
<223> OTHER INFORMATION: Unknown
      VL 5-306

<400> SEQUENCE: 54

Glu Leu Val Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105

<210> SEQ ID NO 55
<211> LENGTH: 107
<212> TYPE: PRT
<213> ORGANISM: artificial sequence
<220> FEATURE:
<223> OTHER INFORMATION: Unknown
      VL 5-306* V-version

<400> SEQUENCE: 55

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30
```

```
Leu Asn Trp Tyr Gln Gln Arg Pro Gly Lys Ala Pro Gln Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105

<210> SEQ ID NO 56
<211> LENGTH: 10
<212> TYPE: PRT
<213> ORGANISM: artificial sequence
<220> FEATURE:
<223> OTHER INFORMATION: Unknown
      CDR-H3 3077

<400> SEQUENCE: 56

Ser Gly Leu Ile Ala Val Tyr Phe Asp Tyr
1               5                   10
```